United States Patent [19]

Reff et al.

[11] Patent Number: 5,830,698

[45] Date of Patent: Nov. 3, 1998

[54] METHOD FOR INTEGRATING GENES AT SPECIFIC SITES IN MAMMALIAN CELLS VIA HOMOLOGOUS RECOMBINATION AND VECTORS FOR ACCOMPLISHING THE SAME

[75] Inventors: Mitchell E. Reff, San Diego; Richard Spence Barnett, San Marcos; Karen Retta McLachlan, Solana Beach, all of Calif.

[73] Assignee: IDEC Pharmaceuticals Corporation, San Diego, Calif.

[21] Appl. No.: 819,866

[22] Filed: Mar. 14, 1997

[51] Int. Cl.[6] ........................... C12P 21/02; C12N 15/63; C12N 15/52
[52] U.S. Cl. .................. 435/69.1; 435/172.3; 435/320.1; 536/23.2
[58] Field of Search ................................ 435/69.1, 172.3, 435/320.1; 536/23.2

[56] References Cited

PUBLICATIONS

Thomas et al. High frequency targeting of genes to specific sited in the mammalian genome. Cell vol. 44 pp. 419–428, 1986.

*Primary Examiner*—Nancy Degen
*Assistant Examiner*—John S. Brusca
*Attorney, Agent, or Firm*—Burns, Doane, Swecker & Mathis, LLP

[57] ABSTRACT

A method for achieving site specific integration of a desired DNA at a target site in a mammalian cell via homologous recombination is described. This method provides for the reproducible selection of cell lines wherein a desired DNA is integrated at a predetermined transcriptionally active site previously marked with a marker plasmid. The method is particularly suitable for the production of mammalian cell lines which secrete mammalian proteins at high levels, in particular immunoglobulins. Novel vectors and vector combinations for use in the subject cloning method are also provided.

38 Claims, 54 Drawing Sheets

DESMOND

HD = Salmonella HisD Gene
N3 = Neomycin Phosphotransferase Exon 3
D = Murine Dihydrofolate reductase
E = Cytomegalovirus and SV40 Enhancers
SA = Splice acceptor
BT = Mouse Beta Globin Major Promoter
B = Bovine Growth Hormone Polyadenylation
S = SV40 Early Polyadenylation
SV = SV40 Late Polyadenylation

FIG. 2A
Molly

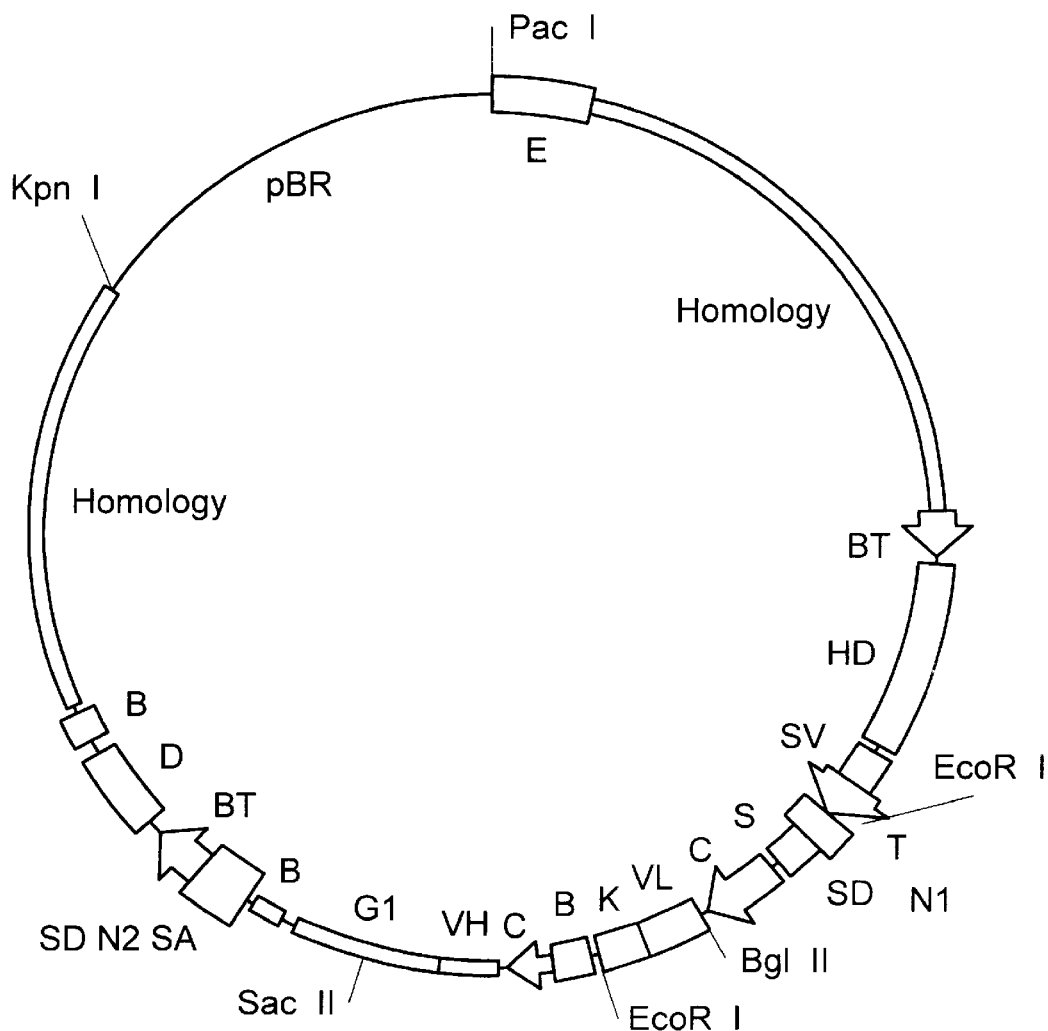

D = Dihydrofolate reductase
N1 + Neomycin Phosphotransferase Exon 1
N2 + Neomycin Phosphotransferase Exon 2
VL = Anti-CD20 Light chain leader + Variable
K = Human Kappa Constant
VH = Anti-CD20 Heavy chain Leader + Variable
G1 = Human Gamma 1 Constant
HD = Salmonella Histidinol Dehydrogenase
E = CMV and SV40 enhancers          S = SV40 Origin
SD = Splice donor                   SA = Splice acceptor
C = CMV promoter/enhancer
T = HSV TK promoter and Poloma enhancers
BT = Mouse Beta Globin Major Promoter
SV = SV40 Late Polyadenylation
B = Bovine Growth Hormone Polyadenylation

Southern Analysis of Desmond Marked CHO Cells

FIG. 7A

```
TTTCTAGACC TAGGGCGGGCC AGCTAGTAGC TTTGCTTCTC AATTTCTTAT TTGCATAATG
                                                                60
AGAAAAAAAG GAAAATTAAT TTTAACACCA ATTCAGTAGT TGATTGAGCA AATGCGTTGC
                                                               120
CAAAAAGGAT GCTTTAGAGA CAGTGTTCTC TGCACAGATA AGGACAAACA TTATTCAGAG
                                                               180
GGAGTACCCA GAGCTGAGAC TCCTAAGCCA GTGAGTGGCA CAGCCACACC TTGGTAAGGG
                                                               240
TGCTTGTCAT CACCGAAGCC TGATTCCGTA GAGCCAGGG CAGAGCATAT CCAATCTGCT
                                                               300
CACACAGGAT AGAGAGGGCA GGAGCCAGGG CAGAGCATAT AAGGTGAGGT AGGATCAGTT
                                                               360
GCTCCTCACA TTTGCTTCTG ACATAGTTGT GTGGGGAGCT TGGATAGCTT GGACAGCTCA
                                                               420
GGGCTGCGAT TTCGCGCCAA ACTTGACGGC AATCCTAGCG TGAAGGCTGG TAGGATTTTA
                                                               480
TCCCCGCTGC CATCATGGTT CGACCATTGA ACTGCATCGT CGCCGTGTCC CAAAATATGG
                                                               540
GGATTGGCAA GAACGGAGAC CTACCCTGGC CTCCGCTCAG GAACGAGTTC AAGTACTTCC
                                                               600
AAAGAATGAC CACAACCTCT TCAGTGGAAG GTAAACAGAA TCTGGTGATT ATGGGTAGGA
                                                               660
```

FIG. 7B

```
AAACCTGGTT CTCCATTCCT GAGAAGAATC GACCTTTAAA GGACAGAATT AATATAGTTC
                                                                720
TCAGTAGAGA ACTCAAAGAA CCACCACGAG GAGCTCATTT TCTTGCCAAA AGTTTGGATG
                                                                780
ATGCCTTAAG ACTTATTGAA CAACCGGAAT TGGCAAGTAA AGTAGACATG GTTTGGATAG
                                                                840
TCGGGAGGCAG TTCTGTTTAC CAGGAAGCCA TGAATCAACC AGGCCACCTT AGACTCTTTG
                                                                900
TGACAAGGAT CATGCAGGAA TTTGAAAGTG ACACGTTTTT CCCAGAAATT GATTGGGGGA
                                                                960
AATATAAACT TCTCCCAGAA TACCCAGGCG TCCTCTCTGA GGTCCAGGAG GAAAAAGGCA
                                                               1020
TCAAGTATAA GTTGAAGTC TACGAGAAGA AAGACTAACA GGAAGATGCT TTCAAGTTCT
                                                               1080
CTGCTCCCCT CCTAAAGCTA CTGTGCCTTC GGACTTTTGC TGGCTTTAGA
                                                               1140
TCAGCCTCGA CTGTGCCCTT TAGTTGCCAG CCATCTGTTG TTTGCCCCTC CCCCGTGCCT
                                                               1200
TCCTTGACCC TGGAAGGTGC CACTCCCACT GTCCTTCCT AATAAAATGA GGAAATTGCA
                                                               1260
TCGCATTGTC TGAGTAGGTG TCATTCTATT CTGGGGGGTG GGTGGGGCA GGACAGCAAG
                                                               1320
```

FIG. 7C

```
GGGGAGGATT GGGAAGACAA TAGCAGGCAT GCTGGGGATG CGGTGGGCTC TATGGAACCA
                                                                1380
GCTGGGGCTC GAAGCGGCCG CCCATTCGC TGGTGGTCAG ATGCGGGATG GCGTGGGACG
                                                                1440
CGGCGGGGAC CGTCACACTG AGGTTTCCG CCAGACGCCA CTGCTGCCAG GCGCTGATGT
                                                                1500
GCCCGGCTTC TGACCATGCG GTCGCGTTCG GTTGCACTAC GCGTACTGTG AGCCAGAGTT
                                                                1560
GCCCGGCGCT CTCCGGCTGC GGTAGTTCAG GCAGTTCAAT CAACTGTTTA CCTTGTGGAG
                                                                1620
CGACATCCAG AGGCACTTCA CCGCTTGCTA GCGGCTTACC ATCCAGCGCC ACCATCCAGT
                                                                1680
GCAGGAGCTC GTTATCGCTA TGACGGAACA GGTATTCGCT GGTCACTTCG ATGGTTTGCC
                                                                1740
CGGATAAACG GAACTGGAAA AACTGCTGCT GGTGTTTTGC TTCCGTCAGC GCTGGATGCG
                                                                1800
GCGTGCGGTC GGCAAAGACC AGACCGTTCA TACAGAACTG GCGATCGTTC GGCGTATCAC
                                                                1860
CAAAATCACC GCCGTAAGCC GACCACGGGT TGCCGTTTTC ATCATATTTA ATCAGGCACT
                                                                1920
GATCCCACCCA GTCCCAGACG AAGCCGCCCT GTAAACGGGG ATACTGACGA AACGCCCTGCC
                                                                1980
```

FIG. 7D

```
AGTATTTAGC GAAACCGCCA AGACTGTTAC CCATCGGCGTG GGCGTATTCG CAAAGGATCA  2040
GCGGGCGCGT CTCTCCGGGT AGCGAAAGCC ATTTTTTGAT GGACCATTTC GGACCAGCCG  2100
GGAAGGGCTG GTCTTCATCC ACGCGCGCGT ACATCGGGCA AATAATATCG GTGGCCGTGG  2160
TGTCGGCTCC GCCGCCTTCA TACTGCACCG GGCGGGAAGG ATCGACAGAT TTGATCCAGC  2220
GATACAGCGC GTCGTGATTA GCGCCGTGGC CTGATTCATT CCCCAGCGAC CAGATGATCA  2280
CACTCGGGTG ATTACGATCG CGCTGCACCA TTCGCGTTAC GCGTTCGCTC ATCGCCGGTA  2340
GCCAGCGCGG ATCATCGGTC AGACGATTCA TTGGCACCAT GCCGTGGGTT TCAATATTGG  2400
CTTCATCCAC CACATACAGG CCGTAGCGGT CGCACAGCGT GTACCACAGC GGATGGTTCG  2460
GATAATGCGA ACAGCGGCACG GCGTTAAAGT TGTTCTGCTT CATCAGCAGG ATATCCTGCA  2520
CCATCGTCTG CTCATCCATG ACCTGACCAT GCAGAGGATG ATGCTCGTGA CGGTTAACGC  2580
CTCGAATCAG CAACGGCTTG CCGTTCAGCA GCAGCAGACC ATTTCCAATC CGCACCCTCGC  2640
```

FIG. 7E

```
GGAAACCGAC ATCGCAGGCT TCTGCTTCAA TCAGCGTGCC GTCGGCGGTG TGCAGTTCAA
                                                                2700
CCACCGCACG ATAGAGATTC GGGATTTCGG CGCTCCACAG TTTCGGGTTT TCGACGTTCA
                                                                2760
GACGCAGTGT GACGCGATCG GCATAACCAC CAGGCTCATC GATAATTTCA CCGCCGAAAG
                                                                2820
GCGCGGTGCC GCTGGGCGACC TGCGTTTCAC CCTGCCATAA AGAAACTGTT ACCCGTAGGT
                                                                2880
AGTCACGCAA CTCGCCGCAC ATCTGAACTT CAGCCTCCAG TACAGCGCGG CTGAAATCAT
                                                                2940
CATTAAAGCG AGTGGCAACA TGGAAATCGC TGATTTGTGT AGTCGGTTTA TGCAGCAACG
                                                                3000
AGACGTCACG GAAAATGCCG CTCATCCGCC ACATATCCTG ATCTTCCAGA TAACTGCCGT
                                                                3060
CACTCCAACG CAGCACCATC ACCGCGAGGC GGTTTCTCC GGCGCGTAAA AATGCGCTCA
                                                                3120
GGTCAAATTC AGACGGGCAAA CGACTGTCCT GGCTGTAACC GACCCACGCC CCGTTGCACC
                                                                3180
ACAGATGAAA CGCCGAGTTA ACGCCATCAA AATAATTCG CGTCTGGCCT TCCTGTAGCC
                                                                3240
AGCTTTCATC AACATTAAAT GTGAGCGAGT AACAACCCGT CGGATTCTCC GTGGGAACAA
                                                                3300
```

FIG. 7F

```
ACGGGGGATT GACCGTAATG GGATAGGTTA CGTTGGTGTA GATGGGGGCA TCGTAACCGT
                                                              3360
GCATCTGCCA GTTTGAGGGG ACGACGACAG TATCGGCCCTC AGGAAGATCG CACTCCAGCC
                                                              3420
AGCTTTCCGG CACTGCTTCT GGTGCCGGAA ACCAGGCAAA GCGCCATTCG CCATTCAGGC
                                                              3480
TGCGCAACTG TTGGGAAGGG CGATCGGTGC GGGCCTCTTC GCTATTACGC CAGCTGGCGA
                                                              3540
AAGCGGGATG TGCTGCAAGG CGATTAAGTT GGGTAACGCC AGGGTTTTCC CAGTCACGAC
                                                              3600
GTTGTAAAAC GACTTAATCC GTCGAGGGGC TGCCTCGAAG CAGACGACCT TCCGTTGTGC
                                                              3660
AGCCAGCGGC GCCTGCGCCG GTGCCCACAA TCGTGCGCGA ACAAACTAAA CCAGAACAAA
                                                              3720
TCATACCGGC GGCACCGCCG CCACCACCTT CTCCTGTGCC TAACATTCCA GCGCCTCCAC
                                                              3780
CACTACCACC ACCATCGATG TCTGAATTGC CGCCCGCTCC ACCAATGCCG ACGGAACCTC
                                                              3840
AACCCGCTGC ACCTTTAGAC GACAGACAAC AATTGTTGGA AGCTATTAGA AACGAAAAAA
                                                              3900
ATCGCACTCG TCTCAGACCG GCTCTCTTAA GGTAGCTCAA ACCAAAAACG GCGCCCGAAA
                                                              3960
```

FIG. 7G

```
TTTCTAGACC TAGGGCGGCC AGCTAGTAGC TTTGCTTCTC AATTTCTTAT TTGCATAATG    60
AGAAAAAAAG GAAAATTAAT TTTAACACCA ATTCAGTAGT TGATTGAGCA AATGCGTTGC   120
CAAAAAGGAT GCTTTAGAGA CAGTGTTCTC TGCACAGATA AGGACAAACA TTATTCAGAG   180
GGAGTACCCA GAGCTGAGAC TCCTAAGCCA GTGAGTGGCA CAGCATTCTA GGGAGAAATA   240
TGCTTGTCAT CACCGAAGCC TGATTCCGTA GAGCCACACC TTGGTAAGGG CCAATCTGCT   300
CACACAGGAT AGAGAGGGCA GGAGCCAGGG CAGAGCATAT AAGGTGAGGT AGGATCAGTT   360
GCTCCTCACA TTTGCTTCTG ACATAGTTGT GTTGGGAGCT TGGATAGCTT GGACAGCTCA   420
GGGCTGGGAT TTCGCGCCAA ACTTGACGGC AATCCTAGCG TGAAGGCTGG TAGGATTTTA   480
TCCCCGCTGC CATCATGGTT CGACCATTGA ACTGCATCGT CGCCCGTGTCC CAAAATATGG   540
GGATTGGCAA GAACGGAGAC CTACCCTGGC CTCCGCTCAG GAACGAGTTC AAGTACTTCC   600
AAAGAATGAC CACAACCTCT TCAGTGGAAG GTAAACAGAA TCTGGTGATT ATGGGTAGGA   660
```

FIG. 7H

```
CCTGCTGGGG AGCCTGGGGA CTTCCACAC CCTAACTGAC ACACATTCCA CAGAATTAAT
                                                                4680
TCCCCTAGTT ATTAATAGTA ATCAATTACG GGGTCATTAG TTCATAGCCC ATATATGGAG
                                                                4740
TTCCGCGTTA CATAACTTAC GGTAAATGGC CCGCCTGGCT GACCGCTCAA CGACCCCCGC
                                                                4800
CCATTGACGT CAATAATGAC GTATGTTCCC ATAGTAACGC CAATAGGGAC TTTCCATTGA
                                                                4860
CGTCAATGGG TGGACTATTT ACGGTAAACT GCCCACTTGG CAGTACATCA AGTGTATCAT
                                                                4920
ATGCCAAGTA CGCCCCCTAT TGACGTCAAT GACGGTAAAT GGCCCGCCTG GCATTATGCC
                                                                4980
CAGTACATGA CCTTATGGGA CTTTCCTACT TGGCAGTACA TCTACGTATT AGTCATCGCT
                                                                5040
ATTACCATGG TGATGCGGTT TTGGCAGTAC ATCAATGGGC GTGGATAGCG GTTTGACTCA
                                                                5100
CGGGGATTTC CAAGTCTCCA CCCCATTGAC GTCAATGGGA GTTTGTTTTG AAGCTTGGCC
                                                                5160
GGCCATATAA ACGGGGGCCA GCTTTATTTA ACGTGTTTAC GTCGAGTCAA TTGTACACTA
                                                                5220
ACGACAGTGA TGAAAGAAAT ACAAAAGCGC ATAATATTTT GAACGACGTC GAACCTTTAT
                                                                5280
```

FIG. 7I

```
TACAAAACAA AACACAAACG AATATCGACA AAGCTAGATT GCTGCTACAA GATTTGGCAA
                                                                5340
GTTTGTGGC GTTGAGCGAA AATCCATTAG ATAGTCCAGC CATCGGTTCG GAAAAACAAC
                                                                5400
CCTTGTTTGA AACTAATCGA AACCTATTTT ACAAATCTAT TGAGGATTTA ATATTTAAAT
                                                                5460
TCAGATATAA AGACGCTGAA AATCATTTGA TTTTCGCTCT AACATACCAC CCTAAAGATT
                                                                5520
ATAAATTTAA TGAATTATTA AAATACATCA GCAACTATAT ATTGATAGAC ATTTCCAGTT
                                                                5580
TGTGATATTA GTTTGTGCGT CTCATTACAA TGGCTGTTAT TTTTAACAAC AAACAACTGC
                                                                5640
TCGCAGACAA TAGTATAGAA AAGGGAGGTG AACTGTTTTT GTTAACGGT TCGTACAACA
                                                                5700
TTTTGGAAAG TTATGTTAAT CCGGTGCTGC TAAAAAATGG TGTAATTGAA CTAGAAGAAG
                                                                5760
CTGCGTACTA TGCCGGGCAAC ATATTGTACA AAACCGACGA TCCCAAATTC ATTGATTATA
                                                                5820
TAAATTTAAT AATTAAAGCA ACACACTCCG AAGAACTACC AGAAAATAGC ACTGTTGTAA
                                                                5880
ATTACAGAAA AACTATGCGC AGCGGTACTA TACACCCCAT TAAAAAAGAC ATATATATTT
                                                                5940
```

FIG. 7J

```
ATGACAACAA AAAATTACT CTATACGATA GATACATATA TGGATACGAT AATAACTATG
                                                                6000
TTAATTTTA TGAGGAGAAA AATGAAAAAG AGAAGGAATA CGAAGAAGAA GACGACAAGG
                                                                6060
CGTCTAGTTT ATGTGAAAAT AAAATTATAT TGTCGCAAAT TAACTGTGAA TCATTTGAAA
                                                                6120
ATGATTTTAA ATATTACCTC AGCGATTATA ACTACGCGTT TTCAATTATA GATAACACTA
                                                                6180
CAAATGTTCT TGTTGCCGTTT GGTTTGTATC GTTAATAAAA AACAAATTTA GCATTTATAA
                                                                6240
TTGTTTTATT ATTCAATAAT TACAAATAGG ATTGAGACCC TTGCAGTTGC CAGCAAACGG
                                                                6300
ACAGAGCTTG TCGAGGAGAG TTGTTGATTC ATTGTTTGCC TCCCTGCTGC GGTTTTTGAC
                                                                6360
CGAAGTTCAT GCCAGTCCAG CGTTTTGCA GCAGAAAAGC CGCCGACTTC GGTTTGCGGT
                                                                6420
CGCCGAGTGAA GATCCCTTTC TTGTTACCGC CAACGCGCAA TATGCCTTGC GAGGTCGCAA
                                                                6480
AATCGGCGAA ATTCCATACC TGTTCACCGA CGACGGCGCT GACGCGGATCA AAGACGCGGT
                                                                6540
GATACATATC CAGCCATGCA CACTGATACT CTTCACTCCA CATGTCGGTG TACATTGAGT
                                                                6600
```

FIG. 7K

```
GCAGCCCGGC TAACGTATCC ACGCCGTATT CGGTGATGAT AATCGGGCTGA TGCAGTTTCT
                                                                  6660
CCTGCCAGGC CAGAAGTTCT TTTTCCAGTA CCTTCTCTGC CGTTTCCAAA TCGCCGCTTT
                                                                  6720
GGACATACCA TCCGTAATAA CGGTTCAGGC ACAGCACATC AAAGAGATCG CTGATGGTAT
                                                                  6780
CGGTGTGAGC GTCGCAGAAC ATTACATTGA CGCAGGTGAT CGGACGCGTC GGGTCGAGTT
                                                                  6840
TACGCGGTTGC TTCCGCCAGT GGCGCGAAAT ATTCCCGTGC ACCTTGCGGA CGGGTATCCG
                                                                  6900
GTTCGTTGGC AATACTCCAC ATCACCACGC TTGGGTGGTT TTTGTCACGC GCTATCAGCT
                                                                  6960
CTTTAATCGC CTGTAAGTGC GCTTCGGTGT TTCCCCGTT GACTGCCTCT TCGTTGTACA
                                                                  7020
GTTCTTTCGG CTGTTGCCCC GCTTCGAAAC CAATGCCTAA AGAGAGGTTA AAGCCGACAG
                                                                  7080
CAGCAGTTTC ATCAATCACC ACGATGCCAT GTTCATCTGC CCAGTCGAGC ATCTCTTCAG
                                                                  7140
CGTAAGGGTA ATGCGAGGTA CGGTAGGAGT TGGCCCTAAT CCAGTCCATT AATGCGTGGT
                                                                  7200
CGTGCACCAT CAGCACGTTA TCGAATCCTT TGCCACGCAA GTCCGCATCT TCATGACGAC
                                                                  7260
```

FIG. 7L

```
CAAAGCCAGT AAAGTAGAAC GGTTGTGGT TAATCAGGAA CTGTTCGCCC TTCACTGCCA
                                                                7320
CTGACCGGAT GCCGACGGCGA AGCGGGTAGA TATCACACTC TGTCTGGCTT TTGGCTGTGA
                                                                7380
CGCACAGTTC ATAGAGATAA CCTTCACCCG GTTGCCAGAG GTGCCGGATTC ACCACTTGCA
                                                                7440
AAGTCCCGCT AGTGCCTTGT CCAGTTGCAA CCACCTGTTG ATCCGCATCA CGCAGTTCAA
                                                                7500
CGCTGACATC ACCACCTGCC AGTCAACAGA CGCGTGGTTA CAGTCTTGCG
                                                                7560
CGACATGCGT CACTACGGTG ATATCGTCCA CCCAGGTGTT CGGGCGTGGTG TAGAGCATTA
                                                                7620
CGCTGCGATG GATTCCGGCA TAGTTAAAGA AATCATGGAA GTAAGATTGC TTTTTCTTGC
                                                                7680
CGTTTTCGTT GGTAATCACC ATTCCCGGCG GGATAGTCTG CCAGTTCAGT TCGTTGTTCA
                                                                7740
CACAAACGGT GATACCCCTC GACGGATTAA AGACTTCAAG CGGTCAACTA TGAAGAAGTG
                                                                7800
TTCGTCTTCG TCCCAGTAAG CTATGTCTCT AGAATGTAGC CATCCATCCT TGTCAATCAA
                                                                7860
GGCGTTGGTC GCTTCCCGGAT TGTTTACATA ACCGGACATA ATCATAGGTC CTCTGACACA
                                                                7920
```

FIG. 7M

```
TAATACGCCT CTCTGATTAA CGCCCAGGCGT TTCCCGGTA TCCAGATCCA CAACCTTCGC
                                                                7980
TTCAAAAAAT GGAACAACTT TACCGACCGC GCCCGGTTTA TCATCCCCCT CGGGTGTAAT
                                                                8040
CAGAATAGCT GATGTAGTCT CAGTGAGCCC ATATCCTTGT CGTATCCCTG GAAGATGGAA
                                                                8100
GCGTTTTGCA ACCGCTTCCC CGACTTCTTT CGAAAGAGGT GCGCCCCCAG AAGCAATTTC
                                                                8160
GTGTAAATTA GATAAATCGT ATTTGTCAAT CAGAGTGCTT TTGGCGAAGA ATGAAAATAG
                                                                8220
GGTTGGGTACT AGCAACGCAC TTTGAATTTT GTAATCCTGA AGGGATCGTA AAAACAGCTC
                                                                8280
TTCTTCAAAT CTATACATTA AGACGACTCG AAATCTACAT ATCAAATATC CGAGTGTAGT
                                                                8340
AAACATTCCA AAACCGTGAT GGAATGGAAC AACACTTAAA ATCGCAGTAT CCGGAATGAT
                                                                8400
TTGATTGCCA AAAATAGGAT CTCTGGCATG CGAGAATCTA GCGCAGGCAG TTCTATGCGG
                                                                8460
AAGGGCCACA CCCTTAGGTA ACCCAGTAGA TCCAGAGGAA TTGTTTTGTC ACGATCAAAG
                                                                8520
GACTCTGGTA CAAAATCGTA TTCATTAAAA CCGGGAGGTA GATGAGATGT GACGAAGGTG
                                                                8580
```

FIG. 7N

```
TACATCGACT GAAATCCCTG GTAATCCGTT TTAGAATCCA TGATAATAAT TTTCTGGATT
                                                                8640
ATTGGTAATT TTTTTGCAC  GTTCAAAATT TTTTGCAACC CCTTTTTGGA AACAAACACT
                                                                8700
ACGGTAGGCT GCGAAATGTT CATACTGTTG AGCAATTCAC GTTCATTATA AATGTCGTTC
                                                                8760
GCGGGGCGCAA CTGCAACTCC GATAAATAAC GCGCCCAACA CCGGCATAAA GAATTGAAGA
                                                                8820
GAGTTTTCAC TGCATACGAC GATTCTGTGA TTTGTATTCA GCCCATATCG TTTCATAGCT
                                                                8880
TCTGCCAACC GAACGGACAT TTCGAAGTAT TCCGCGTACG TGATGTTCAC CTCGATATGT
                                                                8940
GCATCTGTAA AAGGAATTGT TCCAGGAACC AGGGCGTATC TCTTCATAGC CTTATGCAGT
                                                                9000
TGCTCTCCAG CGGTTCCATT CTCTAGCTTT GCTTCTCAAT TTCTTATTTG CATAATGAGA
                                                                9060
AAAAAAGGAA AATTAATTTT AACACCAATT CAGTAGTTGA TTGAGCAAAT GCGTTGCCAA
                                                                9120
AAAGGATGCT TTAGAGACAG TGTTCTCTGC ACAGATAAGG ACAAACATCA TTCAGAGGGA
                                                                9180
GTACCCAGAG CTGAGACTCC TAAGCCAGTG AGTGGCACAG CATTCTAGGG AGAAATATGC
                                                                9240
```

FIG. 7P

```
TTGTCATCAC CGAAGCCTGA TTCCGTAGAG CCACACCTTG GTAAGGGCCA ATCTGCTCAC    9300
ACAGGATAGA GAGGGCAGGA GCCAGGGCAG AGCATATAAG GTGAGGTAGG ATCAGTTGCT    9360
CCTCACATTT GCTTCTGACA TAGTTGTGTT GGGAGCTTGG ATCGATCCAC CATGGGCTTC    9420
AATACCCTGA TTGACTGGAA CAGCTGTAGC CCTGAACAGC AGCGTGCGCT GCTGACGCGT    9480
CCGGCGATTT CCGCCCTCTGA CAGTATTACC CGGACGGTCA GCGATATTCT GGATAATGCA    9540
AAAACGCGCG GTGACGATGC CCTGCGTGAA TACAGCGCTA AATTTGATAA AACAGAAGTG    9600
ACAGGCTAC GCGTCACCCC TGAAGAGATC GCCGCCGCCG GCGGCGGTCT GAGCGACGAA    9660
TTAAAACAGG CGATGACCGC TGCCGTCAAA AATATTGAAA CGTTCCATTC CGGCAGACG    9720
CTACCGCTTG TAGATGTGGA AACCCAGCCA GGCGTGCGTT GCCAGCAGGT TACGCGTCCC    9780
GTCTCGTCTG TCGGTCTGTA TATTCCCGGC GGCTCGGCTC CGCTCTTCTC AACGGTGCTG    9840
ATGTGGGCGA CGCCGGGCCG CATTGCGGGA TGCTAGAAGG TGGTTCTGTG CTCGCCGCCG    9900
```

FIG. 7Q

```
CCCATCGCTG ATGAAATCCT CTATGCGGCG CAACTGTGTG GCGTGCAGGA ATTCTTTAAC
                                                                9960
CTCGGCGGCG CGCAGGCGAT TGCCGCTCTG GCCTTCGGCA GCGAGTCCGT ACCGAAAGTG
                                                               10020
GATAAAATTT TGGCCCCCGG CAACGCCTTT GTAACCGAAG CCAAACGTCA GGTCAGCCAG
                                                               10080
CGTCTCGACG GCGCGGGCTA TCGATATGCCA GCCGAGCCGT CTGAAGTACT GGTGATCGCA
                                                               10140
GACAGCGGGCG CAACACCGGA TTTCGTCGCT TCTCCCAGAC TGAGCACGGC
                                                               10200
CCGGATTCCC AGGTGATCCT GCTGACGCCT GATGCTGACA TTGCCCGCAA GGTGGCGGAG
                                                               10260
GCGGTAGAAC GTCAACTGGC GGAACTGCCG CGGCGGGACA CCGCCCTGGCA GGCCCTGAGC
                                                               10320
GCCAGTCGTC TGATTGTGAC CAAAGATTTA GCGCAGTGCG TCGCCATCTC TAATCAGTAT
                                                               10380
GGGCCGGAAC ACTTAATCAT CCAGACGCGC AATGCGCGCG ATTTGGTGGA TGCGATTACC
                                                               10440
AGCGCAGGCT CGGTATTTCT CGGCGACTGG TCGCCCGGAAT CCGCCGGTGA TTACGCTTCC
                                                               10500
GGAACCAACC ATGTTTTACC GACCTATGGC CATACTGCTA CCTGTTCCAG CCTTGGGTTA
                                                               10560
```

FIG. 7R

| | | | | |
|---|---|---|---|---|
|GCGGATTCC|AGAAACGGAT|GACCGTTCAG|GAACTGTCGA|AAGCGGGCTT|TTCCGCTCTG 10620|
|GCATCAACCA|TTGAAACATT|GGCGGGGGCA|GAACGTCTGA|CCGCCCATAA|AAATGCCGTG 10680|
|ACCCTGCGCG|TAAACGCCCT|CAAGGAGCAA|GCATGAGCAC|TGAAAACACT|CTCAGCGTCG 10740|
|CTGACTTAGC|CCGTGAAAAT|GTCCGCAACC|CTAGAATGCA|GACATGATAA|GATACATTGA 10800|
|TGAGTTTGGA|CAAACCACAA|CTAGAATGCA|GTGAAAAAAA|TGCTTTATTT|GTGAAATTTG 10860|
|TGATGCTATT|GCTTTATTTG|TAACCATTAT|AAGCTGCAAT|AAACAAGTTA|ACAACAACAA 10920|
|TTGCATTCAT|TTTATGTTTC|AGGTTCAGGG|GGAGGTGTGG|GAGGTTTTTT|AAAGCAAGTA 10980|
|AAACCTCTAC|AAATGTGGTA|TGGCTGATTA|TGATCTCTAG|CTCGACGGGG|CGCCTGGCCG 11040|
|CTACTAACTC|TCTCCTCCCT|CCTTTTTCCT|GCAGGCTCAA|GGCGCGGCAT|CCCGACGGCG 11100|
|AGGATCTCGT|CGTGACCCAT|GGCGATGCCT|GCTTGCCGAA|TATCATGGTG|GAAAATGGCC 11160|
|GCTTTTCTGG|ATTCATCGAC|TGTGGCCGGC|TGGGTGTGGC|GGACCGCTAT|CAGGACATAG 11220|

FIG. 7S

```
CGTTGGCTAC CCGTGATATT GCTGAAGAGC TTGGGGGCGA ATGGGCTGAC CGCTTCCTCG   11280
TGCTTTACGG TATCGCCGCT CCCGATTCGC AGCGCATCGC CTTCTTGACG              11340
AGTTCTCTG  AGCGGGACTC TGGGGTTCGA AATGACCGAC CAAGCGACGC CCAACCTGCC   11400
ATCACGAGAT TTCGATTCCA CCGCCGCCTT CTATGAAAGG TTGGGCTTCG GAATCGTTTT   11460
CCGGGACGCC GGCTGGATGA TCCTCCAGCG CGGGGATCTC ATGCTGGAGT TCTTCGCCCA   11520
CCCCAACTTG TTTATTGCAG CTTATAATGG TTACAAATAA AGCAATAGCA TCACAAATTT   11580
CACAAATAAA GCATTTTTTT CACTGCATTC TAGTTGTGGT TTGTCCAAAC TCATCAATCT   11640
ATCTTATCAT GTCTGGATCG CGGCCGGTCT CTCTCTAGCC CTAGGTCTAG ACTTGGCAGA   11700
ACATATCCAT CGCGTCCGCC ATCTCCAGCA GCCGCACGCG GCGCATCTCG GGCAGCCGTTG  11760
GGTCCTGGCC ACGGGTGCGC ATGATCGTGC TCCTGTCGTT GAGGACCCGG CTAGGCTGGC   11820
GGGGTTGCCT TACTGGTTAG CAGAATGAAT CACCGATACG CGAGCGAACG TGAAGCGACT   11880
```

FIG. 7T

```
GCTGCTGCAA AACGTCTGCG ACCTGAGCAA CAACATGAAT GGTCTTCGGT TTCCGTGTTT
                                                                  11940
CGTAAAGTCT GGAAACGCGG AAGTCAGCGC CCTGCACCAT TATGTTCCGG ATCTGCATCG
                                                                  12000
CAGGATGCTG CTGGCTACCC TGTGGAACAC CTACATCTGT ATTAACGAAG CGCTGGCATT
                                                                  12060
GACCCTGAGT GATTTTCTC TGGTCCCGCC GCATCCATAC CGCCAGTGT TTACCCTCAC
                                                                  12120
AACGTTCCAG TAACCGGGCA TGTTCATCAT CAGTAACCCG TATCGTGAGC ATCCTCTCTC
                                                                  12180
GTTTCATCGG TATCATTACC CCATGAACA GAAATCCCCC TTAACGGAG GCATCAGTGA
                                                                  12240
CCAAACAGGA AAAAACCGCC CTTAACATGG CCCGCTTTAT CAGAAGCCAG ACATTAACGC
                                                                  12300
TTCTGGAGAA ACTCAACGAG CTGGACGCGG ATGAACAGGC AGACATCTGT GAATCGCTTC
                                                                  12360
ACGACCACGC TGATGAGCTT TACCGCAGCT GCCTCGCGCG TTTCGGTGAT GACGGTGAAA
                                                                  12420
ACCTCTGACA CATGCAGCTC CCGGAGACGG TCACAGCTTG TCTGTAAGCG GATGCCGGGA
                                                                  12480
GCAGACAAGC CCGTCAGGGC GCGTCAGCGG GTGTTGGGCGG GTGTCGGGGC GCAGCCATGA
                                                                  12540
```

FIG. 7U

```
CCCAGTCACG TAGCGATAGC GGAGTGTATA CTGGCTTAAC TATGCGGCAT CAGAGCAGAT
                                                                12600
TGTACTGAGA GTGCACCATA TGCGGTGTGA AATACCGCAC AGATGCGTAA GGAGAAAATA
                                                                12660
CCGCATCAGG CGCTCTTCCG CTTCCTCGCT CACTGACTCG CTGCGCTCCG TCGTTCGGCT
                                                                12720
GCGGGCGAGCG GTATCAGCTC ACTCAAAGGC GGTAATACGG TTATCCACAG AATCAGGGGA
                                                                12780
TAACGCAGGA AGAACATGT GAGCAAAAGG CCAGCAAAAG GCCAGGAACC GTAAAAAGGC
                                                                12840
CGCGTTGCTG GCGTTTTTCC ATAGGCTCCG CCCCCCTGAC GAGCATCACA AAAATCGACG
                                                                12900
CTCAAGTCAG AGGTGGCGAA ACCCGACAGG ACTATAAAGA TACCAGGCGT TTCCCCCTGG
                                                                12960
AAGCTCCCTC GTGCGCTCTC CTGTTCCGAC CGCTTTCTCA TAGCTCACGC TGTCCGCCTT
                                                                13020
TCTCCCTTCG GGAAGCGTGG CGCTTTCTCA TAGCTCACGC TGTAGGTATC TCAGTTCGGT
                                                                13080
GTAGGTCGTT CGCTCCAAGC TGGGCTGTGT GCACGAACCC CCGTTCAGC CCGACCGCTG
                                                                13140
CGCCTTATCC GGTAACTATC GTCTTGAGTC CAACCCGGTA AGACACGACT TATCGCCACT
                                                                13200
```

FIG. 7V

```
GGCAGCAGCC ACTGGTAACA GGATTAGCAG AGCGAGGTAT GTAGGCGGTG CTACAGAGTT
                                                                13260
CTTGAAGTGG TGGCCTAACT ACGGCTACAC TAGAAGGACA GTATTTGGTA TCTGCGCTCT
                                                                13320
GCTGAAGCCA GTTACCTTCG GAAAAAGAGT TGGTAGCTCT TGATCCGGCA AACAAACCAC
                                                                13380
CGCTGGTAGC GGTGGTTTTT TTGTTTGCAA GCAGCAGATT ACGCGCAGAA AAAAAGGATC
                                                                13440
TCAAGAAGAT CCTTTGATCT TTTCTACGGG GTCTGACGCT CAGTGGAACG AAAACTCACG
                                                                13500
TTAAGGGATT TTGGTCATGA GATTATCAAA AAGGATCTTC ACCTAGATCC TTTTAAATTA
                                                                13560
AAAATGAAGT TTTAAATCAA TCTAAAGTAT ATATGAGTAA ACTTGGTCTG ACAGTTACCA
                                                                13620
ATGCTTAATC AGTGAGGCAC CTATCTCAGC GATCTGTCTA TTTCGTTCAT CCATAGTTGC
                                                                13680
CTGACTCCCC GTCGTGTAGA TAACTACGAT ACGGGAGGGC TTACCATCTG GCCCCAGTGC
                                                                13740
TGCAATGATA CCGCGAGACC CACGCTCACC GGCTCCAGAT TTATCAGCAA TAAACCAGCC
                                                                13800
AGCCGGAAGG GCCGAGCGCA GAAGTGGTCC TGCAACTTTA TCCGCCTCCA TCCAGTCTAT
                                                                13860
```

FIG. 7W

```
TAATTGTTGC CGGGAAGCTA GAGTAAGTAG TTCGCCAGTT AATAGTTTGC GCAACGTTGT   13920
TGCCATTGCT GCAGGCATCG TGGTGTCACG CTCGTCGTTT GGTATGGCTT CATTCAGCTC   13980
CGGTTCCCAA CGATCAAGGC GAGTTACATG ATCCCCCATG TTGTGCAAAA AAGCGGTTAG   14040
CTCCTTCGGT CCTCCGATCG TTGTCAGAAG TAAGTTGGCC GCAGTGTTAT CACTCCATGGT 14100
TATGGCAGCA CTGCATAATT CTCTTACTGT CATTCTGAGA ATAGTGTATG CGGCGACCGA GTTGCTCTTG   14220
TGGTGAGTAC TCAACCAAGT CATTCTGAGA ATAGTGTATG CGGCGACCGA GTTGCTCTTG   14220
CCCGGCGTCA ACACGGGATA ATACCGCGCC ACATAGCAGA ACTTTAAAAG TGCTCATCAT   14280
TGGAAAACGT TCTTCGGGGC GAAAACTCTC AAGGATCTTA CCGCTGTTGA GATCCAGTTC   14340
GATGTAACCC ACTCGTGCAC CCAACTGATC TTCAGCATCT TTTACTTTCA CCAGCGTTTC   14400
TGGGTGAGCA AAAACAGGAA GGCAAAATGC CGCAAAAAAG GGAATAAGGG CGACACGGAA   14460
ATGTTGAATA CTCATACTCT TCCTTTTTCA ATATTATTGA AGCATTTATC AGGGTTATTG   14520
```

FIG. 7X

```
TCTCATGAGC GGATACATAT TTGAATGTAT TTAGAAAAAT AACAAATAG GGGTTCCGCG 14580
CACATTTCCC CGAAAAGTGC CACCTGACGT CTAAGAAACC ATTATTATCA TGACATTAAC 14640
CTATAAAAAT AGGCGTATCA CGAGGCCCTT TCGTCTTCAA GAA                  14683
```

FIG. 8A

| | |
|---|---|
| TTAATTAAGG GGCGGAGAAT GGGCGGAACT GGGCGGGAGTT AGGGGCGGGA TGGGCGGAGT | 60 |
| TAGGGGCGGG ACTATGGTTG CTGACTAATT GAGATGCATG CTTTGCATAC TTCTGCCTGC | 120 |
| TGGGGAGCCT GGGGACTTTC CACACCTGGT TGCTGACTAA TTGAGATGCA TGCTTTGCAT | 180 |
| ACTTCTGCCT GCTGGGGAGC CTGGGGGACTT TCCACACCCT AACTGACACA CATTCCACAG | 240 |
| AATTAATTCC CCTAGTTATT AATAGTAATC AATTACGGGG TCATTAGGTC ATAGCCCATA | 300 |
| TATGGAGTTC CGCGTTACAT AACTTACGGT AAATGGCCCG CCTGGCTGAC CGCCCAACGA | 360 |
| CCCCGCCCA TTGACGTCAA TAATGACGTA TGTTCCCATA GTAACGCCAA TAGGGACTTT | 420 |
| CCATTGACGT CAATGGGTGG ACTATTTACG GTAAACTGCC CACTTGGCAG TACATCAAGT | 480 |
| GTATCATATG CCAAGTACGC CCCCTATTGA CGTCAATGAC GGTAAATGGC CCGCCTGGCA | 540 |
| TTATGCCCAG TACATGACCT TATGGGACTT TCCTACTTGG CAGTACATCT ACGTATTAGT | 600 |
| CATCGCTATT ACCATGGTGA TGCGGTTTTG GCAGTACATC AATGGGCGTG GATAGCGGTT | 660 |
| TGACTCACGG GGATTTCCAA GTCTCCACCC CATTGACGTC AATGGGAGTT TGTTTTGAAG | 720 |
| CTTGGCCGGC CATATAAACG GGGCCAGCT TTATTAACG TGTTTACGTC GAGTCAATTG | 780 |
| TACACTAACG ACAGTGATGA AAGAAATACA AAGCGCATA ATATTTTGAA CGACGTCGAA | 840 |

FIG. 8B

```
CCTTTATTAC AAAACAAAAC ACAAACGAAT ATCGACAAAG CTAGATTGCT GCTACAAGAT    900
TTGGCAAGTT TTGTGGCGTT GAGCGAAAAT CCATTAGATA GTCCAGCCAT CGGTTCGGAA    960
AAACAACCCT TGTTTGAAAC TAATCGAAAC CTATTTTACA AATCTATTGA GGATTTAATA   1020
TTTAAATTCA GATATAAAGA CGCTGAAAAT CATTTGATTT TCGCTCTAAC ATACCACCCT   1080
AAAGATTATA AATTTAATGA ATTATTAAAA TACATCAGCA ACTATATATT GATAGACATT   1140
TCCAGTTTGT GATATTAGTT TGTGCGTCTC ATTACAATGG CTGTTATTTT TAACAACAAA   1200
CAACTGCTCG CAGACAATAG TATAGAAAAG GGAGGTGAAC TGTTTTTGTT TAACGGTTCG   1260
TACAACATTT TGGAAAGTTA TGTTAATCCG GTGCTGCTAA AAAATGGTGT AATTGAACTA   1320
GAAGAAGCTG CGTACTATGC CGGCAACATA TTGTACAAAA CCGACGATCC CAAATTCATT   1380
GATTATATAA ATTAATAAT TAAAGCAACA CACTCCGAAG AACTACCAGA AAATAGCACT   1440
GTTGTAAATT ACAGAAAAAC TATGCGCAGC GGTACTATAC ACCCCATTAA AAAAGACATA   1500
TATATTTATG ACAACAAAAA ATTTACTCTA TACGATAGAT ACATATATGG ATACGATAAT   1560
AACTATGTTA ATTTTATGA GGAGAAAAAT GAAAAAGAGA AGGAATACGA AGAAGAAGAC   1620
GACAAGGCGT CTAGTTTATG TGAAAATAAA ATTATATTGT CGCAAATTAA CTGTGAATCA   1680
```

FIG. 8C

```
TTTGAAAATG ATTTAAATA TTACCTCAGC GATTATAACT ACGCGTTTTC AATTATAGAT   1740
AATACTACAA ATGTTCTTGT TGCGTTTGGT TTGTATCGTT AATAAAAAAC AAATTTAGCA   1800
TTTATAATTG TTTTATTATT CAATAATTAC AAATAGGATT GAGACCCTTG CAGTTGCCAG   1860
CAAACGGACA GAGCTTGTCG AGGAGAGTTG TTGATTCATT GTTTGCCTCC CTGCTGCGGT   1920
TTTTCACCGA AGTTCATGCC AGTCCAGCGT TTTTGCAGCA GAAAAGCCGC CGACTTCGGT   1980
TTGCGGTCGC GAGTGAAGAT CCCTTTCTTG TTACCGCCAA CGGCGCTGAC GCCTTGCGAG   2040
GTCGCAAAAT CGGCGAAATT CCATACCTGT TCACCGACGA CGGCGCTGAC GCGATCAAAG   2100
ACGCGGTGAT ACATATCCAG CCATGCACAC TGATACTCTT CACTCCACAT GTCGGTGTAC   2160
ATTGAGTGCA GCCCGGCTAA CGTATCCACG CCGTATTCGG TGATGATAAT CGGCTGATGC   2220
AGTTCTCCT GCCAGGCCAG AAGTTCTTTT TCCAGTACCT TCTCTGCCGT TTCCAAATCG   2280
CCGCTTTGGA CATACCATCC GTAATAACGG TTCAGGCACA GCACATCAAA GAGATCGCTG   2340
ATGGTATCGG TGTGAGCGTC GCAGAACATT ACATTGACGC AGGTGATCGG ACGCGTCGGG   2400
TCGAGTTTAC GCGTTGCTTC CGCCAGTGGC GCGAAATATT CCCGTGCACC TTGCGGACGG   2460
GTATCCGGTT CGTTGGCAAT ACTCCACATC ACCACGCTTG GGTGGTTTTT GTCACGCGCT   2520
```

FIG. 8D

```
ATCAGCTCTT TAATCGCCTG TAAGTGCGCT TGCTGAGTTT CCCCGTTGAC TGCCTCTTCG 2580
CTGTACAGTT CTTCGGCTT GTTGCCCGCT TCGAAACCAA TGCCTAAAGA GAGGTTAAAG 2640
CCGACAGCAG CAGTTCATC AATCACCACG ATGCCATGTT CATCTGCCCA GTCGAGCATC 2700
TCTTCAGCGT AAGGGTAATG CGAGGTACGG TAGGAGTTGG CCCCAATCCA GTCCATTAAT 2760
GCGTGGTCGT GCACCATCAG CACGTTATCG AATCCTTTGC CACGCAAGTC CGCATCTTCA 2820
TGACGACCAA AGCCAGTAAA GTAGAACGGT TTGTGGTTAA TCAGGAACTG TTCGCCCTTC 2880
ACTGCCACTG ACCGGATGCC GACGCGAAGC GGGTAGATAT CACACTCTGT CTGGCTTTTG 2940
GCTGTGACGC ACAGTTCATA GAGATAACCT TCACCCGGTT GCCAGAGGTG CGGATTCACC 3000
ACTTGCAAAG TCCCGCTAGT GCCTTGTCCA GTTGCAACCA CCTGTTGATC CGCATCACGC 3060
AGTTCAACGC TGACATCACC ATTGGCCACC ACCTGCCAGT CAACAGACGC GTGGTTACAG 3120
TCTTGCGCGA CATGCGTCAC CACGGTGATA TCGTCCACCC AGGTGTTCGG CGTGGTGTAG 3180
AGCATTACGC TGCGGATGGAT TCCGGCATAG TTAAAGAAAT CATGGAAGTA AGACTGCTTT 3240
TTCTTGCCGT TTCGTCGGT AATCACCATT CCCGGCGGGA TAGTCTGCCA GTTCAGTTCG 3300
TTGTTCACAC AAACGGTGAT ACCCCTCGAC GGATTAAAGA CTTCAAGCGG TCAACTATGA 3360
```

FIG. 8E

```
AGAAGTGTTC GTCTTCGTCC CAGTAAGCTA TGTCTCCAGA ATGTAGCCAT CCATCCTTGT  3420
CAATCAAGGC GTTGGTCGCT TCCGGATTGT TTACATAACC GGACATAATC ATAGGTCCTC  3480
TGACACATAA TTCGCCTCTC TGATTAACGC CCAGCGTTTT CCCGGTATCC AGATCCACAA  3540
CCTTCGCTTC AAAAAATGGA ACAACTTTAC CGACCGCGCC CGGTTTATCA TCCCCCTCGG  3600
GTGTAATCAG AATAGCTGAT GTAGTCTCAG TGAGCCCATA TCCTTGTCGT ATCCCTGGAA  3660
GATGGAAGCG TTTTGCAACC GCTTCCCCGA CTTCTTTCGA AAGAGGTGCG CCCCCAGAAG  3720
CAATTTCGTG TAAATTAGAT AAATCGTATT TGTCAATCAG AGTGCTTTTG GCGAAGAATG  3780
AAAATAGGGT TGGTACTAGC AACGCACTTT GAATTTGTA ATCCTGAAGG GATCGTAAAA  3840
ACAGCTCTTC TTCAAATCTA TACATTAAGA CGACTCGAAA TCCACATATC AAATATCCGA  3900
GTGTAGTAAA CATTCCAAAA CCGTGATGGA ATGGAACAAC ACTTAAAATC GCAGTATCCG  3960
GAATGATTTG ATTGCCAAAA ATAGGATCTC TGGCATGCGA GAATCTAGCG CAGGCAGTTC  4020
TATGCGGAAG GGCCACACCC TTAGGTAACC CAGTAGATCC AGAGGAATTG TTTTGTCACG  4080
ATCAAAGGAC TCTGGTACAA AATCGTATTC ATTAAAACCG GGAGGTAGAT GAGATGTGAC  4140
GAACGTGTAC ATCGACTGAA ATCCCTGGTA ATCCGTTTTA GAATCCATGA TAATAATTTT  4200
```

FIG. 8F

```
CTGGATTATT GGTAATTTTT TTGCACGTT CAAAATTTTT TGCAACCCCT TTTGGAAAC    4260
AAACACTACG GTAGGCTGCG AAATGTTCAT ACTGTTGAGC AATTCACGTT CATTATAAAT  4320
GTCGTTCGCG GGCGCAACTG CAACTCCGAT AAATAACGCG CCCAACACCG GCATAAAGAA  4380
TTGAAGAGAG TTTTCACTGC ATACGACGAT TCTGTGATTT GTATTCAGCC CATATCGTTT  4440
CATAGCTTCT GCCAACCGAA CGGACATTTC GAAGTATTCC GCGTACGTGA TGTTCACCTC  4500
GATATGTGCA TCTGTAAAAG GAATTGTTCC AGGAACCAGG GCGTATCTCT TCATAGCCTT  4560
ATGCAGTTGC TCTCCAGCGG TTCCATCCTC TAGCTTGCT TCTCAATTC TTATTTGCAT    4620
AATGAGAAAA AAAGGAAAAT TAATTTTAAC ACCAATTCAG TAGTTGATTG AGCAAATGCG  4680
TTGCCAAAAA GGATGCTTTA GAGACAGTGT TCTCTGCACA GATAAGGACA AACATTATTC  4740
AGAGGGAGTA CCCAGAGCTG AGACTCCTAA GCCAGTGAGT GGCACAGCAT TCTAGGGAGA  4800
AATATGCTTG TCATCACCGA AGCCTGATTC CGTAGAGCCA CACCTTGGTA AGGGCCAATC  4860
TGCTCACACA GGATAGAGAG GGCAGGAGCC AGGGCAGAGC ATATAAGGTG AGGTAGGATC  4920
AGTTGCTCCT CACATTGCT TCTGACATAG TTGTGTTGGG AGCTTGGATC GATCCACCAT   4980
GGGCTTCAAT ACCCTGATTG ACTGGAACAG CTGTAGCCCT GAACAGCAGC GTGCGCTGCT  5040
```

FIG. 8G

```
GACGCGTCCG GCGATTCCG  CCTCTGACAG TATTACCCGG ACGGTCAGCG ATATTCTGGA   5100
TAATGTAAAA ACGCGCGGTG ACGATGCCCT GCGTGAATAC AGCGCTAAAT TTGATAAAAC   5160
AGAAGTGACA GCGCTACGCG TCACCCCTGA AGAGATCGCC GCCGCGGGCG CGGCTCTGAG   5220
CGACGAATTA AAACAGGCGA TGACCGCTGC CGTCAAAAAT ATTGAAACGT TCCATTCCGC   5280
GCAGACGCTA CCGCCTGTAG ATGTGGAAAC CCAGCCAGGC GTGCGTTGCC AGCAGGTTAC   5340
GCGTCCCGTC TCGTCTGTCG GTCTGTATAT TCCCGGGGGC TCGGCTCCGC TCTTCTCAAC   5400
GGTGCTGATG CTGGGCGACGC CGGGCGCGCAT TGCGGGATGC CAGAAGGTGG TTCTGTGCTC   5460
GCCGCCGCCC ATCGCTGATG AAATCCTCTA TGCGGCGCAA CTGTGTGGCG TGCAGGAAAT   5520
CTTTAACGTC GGGGCGGCGC AGGCGATTGC CGCTCTGGCC TTCGGCAGCG AGTCCGTACC   5580
GAAAGTGGAT AAAATTTTTG GCCCCGGGCA CGCCTTTGTA ACCGAAGCCA AACGTCAGGT   5640
CAGCCAGCGT CTCGACGGGG CGGCTATCGA TATGCCAGCC GGGCCGTCTG AAGTACTGGT   5700
GATCGCAGAC AGCGGGCGCAA CACCGGATTT CGTCGCTTCT GACCTGCTCT CCCAGGCTGA   5760
GCACGGGCCCG GATTCCCAGG TGATCCCTGCT GACGCCTGAT GCTGACATTG CCCGCAAGGT   5820
GGCGGAGGCG GTAGAACGTC AACTGGGCGGA ACTGCCGCGC GCGGACACCG CCCGGCAGGC   5880
```

FIG. 8H

```
CCTGAGCGCC AGTCGTCTGA TTGTGACCAA AGATTAGCG CAGTGCCGTCG CCATCTCTAA  5940
TCAGTATGGG CCGGAACACT TAATCATCCA GACGCGCAAT GCGCGCGATT TGGTGGATGC  6000
GATTACCAGC GCAGGCTCGG TATTTCTCGG CGACTGGTCG CCGGAATCCG CCGGTGATTA  6060
CGCTTCCGGA ACCAACCATG TTTTACCGAC CTATGGCTAT ACTGCTACCT GTTCCAGCCT  6120
TGGGTTAGCG GATTCCAGA AACGGATGAC CGTTCAGGAA CTGTCGAAAG CGGGCTTTTC  6180
CGCTCTGGCA TCAACCATTG AAACATTGGC GGCGGCAGAA CGTCTGACCG CCCATAAAAA  6240
TGCCGTGACC CTGCGCGTAA ACGCCCTCAA GGAGCAAGCA TGAGCACTGA AAACACTCTC  6300
AGCGTCGCTG ACTTAGCCCG TGAAAATGTC CGCAACCTGG AGATCCAGAC ATGATAAGAT  6360
ACATTGATGA GTTGGACAA ACCACAACTA GAATGCAGTG AAAAAAATGC TTTATTTGTG  6420
AAATTGTGA TGCTATTGCT TTATTTGTAA CCATTATAAG CTGCAATAAA CAAGTTAACA  6480
ACAACAATTG CATTCATTTT ATGTTTCAGG TTCAGGGGGA GGTGTGGGAG GTTTTTTAAA  6540
GCAAGTAAAA CCCTCTACAA TGTGGTATGG CTGATTATGA TCTCTAGCTC GACGGGGGC  6600
CTCTAGAGCA GTGTGGTTTT GCAAGAGGAA GCAAAAAGCC TCTCCACCCA GGCCTGGAAT  6660
GTTTCCACCC AATGTCGAGC AGTGTGGTTT TGCAAGAGGA AGCAAAAAGC CTCTCCACCC  6720
```

FIG. 8I

```
AGGCCTGGAA TGTTCCACC  CAATGTCGAG CAAACCCCGC CCAGCGTCTT GTCATTGGCG  6780
AATTCGAACA CGCAGATGCA GTCGGGGCGG CGCGGTCCCA GTCCACTTC  GCATATTAAG  6840
GTGACGCGTG TGGCCTCGAA CACCGAGCGA CCCTGCAGCC AATATGGGAT CGGCCATTGA  6900
ACAAGATGGA TTGCACGCAG GTTCTCCGGC CGCTTGGGTG GAGAGGCTAT TCGGCTATGA  6960
CTGGGCACAA CAGACAATCG GCTGCTCTGA TGCCGCCGTG TTCCGGCTGT CAGCGCAGGG  7020
GCGCCCGGTT CTTTTGTCA  AGACCGACCT GTCCGGTGCC CTGAATGAAC TGCAGGTAAG  7080
TGCGGCCGTC GATGGCCGAG GCGGCCTCGG CCTCTGCATA AATAAAAAAA ATTAGTCAGC  7140
CATGCATGGG GCGGAGAATG GGCGGAACTG GGCGGAGTTA GGGGCGGGAT GGGCGGAGTT  7200
AGGGGCGGGA CTATGGTTGC TGACTAATTG AGATGCATGC TTTGCATACT TCTGCCTGCT  7260
GGGGAGCCTG GGGACTTTCC ACACCTGGTT GCTGACTAAT TGAGATGCAT GCTTTGCATA  7320
CTTCTGCCTG CTGGGGAGCC TGGGGACTTT CCACACCCTA ACTGACACAC ATTCCACAGA  7380
ATTAATTCCC CTAGTTATTA ATAGTAATCA ATTACGGGGT CATTAGTTCA TAGCCCATAT  7440
ATGGAGTTCC GCGTTACATA ACTTACGGTA AATGGCCCGC CTGGCTGACC GCCCAACGAC  7500
CCCCGCCCAT TGACGTCAAT AATGACGTAT GTTCCCATAG TAACGCCAAT AGGGACTTTC  7560
```

FIG. 8J

```
CATTGACGTC AATGGGTGGA CTATTACGG TAAACTGCCC ACTTGGCAGT ACATCAAGTG  7620
TATCATATGC CAAGTACGCC CCCTATTGAC GTCAATGACG GTAAATGGCC CGCCTGGCAT  7680
TATGCCCAGT ACATGACCTT ATGGGACTTT CCTACTTGGC AGTACATCTA GCTATTAGTC  7740
ATCGCTATTA CCATGGTGAT GCGGTTTTGG CAGTACATCA ATGGGCGTGG ATAGCGGTTT  7800
GACTCACGGG GATTTCCAAG TCTCCACCCC ATTGACGTCA ATGGGAGTTT GTTTTGGCAC  7860
CAAAATCAAC GGGACTTTCC AAAATGTCGT AACAACTCCG CCCCATTGAC GCAAATGGGC  7920
GGTAGGCGTG TACGGTGGGA GGTCTATATA AGCAGAGCTG GGTACGTGAA CCGTCAGATC  7980
GCCTGGAGAC GCCATCACAG ATCTCTCACT ATGGATTTTC AGGTGCAGAT TATCAGCTTC  8040
CTGCTAATCA GTGCTTCAGT CATAATGTCC AGAGGACAAA TTGTTCTCTC CCAGTCTCCA  8100
GCAATCCTGT CTGCATCTCC AGGGGAGAAG GTCACAATGA CTTGCAGGGC CAGCTCAAGT  8160
GTAAGTTACA TCCACTGGTT CCAGCAGAAG CCAGGATCCT CCCCCAAACC CTGGATTTAT  8220
GCCACATCCA ACCTGGCTTC TGGAGTCCCT GTTCGCTTCA GTGGCAGTGG GTCTGGGACT  8280
TCTTACTCTC TCACAATCAG CAGAGTGGAG GCTGAAGATG CTGCCACTTA TTACTGCCAG  8340
CAGTGGACTA GTAACCCACC CACGTTCGGA GGGGGGACCA AGCTGGAAAT CAAACGTACG  8400
```

FIG. 8K

| | | | | |
|---|---|---|---|---|
| GTGGCTGCAC | CATCTGTCTT | CATCTTCCCG | CCATCTGATG AGCAGTTGAA | ATCTGGAACT 8460 |
| GCCTCTGTTG | TGTGCCTGCT | GAATAACTTC | TATCCCAGAG AGGCCAAAGT | ACAGTGGAAG 8520 |
| GTGGATAACG | CCCTCCAATC | GGGTAACTCC | CAGGAGAGTG TCACAGAGCA | GGACAGCAAG 8580 |
| GACAGCACCT | ACAGCCTCAG | CAGCACCCTG | ACGCTGAGCA AAGCAGACTA | CGAGAAACAC 8640 |
| AAAGTCTACG | CCTGCGAAGT | CACCCATCAG | GGCCTGAGCT CGCCCGTCAC | AAAGAGCTTC 8700 |
| AACAGGGGAG | AGTGTTGAAT | TCAGATCCGT | TAACGGTTAC CAACTACCTA | GACTGGATTC 8760 |
| GTGACAACAT | GCGGCCGTGA | TATCTACGTA | TGATCAGCCT CGACTGTGCC | TTCTAGTTGC 8820 |
| CAGCCATCTG | TTGTTTGCCC | CTCCCCCGTG | CCTTCCTTGA CCCTGGAAGG | TGCCACTCCC 8880 |
| ACTGTCCTTT | CCTAATAAAA | TGAGGAAATT | GCATCGCATT GTCTGAGTAG | GTGTCATTCT 8940 |
| ATTCTGGGGG | GTGGGGTGGG | GCAGGACAGC | AAGGGGGAGG ATTGGGAAGA | CAATAGCAGG 9000 |
| CATGCTGGGG | ATGCGGTGGG | CTCTATGGAA | CCAGCTGGGG CTCGACAGCT | ATGCCAAGTA 9060 |
| CGCCCCCTAT | TGACGTCAAT | GACGGTAAAT | GGCCCGCCTG GCATTATGCC | CAGTACATGA 9120 |
| CCTTATGGGA | CTTTCCTACT | TGGCAGTACA | TCTACGTATT AGTCATCGCT | ATTACCATGG 9180 |
| TGATGCGGTT | TTGGCAGTAC | ATCAATGGGC | GTGGATAGCG GTTTGACTCA | CGGGGATTTC 9240 |

FIG. 8L

```
CAAGTCTCCA CCCCATTGAC GTCAATGGGA GTTGTTTTG GCACCAAAAT CAACGGGACT  9300
TTCCAAAATG TCGTAACAAC TCCGCCCCAT TGACGCAAAT GGGCGGTAGG CGTGTACGGT  9360
GGGAGGTCTA TATAAGCAGA GCTGGGTACG TCCTCACATT CAGTGATCAG CACTGAACAC  9420
AGACCCGTCG ACATGGGTG GAGCCTCATC TTGCTCTTCC TTGTCGCTGT TGCTACGCGT  9480
GTCCTGTCCC AGGTACAACT GCAGCAGCCT GGGGCTGAGC TGGTGAAGCC TGGGGCCTCA  9540
GTGAAGATGT CCTGCAAGGC TTCTGGCTAC ACATTACCA GTTACAATAT GCACTGGGTA  9600
AAACAGACAC CTGGTCGGGG CCTGGAATGG ATTGGGAGCTA TTTATCCCGG AAATGGTGAT  9660
ACTTCCTACA ATCAGAAGTT CAAAGGCAAG GCCACATTGA CTGCAGACAA ATCCTCCAGC  9720
ACAGCCTACA TGCAGCTCAG CAGCCTGACA TCTGAGGACT CTGCGGTCTA TTACTGTGCA  9780
AGATCGACTT ACTACGGCGG TGACTGGTAC TTCAATGTCT GGGGCGCAGG GACCACGGTC  9840
ACCGTCTCTG CAGCTAGCAC CAAGGGCCCA TCGGTCTTCC CCCTGGCACC CTCCTCCAAG  9900
AGCACCTCTG GGGGCACAGC GGCCCTGGGC TGCCTGGTCA AGGACTACTT CCCCGAACCG  9960
GTGACGGTGT CGTGGAACTC AGGCGCCCTG ACCAGCGGCG TGCACACCTT CCCGGCTGTC 10020
CTACAGTCCT CAGGACTCTA CTCCCTCAGC AGCGTGGTGA CCGTGCCCTC CAGCAGCTTG 10080
```

FIG. 8M

```
GGCACCCAGA CCTACATCTG CAACGTGAAT CACAAGCCCA GCAACACCAA GGTGGACAAG  10140
AAAGCAGAGC CCAAATCTTG TGACAAAACT CACACATGCC CACCGTGCCC AGCACCTGAA  10200
CTCCTGGGGG GACCGTCAGT CTTCCTCTTC CCCCCAAAAC CCAAGGACAC CCTCATGATC  10260
TCCCGGACCC CTGAGGTCAC ATGCGTGGTG GTGGACGTGA GCCACGAAGA CCCTGAGGTC  10320
AAGTTCAACT GGTACGTGGA CGGCGTGGAG GTGCATAATG CCAAGACAAA GCCGCGGGAG  10380
GAGCAGTACA ACAGCACGTA CCGTGTGGTC AGCGTCCTCA CCGTCCTGCA CCAGGACTGG  10440
CTGAATGGCA AGGAGTACAA GTGCAAGGTC TCCAACAAAG CCCTCCCAGC CCCCATCGAG  10500
AAAACCATCT CCAAAGCCAA AGGGCAGCCC CGAGAACCAC AGGTGTACAC CCTGCCCCCA  10560
TCCCGGGATG AGCTGACCAA GAACCAGGTC AGCCTGACCT GCCTGGTCAA AGGCTTCTAT  10620
CCCAGCGACA TCGCCGTGGA GTGGGAGAGC AATGGGCAGC CGGAGAACAA CTACAAGACC  10680
ACGCCTCCCG TGCTGGACTC CGACGGCTCC TTCTTCCTCT ACAGCAAGCT CACCGTGGAC  10740
AAGAGCAGGT GGCAGCAGGG GAACGTCTTC TCATGCTCCG TGATGCATGA GGCTCTGCAC  10800
AACCACTACA CGCAGAAGAG CCTCTCCCTG TCTCCGGGTA AATGAGGATC CGTTAACGGT  10860
TACCAACTAC CTAGACTGGA TTCGTGACAA CATGCGGCCG TGATATCTAC GTATGATCAG  10920
```

FIG. 8N

```
CCTCGACTGT GCCTTCTAGT TGCCAGCCAT CTGTGTTG CCCCTCCCCC GTGCCTTCCT    10980
TGACCCTGGA AGGTGCCACT CCCACTGTCC TTTCCTAATA AATGAGGAA ATTGCATCGC   11040
ATTGTCTGAG TAGGTGTCAT TCTATTCTGG GGGGTGGGGT GGGGCAGGAC AGCAAGGGGG  11100
AGGATTGGGA AGACAATAGC AGGCATGCTG GGGATGCGGT GGGCTCTATG GAACCAGCTG  11160
GGGCTCGACA GCAACGCTAG GTCGAGGCCG CTACTAACTC TCTCCTCCCT CCTTTTCCT   11220
GCAGGACGAG GCAGCGCGGC TATCGTGGCT GGCCACGACG GGCGTTCCTT GCGCAGCTGT  11280
GCTCGACGTT GTCACTGAAG CGGGAAGGGA CTGGCTGCTA TTGGGCGAAG TGCCGGGGCA  11340
GGATCTCCTG TCATCTCACC TTGCTCCTGC CGAGAAAGTA TCCATCATGG CTGATGCAAT  11400
GCGGGCGGCTG CATACGCTTG ATCCGGCTAC CTGCCCATTC GACCACCAAG CGAAACATCG  11460
CATCGAGCGA GCACGTACTC GGATGGAAGC CGGTCTTGTC GATCAGGATG ATCTGGACGA  11520
AGAGCATCAG GGGCTCGCGG CAGCCGAACT GTTCGCCAGG TAAGTGAGCT CCAATTCAAG  11580
CTTCCTAGGG CGGCCAGCTA GTAGCTTTGC TTCTCAATTT CTTATTTGCA TAATGAGAAA  11640
AAAAGGAAAA TTAATTTTAA CACCAATTCA GTAGTTGATT GAGCAAATGC GTTGCCAAAA  11700
AGGATGCTTT AGAGACAGTG TTCTCTGCAC AGATAAGGAC AAACATTATT CAGAGGGAGT  11760
```

FIG. 8P

| | | | | |
|---|---|---|---|---|
| ACCCAGAGCT | GAGACTCCTA | AGCCAGTGAG | TGGCACAGCA | TTCTAGGGAG AAATATGCTT 11820 |
| GTCATCACCG | AAGCCTGATT | CCGTAGAGCC | ACACCTTGGT | AAGGGCCAAT CTGCTCACAC 11880 |
| AGGATAGAGA | GGGCAGGAGC | CAGGGCAGAG | CATATAAGGT | GAGGTAGGAT CAGTTGCTCC 11940 |
| TCACATTTGC | TTCTGACATA | GTTGTGTTGG | GAGCTTGGAT | AGCTTGGACA GCTCAGGGCT 12000 |
| GCGATTTCGC | GCCAAACTTG | ACGGCAATCC | TAGCGTGAAG | GCTGGTAGGA TTTTATCCCC 12060 |
| GCTGCCATCA | TGGTTCGACC | ATTGAACTGC | ATCGTCGCCG | TGTCCCAAAA TATGGGGATT 12120 |
| GGCAAGAACG | GAGACCTACC | CTGGCCTCCG | CTCAGGAACG | AGTTCAAGTA CTTCCAAAGA 12180 |
| ATGACCACAA | CCTCTTCAGT | GGAAGGTAAA | CAGAATCTGG | TGATTATGGG TAGGAAAACC 12240 |
| TGGTTCTCCA | TTCCTGAGAA | GAATCGACCT | TTAAAGGACA | GAATTAATAT AGTTCTCAGT 12300 |
| AGAGAACTCA | AAGAACCACC | ACGAGGAGCT | CATTTCTTG | CCAAAAGTTT GGATGATGCC 12360 |
| TTAAGACTTA | TTGAACAACC | GGAATTGGCA | AGTAAAGTAG | ACATGGTTTG GATAGTCGGA 12420 |
| GGCAGTTCTG | TTTACCAGGA | AGCCATGAAT | CAACCAGGCC | ACCTTAGACT CTTTGTGACA 12480 |
| AGGATCATGC | AGGAATTTGA | AAGTGACACG | TTTTCCCAG | AAATTGATTT GGGGAAATAT 12540 |
| AAACTTCTCC | CAGAATACCC | AGGCGTCCTC | TCTGAGGTCC | AGGAGGAAAA AGGCATCAAG 12600 |

FIG. 8Q

```
TATAAGTTTG AAGTCTACGA GAAGAAAGAC TAACAGGAAG ATGCTTTCAA GTTCTCTGCT   12660
CCCTCCTAA AGCTATGCAT TTTTATAAGA CCATGGGACT TTTGCTGGCT TTAGATCAGC    12720
CTCGACTGTG CCTTCTAGTT GCCAGCCATC TGTTGTTGC CCCTCCCCCG TGCCTTCCTT    12780
GACCCTGGAA GGTGCCACTC CCACTGTCCT TCCTAATAA AATGAGGAAA TTGCATCGCA    12840
TTGTCTGAGT AGGTGTCATT CTATTCTGGG GGGTGGGGTG GGGCAGGACA GCAAGGGGA    12900
GGATGGGAA GACAATAGCA GGCATGCTGG GGATGCGGTG GGCTCTATGG AACCAGCTGG    12960
GGCTCGAAGC GGCCGCCCAT TTCGCTGGTG GTCAGATGCG GGATGGCGTG GGACGCGGCG   13020
GGGAGCCGTCA CACTGAGGTT TTCCGCCAGA CGCCACTGCT GCCAGGCGCT GATGTGCCCG  13080
GCTTCTGACC ATGCGGTCGC GTTCGGTTGC ACTACGCGTA CTGTGAGCCA GAGTTGCCCG   13140
GCGCTCTCCG GCTGCGGTAG TTCAGGCAGT TCAATCAACT GTTACCTTG TGGACCGACA    13200
TCCAGAGGCA CTTCACCGCT TGCCAGCGGC TTACCATCCA GCGCCACCAT CCAGTGCAGG   13260
AGCTCGTTAT CGCTATGACG GAACAGGTAT TCGCTGGTCA CTTCGATGGT TTGCCCGGAT   13320
AAACGGAACT GGAAAAACTG CTGCTGGTGT TTTGCTTCCG TCAGCGCTGG ATGCGGGGTG   13380
CGGTCGGCAA AGACCAGACC GTTCATACAG AACTGGCGAT CGTTCGGGCGT ATCGCCAAAA  13440
```

FIG. 8R

```
TCACCGCCGT AAGCCGACCA CGGGTTGCCG TTTCATCAT ATTTAATCAG CGACTGATCC   13500
ACCCAGTCCC AGACGAAGCC GCCCTGTAAA CGGGGATACT GACGAAACGC CTGCCAGTAT   13560
TTAGCGAAAC CGCCAAGACT GTTACCCATC GCTGGGGCGT ATTCGCAAAG GATCAGCGGG   13620
CGCGTCTCTC CGGGTAGCGA AAGCCATTTT TTGATGGACC ATTTCGGACC AGCCGGGAAG   13680
GGCTGGTCTT CATCCACGCG CGCGTACATC GGGCAAATAA TATCGGTGGC CGTGGTGTCG   13740
GCTCCGCCGC CTTCATACTG CACCGGGCGG GAAGGATCGA CAGATTTGAT CCAGCGATAC   13800
AGCGCGTCGT GATTAGCGCC GTGGCCTGAT TCATTCCCCA GCGACCAGAT GATCACACTC   13860
GGGTGATTAC GATCGCGCTG CACCATTCGC GTTACGCCGT CGCTCATCGC CGGTAGCCAG   13920
CGGGGATCAT CGGTCAGACG ATTCATTGGC ACCATGCCGT GGGTTTCAAT ATTGGCTTCA   13980
TCCACCACAT ACAGGCCGTA GCGGTCGCAC AGCGTGTACC ACAGCGGATG GTTCGGATAA   14040
TGCCAACAGC GCACGGCGTT AAAGTTGTTC TGCTTCATCA GCAGGATATC CTGCACCATC   14100
GTCTGCTCAT CCATGACCTG ACCATGCAGA GGATGATGCT CGTGACGGTT AACGCCTCGA   14160
ATCAGCAACG GCTTGCCGTT CAGCAGCAGC AGACCATTTT CAATCCGCAC CTCGCGGAAA   14220
CCGACATCGC AGGCTTCTGC TTCAATCAGC GTGCCGTCGG CGGTGTGCAG TTCAACCACC   14280
```

FIG. 8S

```
GCACGATAGA GATTCGGGAT TTCGGCGCTC CACAGTTCG GGTTTCGAC GTTCAGACGC   14340
AGTGTGACGC GATCGGCATA ACCACCACGC TCATCGATAA TTTCACCGCC GAAAGGGCG   14400
GTGCCGCTGG CGACCTGCGT TTCACCCTGC CATAAAGAAA CTGTTACCCG TAGGTAGTCA   14460
CGCAACTCGC CGCACATCTG AACTTCAGCC TCCAGTACAG CGGGGCTGAA ATCATCATTA   14520
AAGCGAGTGG CAACATGGAA ATCGCTGATT TGTGTAGTCG GTTTATGCAG CAACGAGACG   14580
TCACGGAAAA TGCCGCTCAT CCGCCACATA TCCTGATCTT CCAGATAACT GCCGTCACTC   14640
CAACGCAGCA CCATCACCGC GAGGGGGTTT TCTCCGGCCG TAACCGACCC ACGCCCCGTT GCACCACAGA   14700
AATTCAGACG GCAAACGACT GTCCTGGCCG ATCAAAAATA ATTCGCGTCT GGCCTTCCTG TAGCCAGCTT   14760
TGAAACGCCG AGTTAACGCC ATCAAAAATA ATTCGCGTCT GGCCTTCCTG TAGCCAGCTT   14820
TCATCAACAT TAAATGTGAG CGAGTAACAA CCCGTCGGAT TCTCCGTGGG AACAAACGGC   14880
GGATTGACCG TAATGGGATA GGTTACGTTG GTGTAGATGG GCGCATCGTA ACCGTGCATC   14940
TGCCAGTTTG AGGGGACGAC GACAGTATCG GCCTCAGGAA GATCGCACTC CAGCCAGCTT   15000
TCCGGCACCG CTTCTGGTGC CGGAAACCAG GCAAAGCGCC ATTCGCCATT CAGGCTGCGC   15060
AACTGTTGGG AAGGGCGATC GGTGCGGGCC TCTTCGCTAT TACGCCAGCT GGCGAAAGGG   15120
```

FIG. 8T

```
GGATGTGCTG CAAGGCGATT AAGTTGGGTA ACGCCAGGGT TTCCCAGTC ACGACGTGT   15180
AAAACGACTT AATCCGTCGA GGGGCTGCCT CGAAGCAGAC GACCTTCCGT TGTGCAGCCA   15240
GCGGGGCCTG CGCCGGTGCC CACAATCGTG CGGAACAAA CTAAACCAGA ACAAATTATA   15300
CCGGGGGCAC CGCCGCCACC ACCTTCTCCC GTGCCTAACA TTCCAGGGCC TCCACCACCA   15360
CCACCACCAT CGATGTCTGA ATTGCCGCCC GCTCCACCAA TGCCGACGGA ACCTCAACCC   15420
GCTGCACCTT TAGACGACAG ACAACAATTG TTGGAAGCTA TTAGAAACGA AAAAAATCGC   15480
ACTCGTCTCA GACCGGTCAA ACCAAAAACG GCGCCCGAAA CCAGTACAAT AGTTGAGGTG   15540
CCGACTGTGT TGCCTAAAGA GACATTTGAG CCTAAACCGC CGTCTGCATC ACCGCCACCA   15600
CCTCCGCCTC CGCCTCCGCC GCCAGCCCCG CCTGCGCCTC CACCGATGGT AGATTATCA   15660
TCAGCTCCAC CACCGCCGCC ATTAGTAGAT TTGCCGTCTG AAATGTTACC ACCGCCTGCA   15720
CCATCGCTTT CTAACGTGTT GTCTGAATTA AAATCGGGCA CAGTTAGATT GAAACCCGCC   15780
CAAAAACGCC CGCAATCAGA AATAATTCCA AAAAGCTCAA CTACAAATTT GATCGCGGAC   15840
GTGTTAGCCG ACACAATTAA TAGGCGTCGT GTGGCTATGG CAAAATCGTC TTCGAAGCA    15900
ACTTCTAACG ACGAGGGTTG GGACGACGAC GATAATCGGC CTAATAAAGC TAACACGCCC   15960
```

FIG. 8U

| | | | | |
|---|---|---|---|---|
| GATGTTAAAT | ATGTCCAAGC | TACTAGTGGT | ACCGCTTGGC | AGAACATATC | CATCGGCGTCC | 16020 |
| GCCATCTCCA | GCAGCCGCAC | GCGGCGCATC | TCGGGCAGCG | TTGGGTCCTG | GCCACGGGTG | 16080 |
| CGCATGATCG | TGCTCCTGTC | GTTGAGGACC | CGGCTAGGCT | GGCGGGGTTG | CCTTACTGGT | 16140 |
| TAGCAGAATG | AATCACCGAT | ACGCGAGCGA | ACGTGAAGCG | ACTGCTGCTG | CAAAACGTCT | 16200 |
| GCGACCTGAG | CAACAACATG | AATGGTCTTC | GGTTTCCGTG | TTTCGTAAAG | TCTGGAAACG | 16260 |
| CGGAAGTCAG | CGCCCTGCAC | CATTATGTTC | CGGATCTGCA | TCGCAGGATG | CTGCTGGCTA | 16320 |
| CCCTGTGGAA | CACCTACATC | TGTATTAACG | AAGCGCTGGC | ATTGACCCTG | AGTGATTTTT | 16380 |
| CTCTGGTCCC | GCCGCATCCA | TACCGCCAGT | TGTTTACCCT | CACAACGTTC | CAGTAACCGG | 16440 |
| GCATGTTCAT | CATCAGTAAC | CCGTATCGTG | AGCATCCTCT | CTCGTTTCAT | CGGTATCATT | 16500 |
| ACCCCCATGA | ACAGAAATCC | CCCTTACACG | GAGGCATCAG | TGACCAAACA | GGAAAAAACC | 16560 |
| GCCCTTAACA | TGGCCCGCTT | TATCAGAAGC | CAGACATTAA | CGCTTCTGGA | GAAACTCAAC | 16620 |
| GAGCTGGACG | CGGATGAACA | GGCAGACATC | TGTGAATCGC | TTCACGACCA | CGCTGATGAG | 16680 |
| CTTTACCGCA | GCTGCCTCGC | GCGTTTCGGT | GATGACGGTG | AAAACCTCTG | ACACATGCAG | 16740 |
| CTCCCGGAGA | CGGTCACAGC | TTGTCTGTAA | GCGGATGCCG | GGAGCAGACA | AGCCCGTCAG | 16800 |

FIG. 8V

```
GGCGGGTCAG CGGGTGTTGG CGGGTGTCGG GGCGCAGCCA TGACCCAGTC ACGTAGCGAT  16860
AGCGGAGTGT ATACTGGCTT AACTATGCGG CATCAGAGCA GATTGTACTG AGAGTGCACC  16920
ATATGCGGTG TGAAATACCG CACAGATGCG TAAGGAGAAA ATACCGCATC AGGGCGCTCTT  16980
CCGCTTCCTC GCTCACTGAC TCGCTGCGCT CGGTCGTTCG GCTGCGGCGA GCGGTATCAG  17040
CTCACTCAAA GGCGGTAATA CGGTTATCCA CAGAATCAGG GGATAACGCA GGAAAGAACA  17100
TGTGAGCAAA AGGCCAGCAA AAGGCCAGGA ACCGTAAAAA GGCCGCGTTG CTGGCGTTTT  17160
TCCATAGGCT CCGCCCCCCT GACGAGCATC ACAAAAATCG ACGCTCAAGT CAGAGGTGGC  17220
GAAACCCGAC AGGACTATAA AGATACCAGG CGTTTCCCCC TGGAAGCTCC CTCGTGCGCT  17280
CTCCTGTTCC GACCCTGCCG CTTACCGGAT ACCTGTCCGC CTTTCTCCCT TCGGGAAGCG  17340
TGGCGCTTTC TCATAGCTCA CGCTGTAGGT ATCTCAGTTC GGTGTAGGTC GTTCGCTCCA  17400
AGCTGGGCTG TGTGCACGAA CCCCCCGTTC AGCCCGACCG CTGCGCCTTA TCCGGTAACT  17460
ATCGTCTTGA GTCCAACCCG GTAAGACACG ACTTATCGCC ACTGGCAGCA GCCACTGGTA  17520
ACAGGATTAG CAGAGCGAGG TATGTAGGCG GTGCTACAGA GTTCTTGAAG TGGTGGCCTA  17580
ACTACGGCTA CACTAGAAGG ACAGTATTTG GTATCTGCGC TCTGCTGAAG CCAGTTACCT  17640
```

FIG. 8W

```
TCGGAAAAAG AGTTGGTAGC TCTTGATCCG GCAAACAAAC CACCGCTGGT AGCGGTGGTT   17700
TTTTGTTTG CAAGCAGCAG ATTACGCGCA GAAAAAAGG ATCTCAAGAA GATCCTTTGA    17760
TCTTTCTAC GGGGTCTGAC GCTCAGTGGA ACGAAAACTC ACGTTAAGGG ATTTGGTCA    17820
TGAGATTATC AAAAAGGATC TTCACCTAGA TCCTTTTAAA TTAAAAATGA AGTTTTAAAT  17880
CAATCTAAAG TATATATGAG TAAACTTGGT CTGACAGTTA CCAATGCTTA ATCAGTGAGG  17940
CACCTATCTC AGCGATCTGT CTATTTCGTT CATCCATAGT TGCCTGACTC CCCGTCGTGT  18000
AGATAACTAC GATACGGGAG GGCTTACCAT CTGGCCCCAG TGCTGCAATG ATACCGCGAG  18060
ACCCACGCTC ACCGGCTCCA GATTTATCAG CAATAAACCA GCCAGCCGGA AGGGCCGAGC  18120
GCAGAAGTGG TCCTGCAACT TTATCCGCCT CCATCCAGTC TATTAATTGT TGCCGGGAAG  18180
CTAGAGTAAG TAGTTCGCCA GTTAATAGTT TGCGCAACGT TGTTGCCATT GCTGCAGGCA  18240
TCGTGGTGTC ACGCTCGTCG TTTGGTATGG CTTCATTCAG CTCCGGTTCC CAACGATCAA  18300
GGCGAGTTAC ATGATCCCCC ATGTTGTGCA AAAAAGCGGT TAGCTCCTTC GGTCCTCCGA  18360
TCGTTGTCAG AAGTAAGTTG GCCGCAGTGT TATCACTCAT GGTTATGGCA GCACTGCATA  18420
ATTCTCTTAC TGTCATGCCA TCCGTAAGAT GCTTTTCTGT GACTGGTGAG TACTCAACCA  18480
```

FIG. 8X

```
AGTCATTCTG AGAATAGTGT ATGCGGGCGAC CGAGTTGCTC TTGCCCGGCG TCAACACGGG    18540
ATAATACCGC GCCACATAGC AGAACTTTAA AAGTGCTCAT CATTGGAAAA CGTTCTTCGG    18600
GGCGAAAACT CTCAAGGATC TTACCGCTGT TGAGATCCAG TTCGATGTAA CCCACTCGTG    18660
CACCCAACTG ATCTTCAGCA TCTTTTACTT TCACCAGCGT TTCTGGGTGA GCAAAAACAG    18720
GAAGGCAAAA TGCCGCAAAA AAGGGAATAA GGGCGACACG GAAATGTTGA ATACTCATAC    18780
TCTTCCTTTT TCAATATTAT TGAAGCATTT ATCAGGGGTTA TTGTCTCATG AGCGGATACA    18840
TATTTGAATG TATTTAGAAA AATAAACAAA TAGGGGTTCC GCGCACATTT CCCCGAAAAG    18900
TGCCACCTGA CGTCTAAGAA ACCATTATTA TCATGACATT AACCTATAAA AATAGGCGTA    18960
TCACGAGGCC CTTTCGTCTT CAAGAA                                        18986
```

METHOD FOR INTEGRATING GENES AT SPECIFIC SITES IN MAMMALIAN CELLS VIA HOMOLOGOUS RECOMBINATION AND VECTORS FOR ACCOMPLISHING THE SAME

FIELD OF THE INVENTION

The present invention relates to a process of targeting the integration of a desired exogenous DNA to a specific location within the genome of a mammalian cell. More specifically, the invention describes a novel method for identifying a transcriptionally active target site ("hot spot") in the mammalian genome, and inserting a desired DNA at this site via homologous recombination. The invention also optionally provides the ability for gene amplification of the desired DNA at this location by co-integrating an amplifiable selectable marker, e.g., DHFR, in combination with the exogenous DNA. The invention additionally describes the construction of novel vectors suitable for accomplishing the above, and further provides mammalian cell lines produced by such methods which contain a desired exogenous DNA integrated at a target hot spot.

BACKGROUND

Technology for expressing recombinant proteins in both prokaryotic and eukaryotic organisms is well established. Mammalian cells offer significant advantages over bacteria or yeast for protein production, resulting from their ability to correctly assemble, glycosylate and post-translationally modify recombinantly expressed proteins. After transfection into the host cells, recombinant expression constructs can be maintained as extrachromosomal elements, or may be integrated into the host cell genome. Generation of stably transfected mammalian cell lines usually involves the latter; a DNA construct encoding a gene of interest along with a drug resistance gene (dominant selectable marker) is introduced into the host cell, and subsequent growth in the presence of the drug allows for the selection of cells that have successfully integrated the exogenous DNA. In many instances, the gene of interest is linked to a drug resistant selectable marker which can later be subjected to gene amplification. The gene encoding dihydrofolate reductase (DHFR) is most commonly used for this purpose. Growth of cells in the presence of methotrexate, a competitive inhibitor of DHFR, leads to increased DHFR production by means of amplification of the DHFR gene. As flanking regions of DNA will also become amplified, the resultant coamplification of a DHFR linked gene in the transfected cell line can lead to increased protein production, thereby resulting in high level expression of the gene of interest.

While this approach has proven successful, there are a number of problems with the system because of the random nature of the integration event. These problems exist because expression levels are greatly influenced by the effects of the local genetic environment at the gene locus, a phenomena well documented in the literature and generally referred to as "position effects" (for example, see Al-Shawi et al, *Mol. Cell. Biol.*, 10:1192–1198 (1990); Yoshimura et al, *Mol. Cell. Biol.*, 7:1296–1299 (1987)). As the vast majority of mammalian DNA is in a transcriptionally inactive state, random integration methods offer no control over the transcriptional fate of the integrated DNA. Consequently, wide variations in the expression level of integrated genes can occur, depending on the site of integration. For example, integration of exogenous DNA into inactive, or transcriptionally "silent" regions of the genome will result in little or no expression. By contrast integration into a transcriptionally active site may result in high expression.

Therefore, when the goal of the work is to obtain a high level of gene expression, as is typically the desired outcome of genetic engineering methods, it is generally necessary to screen large numbers of transfectants to find such a high producing clone. Additionally, random integration of exogenous DNA into the genome can in some instances disrupt important cellular genes, resulting in an altered phenotype. These factors can make the generation of high expressing stable mammalian cell lines a complicated and laborious process.

Recently, our laboratory has described the use of DNA vectors containing translationally impaired dominant selectable markers in mammalian gene expression. (This is disclosed in U.S. Pat. No. 5,648,267.

These vectors contain a translationally impaired neomycin phosphotransferase (neo) gene as the dominant selectable marker, artificially engineered to contain an intron into which a DHFR gene along with a gene or genes of interest is inserted. Use of these vectors as expression constructs has been found to significantly reduce the total number of drug resistant colonies produced, thereby facilitating the screening procedure in relation to conventional mammalian expression vectors. Furthermore, a significant percentage of the clones obtained using this system are high expressing clones. These results are apparently attributable to the modifications made to the neo selectable marker. Due to the translational impairment of the neo gene, transfected cells will not produce enough neo protein to survive drug selection, thereby decreasing the overall number of drug resistant colonies. Additionally, a higher percentage of the surviving clones will contain the expression vector integrated into sites in the genome where basal transcription levels are high, resulting in overproduction of neo, thereby allowing the cells to overcome the impairment of the neo gene. Concomitantly, the genes of interest linked to neo will be subject to similar elevated levels of transcription. This same advantage is also true as a result of the artificial intron created within neo; survival is dependent on the synthesis of a functional neo gene, which is in turn dependent on correct and efficient splicing of the neo introns. Moreover, these criteria are more likely to be met if the vector DNA has integrated into a region which is already highly transcriptionally active.

Following integration of the vector into a transcriptionally active region, gene amplification is performed by selection for the DHFR gene. Using this system, it has been possible to obtain clones selected using low levels of methotrexate (50 nM), containing few (<10) copies of the vector which secrete high levels of protein (>55pg/cell/day). Furthermore, this can be achieved in a relatively short period of time. However, the success in amplification is variable. Some transcriptionally active sites cannot be amplified and therefore the frequency and extent of amplification from a particular site is not predictable.

Overall, the use of these translationally impaired vectors represents a significant improvement over other methods of random integration. However, as discussed, the problem of lack of control over the integration site remains a significant concern.

One approach to overcome the problems of random integration is by means of gene targeting, whereby the exogenous DNA is directed to a specific locus within the host genome. The exogenous DNA is inserted by means of homologous recombination occurring between sequences of DNA in the expression vector and the corresponding homologous sequence in the genome. However, while this type of recombination occurs at a high frequency naturally in yeast and other fungal organisms, in higher eukaryotic organisms it is an extremely rare event. In mammalian cells, the frequency of homologous versus non-homologous (random integration) recombination is reported to range from 1/100 to 1/5000 (for example, see Capecchi, *Science*, 244:1288–1292 (1989); Morrow and Kucherlapati, *Curr. Op. Biotech.*, 4:577–582 (1993)).

One of the earliest reports describing homologous recombination in mammalian cells comprised an artificial system created in mouse fibroblasts (Thomas et al, *Cell*, 44:419–428 (1986)). A cell line containing a mutated, non-functional version of the neo gene integrated into the host genome was created, and subsequently targeted with a second non-functional copy of neo containing a different mutation. Reconstruction of a functional neo gene could occur only by gene targeting. Homologous recombinants were identified by selecting for G418 resistant cells, and confirmed by analysis of genomic DNA isolated from the resistant clones.

Recently, the use of homologous recombination to replace the heavy and light immunoglobulin genes at endogenous loci in antibody secreting cells has been reported. (U.S. Pat. No. 5,202,238, Fell et al, (1993).) However, this particular approach is not widely applicable, because it is limited to the production of immunoglobulins in cells which endogenously express immunoglobulins, e.g., B cells and myeloma cells. Also, expression is limited to single copy gene levels because co-amplification after homologous recombination is not included. The method is further complicated by the fact that two separate integration events are required to produce a functional immunoglobulin: one for the light chain gene followed by one for the heavy chain gene.

An additional example of this type of system has been reported in NS/0 cells, where recombinant immunoglobulins are expressed by homologous recombination into the immunoglobulin gamma 2A locus (Hollis et al, international patent application # PCT/IB95 (00014).) Expression levels obtained from this site were extremely high—on the order of 20pg/cell/day from a single copy integrant. However, as in the above example, expression is limited to this level because an amplifiable gene is not contegrated in this system. Also, other researchers have reported aberrant glycosylation of recombinant proteins expressed in NS/0 cells (for example, see Flesher et al, *Biotech. and Bioeng.*, 48:399–407 (1995)), thereby limiting the applicability of this approach.

The cre-loxP recombination system from bacteriophage P1 has recently been adapted and used as a means of gene targeting in eukaryotic cells. Specifically, the site specific integration of exogenous DNA into the Chinese hamster ovary (CHO) cell genome using cre recombinase and a series of lox containing vectors have been described. (Fukushige and Sauer, *Proc. Natl. Acad. Sci. USA*, 89:7905–7909 (1992).) This system is attractive in that it provides for reproducible expression at the same chromosomal location. However, no effort was made to identify a chromosomal site from which gene expression is optimal, and as in the above example, expression is limited to single copy levels in this system. Also, it is complicated by the fact that one needs to provide for expression of a functional recombinase enzyme in the mammalian cell.

The use of homologous recombination between an introduced DNA sequence and its endogenous chromosomal locus has also been reported to provide a useful means of genetic manipulation in mammalian cells, as well as in yeast cells. (See e.g., Bradley et al, *Meth. Enzymol.*, 223:855–879 (1993); Capecchi, *Science*, 244:1288–1292 (1989); Rothstein et al, *Meth. Enzymol.*, 194:281–301 (1991)). To date, most mammalian gene targeting studies have been directed toward gene disruption ("knockout") or site-specific mutagenesis of selected target gene loci in mouse embryonic stem (ES) cells. The creation of these "knockout" mouse models has enabled scientists to examine specific structure-function issues and examine the biological importance of a myriad of mouse genes. This field of research also has important implications in terms of potential gene therapy applications.

Also, vectors have recently been reported by Cell-tech (Kent, U.K.) which purportedly are targeted to transcriptionally active sites in NSO cells, which do not require gene amplification (Peakman et al, *Hum. Antibod. Hybridomas*, 5:65–74 (1994)). However, levels of immunoglobulin secretion in these unamplified cells have not been reported to exceed 20pg/cell/day, while in amplified CHO cells, levels as high as 100pg/cell/day can be obtained (Id.).

It would be highly desirable to develop a gene targeting system which reproducibly provided for the integration of exogenous DNA into a predetermined site in the genome known to be transcriptionally active. Also, it would be desirable if such a gene targeting system would further facilitate co-amplification of the inserted DNA after integration. The design of such a system would allow for the reproducible and high level expression of any cloned gene of interest in a mammalian cell, and undoubtedly would be of significant interest to many researchers.

In this application, we provide a novel mammalian expression system, based on homologous recombination occurring between two artificial substrates contained in two different vectors. Specifically, this system uses a combination of two novel mammalian expression vectors, referred to as a "marking" vector and a "targeting" vector.

Essentially, the marking vector enables the identification and marking of a site in the mammalian genome which is transcriptionally active, i.e., a site at which gene expression levels are high. This site can be regarded as a "hot spot" in the genome. After integration of the marking vector, the subject expression system enables another DNA to be integrated at this site, i.e., the targeting vector, by means of homologous recombination occurring between DNA sequences common to both vectors. This system affords significant advantages over other homologous recombination systems.

Unlike most other homologous systems employed in mammalian cells, this system exhibits no background. Therefore, cells which have only undergone random integration of the vector do not survive the selection. Thus, any gene of interest cloned into the targeting plasmid is expressed at high levels from the marked hot spot. Accordingly, the subject method of gene expression substantially or completely eliminates the problems inherent to systems of random integration, discussed in detail above. Moreover, this system provides reproducible and high level expression of any recombinant protein at the same transcriptionally active site in the mammalian genome. In addition, gene amplification may be effected at this particular transcriptionally active site by including an amplifiable dominant selectable marker (e.g. DHFR) as part of the marking vector.

OBJECTS OF THE INVENTION

Thus, it is an object of the invention to provide an improved method for targeting a desired DNA to a specific site in a mammalian cell.

It is a more specific object of the invention to provide a novel method for targeting a desired DNA to a specific site in a mammalian cell via homologous recombination.

It is another specific object of the invention to provide novel vectors for achieving site specific integration of a desired DNA in a mammalian cell.

It is still another object of the invention to provide novel mammalian cell lines which contain a desired DNA integrated at a predetermined site which provides for high expression.

It is a more specific object of the invention to provide a novel method for achieving site specific integration of a desired DNA in a Chinese hamster ovary (CHO) cell.

It is another more specific object of the invention to provide a novel method for integrating immunoglobulin genes, or any other genes, in mammalian cells at predetermined chromosomal sites that provide for high expression.

It is another specific object of the invention to provide novel vectors and vector combinations suitable for integrating immunoglobulin genes into mammalian cells at predetermined sites that provide for high expression.

It is another object of the invention to provide mammalian cell lines which contain immunoglobulin genes integrated at predetermined sites that provide for high expression.

It is an even more specific object of the invention to provide a novel method for integrating immunoglobulin genes into CHO cells that provide for high expression, as well as novel vectors and vector combinations that provide for such integration of immunoglobulin genes into CHO cells.

In addition, it is a specific object of the invention to provide novel CHO cell lines which contain immunoglobulin genes integrated at predetermined sites that provide for high expression, and have been amplified by methotrexate selection to secrete even greater amounts of functional immunoglobulins.

BRIEF DESCRIPTION OF THE FIGURES

FIG. 2(a) shows a map of a targeting plasmid referred to "Molly". Molly is shown here encoding the anti-CD20 immunoglobulin genes, expression of which is described in Example 1.

FIGS. 7A through 7G [SEQ ID NO.:1] contain the Sequence Listing for Desmond.

FIGS. 8A through 8I [SEQ ID NO.:2] contain the Sequence Listing for Molly-containing anti-CD20.

DETAILED DESCRIPTION OF THE INVENTION

Figure 1A:
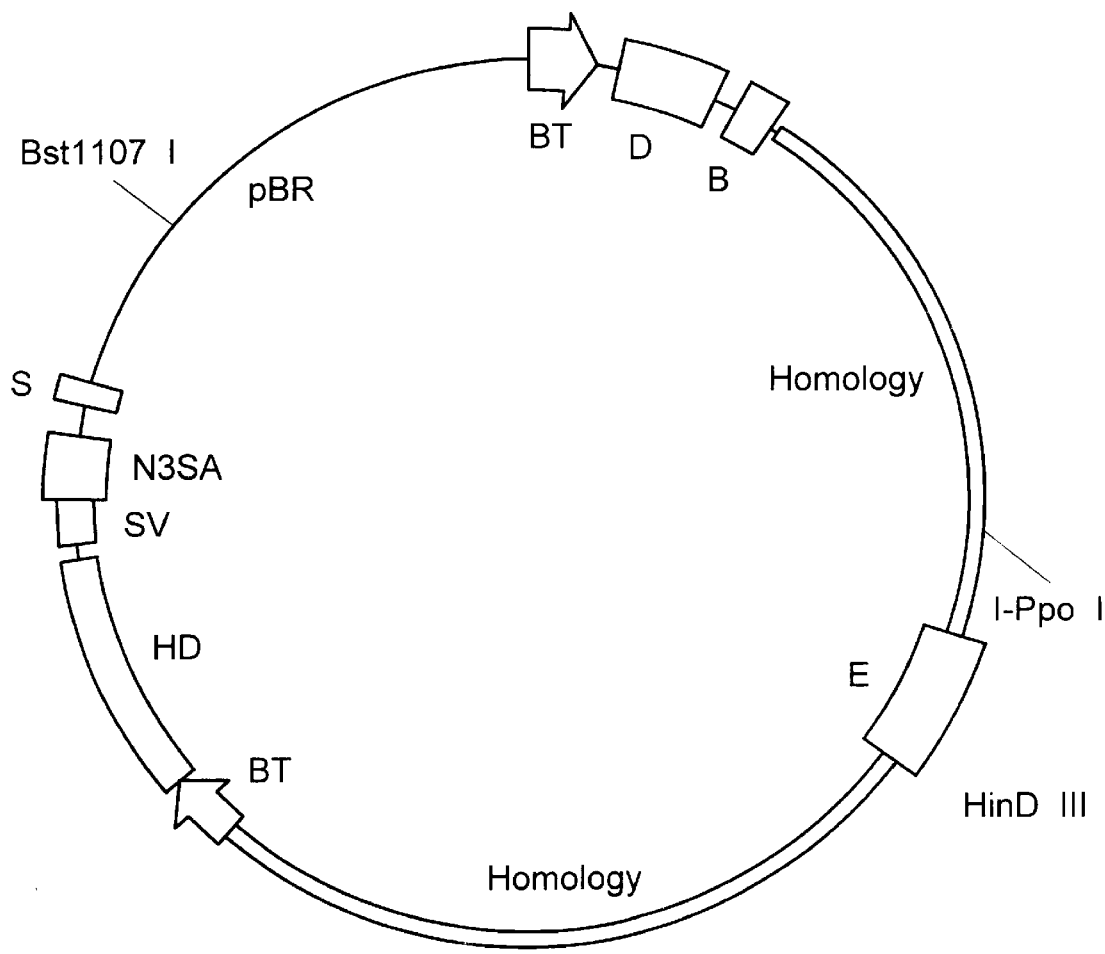
FIGS. 1A and 1B depict a map of a marking plasmid according to the invention referred to as Desmond. The plasmid is shown in circular form (1a) as well as a linearized version used for transfection (1b).

The invention provides a novel method for integrating a desired exogenous DNA at a target site within the genome of a mammalian cell via homologous recombination. Also, the invention provides novel vectors for achieving the site specific integration of a DNA at a target site in the genome of a mammalian cell.

More specifically, the subject cloning method provides for site specific integration of a desired DNA in a mammalian cell by transfection of such cell with a "marker plasmid" which contains a unique sequence that is foreign to the mammalian cell genome and which provides a substrate for homologous recombination, followed by transfection with a "target plasmid" containing a sequence which provides for homologous recombination with the unique sequence contained in the marker plasmid, and further comprising a desired DNA that is to be integrated into the mammalian cell. Typically, the integrated DNA will encode a protein of interest, such as an immunoglobulin or other secreted mammalian glycoprotein.

The exemplified homologous recombination system uses the neomycin phosphotransferase gene as a dominant selectable marker. This particular marker was utilized based on the following previously published observations;

(i) the demonstrated ability to target and restore function to a mutated version of the neo gene (cited earlier) and (ii) our development of translationally impaired expression vectors, in which the neo gene has been artificially created as two exons with a gene of interest inserted in the intervening intron; neo exons are correctly spliced and translated in vivo, producing a functional protein and thereby conferring G418 resistance on the resultant cell population. In this application, the neo gene is split into three exons. The third exon of neo is present on the "marker" plasmid and becomes integrated into the host cell genome upon integration of the marker plasmid into the mammalian cells. Exons 1 and 2 are present on the targeting plasmid, and are separated by an intervening intron into which at least one gene of interest is cloned. Homologous recombination of the targeting vector with the integrated marking vector results in correct splicing of all three exons of the neo gene and thereby expression of a functional neo protein (as determined by selection for G418 resistant colonies). Prior to designing the current expression system, we had experimentally tested the functionality of such a triply spliced neo construct in mammalian cells. The results of this control experiment indicated that all three neo exons were properly spliced and therefore suggested the feasibility of the subject invention.

However, while the present invention is exemplified using the neo gene, and more specifically a triple split neo gene, the general methodology should be efficacious with other dominant selectable markers.

As discussed in greater detail infra, the present invention affords numerous advantages to conventional gene expression methods, including both random integration and gene targeting methods. Specifically, the subject invention provides a method which reproducibly allows for site-specific integration of a desired DNA into a transcriptionally active domain of a mammalian cell. Moreover, because the subject method introduces an artificial region of "homology" which acts as a unique substrate for homologous recombination and the insertion of a desired DNA, the efficacy of subject invention does not require that the cell endogenously contain or express a specific DNA. Thus, the method is generically applicable to all mammalian cells, and can be used to express any type of recombinant protein.

The use of a triply spliced selectable marker, e.g., the exemplified triply spliced neo construct, guarantees that all G418 resistant colonies produced will arise from a homologous recombination event (random integrants will not produce a functional neo gene and consequently will not survive G418 selection). Thus, the subject invention makes it easy to screen for the desired homologous event. Furthermore, the frequency of additional random integrations in a cell that has under-gone a homologous recombination event appears to be low.

Based on the foregoing, it is apparent that a significant advantage of the invention is that it substantially reduces the number of colonies that need be screened to identify high producer clones, i.e., cell lines containing a desired DNA which secrete the corresponding protein at high levels. On average, clones containing integrated desired DNA may be identified by screening about 5 to 20 colonies (compared to several thousand which must be screened when using standard random integration techniques, or several hundred using the previously described intronic insertion vectors) Additionally, as the site of integration was preselected and comprises a transcriptionally active domain, all exogenous DNA expressed at this site should produce comparable, i.e. high levels of the protein of interest.

Moreover, the subject invention is further advantageous in that it enables an amplifiable gene to be inserted on integration of the marking vector. Thus, when a desired gene is targeted to this site via homologous recombination, the subject invention allows for expression of the gene to be further enhanced by gene amplification. In this regard, it has been reported in from the literature that different genomic sites have different capacities for gene amplification (Meinkoth et al, *Mol. Cell Biol.*, 7:1415–1424 (1987)). Therefore, this technique is further advantageous as it allows for the placement of a desired gene of interest at a specific site that is both transcriptionally active and easily amplified. Therefore, this should significantly reduce the amount of time required to isolate such high producers.

Specifically, while conventional methods for the construction of high expressing mammalian cell lines can take 6 to 9 months, the present invention allows for such clones to be isolated on average after only about 3–6 months. This is due to the fact that conventionally isolated clones typically must be subjected to at least three rounds of drug resistant gene amplification in order to reach satisfactory levels of gene expression. As the homologously produced clones are generated from a preselected site which is a high expression site, fewer rounds of amplification should be required before reaching a satisfactory level of production.

Still further, the subject invention enables the reproducible selection of high producer clones wherein the vector is integrated at low copy number, typically single copy. This is advantageous as it enhances the stability of the clones and avoids other potential adverse side-effects associated with high copy number. As described supra, the subject homologous recombination system uses the combination of a "marker plasmid" and a "targeting plasmid" which are described in more detail below. The "marker plasmid" which is used to mark and identify a transcriptionally hot spot will comprise at least the following sequences:

(i) a region of DNA that is heterologous or unique to the genome of the mammalian cell, which functions as a source of homology, allows for homologous recombination (with a DNA contained in a second target plasmid). More specifically, the unique region of DNA (i) will generally comprise a bacterial, viral, yeast synthetic, or other DNA which is not normally present in the mammalian cell genome and which further does not comprise significant homology or sequence identity to DNA contained in the genome of the mammalian cell. Essentially, this sequence should be sufficiently different to mammalian DNA that it will not significantly recombine with the host cell genome via homologous recombination. The size of such unique DNA will generally be at least about 2 to 10 kilobases in size, or higher, more preferably at least about 10 kb, as several other investigators have noted an increased frequency of targeted recombination as the size of the homology region is increased (Capecchi, *Science*, 244:1288–1292 (1989)).

The upper size limit of the unique DNA which acts as a site for homologous recombination with a sequence in the second target vector is largely dictated by potential stability constraints (if DNA is too large it may not be easily integrated into a chromosome) and the difficulties in working with very large DNAs.

(ii) a DNA including a fragment of a selectable marker DNA, typically an exon of a dominant selectable marker gene. The only essential feature of this DNA is that it not encode a functional selectable marker protein unless it is expressed in association with a sequence contained in the target plasmid. Typically, the target plasmid will comprise the remaining exons of the dominant selectable marker gene (those not comprised in "targeting" plasmid). Essentially, a functional selectable marker should only be produced if homologous recombination occurs (resulting in the association and expression of this marker DNA (i) sequence together with the portion(s) of the selectable marker DNA fragment which is (are) contained in the target plasmid).

As noted, the current invention exemplifies the use of the neomycin phosphotransferase gene as the dominant selectable marker which is "split" in the two vectors. However, other selectable markers should also be suitable, e.g., the Salmonella histidinol dehydrogenase gene, hygromycin phosphotransferase gene, herpes simplex virus thymidine kinase gene, adenosine deaminase gene, glutamine synthetase gene and hypoxanthine-guanine phosphoribosyl transferase gene.

(iii) a DNA which encodes a functional selectable marker protein, which selectable marker is different from the selectable marker DNA (ii). This selectable marker provides for the successful selection of mammalian cells wherein the marker plasmid is successfully integrated into the cellular DNA. More preferably, it is desirable that the marker plasmid comprise two such dominant selectable marker DNAs, situated at opposite ends of the vector. This is advantageous as it enables integrants to be selected using different selection agents and further enables cells which contain the entire vector to be selected. Additionally, one marker can be an amplifiable marker to facilitate gene amplification as discussed previously. Any of the dominant selectable marker listed in (ii) can be used as well as others generally known in the art.

Moreover, the marker plasmid may optionally further comprise a rare endonuclease restriction site. This is potentially desirable as this may facilitate cleavage. If present, such rare restriction site should be situated close to the middle of the unique region that acts as a substrate for homologous recombination. Preferably such sequence will be at least about 12 nucleotides. The introduction of a double stranded break by similar methodology has been reported to enhance the frequency of homologous recombination. (Choulika et al, *Mol. Cell. Biol.*, 15:1968–1973 (1995)). However, the presence of such sequence is not essential.

The "targeting plasmid" will comprise at least the following sequences:

(1) the same unique region of DNA contained in the marker plasmid or one having sufficient homology or sequence identity therewith that said DNA is capable of combining via homologous recombination with the unique region (i) in the marker plasmid. Suitable types of DNAs are described supra in the description of the unique region of DNA (1) in the marker plasmid.

(2) The remaining exons of the dominant selectable marker, one exon of which is included as (ii) in the marker plasmid listed above. The essential features of this DNA fragment is that it result in a functional (selectable) marker protein only if the target plasmid integrates via homologous recombination (wherein such recombination results in the association of this DNA with the other fragment of the selectable marker DNA contained in the marker plasmid) and further that it allow for insertion of a desired exogenous DNA. Typically, this DNA will comprise the remaining exons of the selectable marker DNA which are separated by an intron. For example, this DNA may comprise the first two exons of the neo gene and the marker plasmid may comprise the third exon (back third of neo).

(3) The target plasmid will also comprise a desired DNA, e.g., one encoding a desired polypeptide, preferably inserted within the selectable marker DNA fragment contained in the plasmid. Typically, the DNA will be inserted in an intron which is comprised between the exons of the selectable marker DNA. This ensures that the desired DNA is also integrated if homologous recombination of the target plasmid and the marker plasmid occurs. This intron may be naturally occurring or it may be engineered into the dominant selectable marker DNA fragment.

This DNA will encode any desired protein, preferably one having pharmaceutical or other desirable properties. Most typically the DNA will encode a mammalian protein, and in the current examples provided, an immunoglobulin or an immunoadhesin. However the invention is not in any way limited to the production of immunoglobulins.

As discussed previously, the subject cloning method is suitable for any mammalian cell as it does not require for efficacy that any specific mammalian sequence or sequences be present. In general, such mammalian cells will comprise those typically used for protein expression, e.g., CHO cells, myeloma cells, COS cells, BHK cells, Sp2/0 cells, NIH 3T3 and HeLa cells. In the examples which follow, CHO cells were utilized. The advantages thereof include the availability of suitable growth medium, their ability to grow efficiently and to high density in culture, and their ability to express mammalian proteins such as immunoglobulins in biologically active form.

Further, CHO cells were selected in large part because of previous usage of such cells by the inventors for the expression of immunoglobulins (using the translationally impaired dominant selectable marker containing vectors described previously). Thus, the present laboratory has considerable experience in using such cells for expression. However, based on the examples which follow, it is reasonable to expect similar results will be obtained with other mammalian cells.

In general, transformation or transfection of mammalian cells according to the subject invention will be effected according to conventional methods. So that the invention may be better understood, the construction of exemplary vectors and their usage in producing integrants is described in the examples below.

EXAMPLE 1

Design and Preparation of Marker and Targeting Plasmid DNA Vectors

The marker plasmid herein referred to as "Desmond" was assembled from the following DNA elements:

(a) Murine dihydrofolate reductase gene (DHFR), incorporated into a transcription cassette, comprising the mouse beta globin promoter 5" to the DHFR start site, and bovine growth hormone poly adenylation signal 3" to the stop codon. The DHFR transcriptional cassette was isolated from TCAE6, an expression vector created previously in this laboratory (Newman et al, 1992, *Biotechnology*, 10:1455–1460).

(b) *E. coli* β-galactosidase gene—commercially available, obtained from Promega as pSV-b-galactosidase control vector, catalog # E1081.

(c) Baculovirus DNA, commercially available, purchased from Clontech as pBAKPAK8, cat # 6145-1.

(d) Cassette comprising promoter and enhancer elements from Cytomegalovirus and SV40 virus. The cassette was generated by PCR using a derivative of expression vector TCAE8 (Reff et al, *Blood*, 83:435–445 (1994)). The enhancer cassette was inserted within the baculovirus sequence, which was first modified by the insertion of a multiple cloning site.

(e) *E. coli* GUS (glucuronidase) gene, commercially available, purchased from Clontech as pB101, cat. # 6017-1.

(f) *E. coli* luciferase gene, commercially available, obtained from Promega as pGEM-Luc (catalog # E1541).

(g) *S. typhimurium* histidinol dehydrogenase gene (HisD). This gene was originally a gift from (Donahue et el, Gene, 18:47–59 (1982)), and has subsequently been incorporated into a transcription cassette comprising the mouse beta globin major promoter 5' to the gene, and the SV40 polyadenylation signal 3' to the gene.

The DNA elements described in (a)–(g) were combined into a pBR derived plasmid backbone to produce a 7.7 kb contiguous stretch of DNA referred to in the attached figures as "homology". Homology in this sense refers to sequences of DNA which are not part of the mammalian genome and are used to promote homologous recombination between transfected plasmids sharing the same homology DNA sequences.

(h) Neomycin phosphotransferase gene from TN5 (Davis and Smith, *Ann. Rev. Micro.*, 32:469–518 (1978)). The complete neo gene was subcloned into pBluescript SK- (Stratagene catalog # 212205) to facilitate genetic manipulation. A synthetic linker was then inserted into a unique Pst1 site occurring across the codons for amino acid 51 and 52 of neo. This linker encoded the necessary DNA elements to create an artificial splice donor site, intervening intron and splice acceptor site within the neo gene, thus creating two separate exons, presently referred to as neo exon 1 and 2. Neo exon 1 encodes the first 51 amino acids of neo, while exon 2 encodes the remaining 203 amino acids plus the stop codon of the protein A Not1 cloning site was also created within the intron.

Neo exon 2 was further subdivided to produce neo exons 2 and 3. This was achieved as follows: A set of PCR primers were designed to amplify a region of DNA encoding neo exon 1, intron and the first 111 ⅔ amino acids of exon2. The 3' PCR primer resulted in the introduction of a new 5' splice site immediately after the second nucleotide of the codon for amino acid 111 in exon 2, therefore generating a new smaller exon 2. The DNA fragment now encoding the original exon 1, intron and new exon 2 was then subcloned and propagated in a pBR based vector. The remainder of the original exon 2 was used as a template for another round of PCR amplification, which generated "exon3". The 5' primer for this round of amplification introduced a new splice acceptor site at the 5' side of the newly created exon 3, i.e. before the final nucleotide of the codon for amino acid 111. The resultant 3 exons of neo encode the following information: exon 1—the first 51 amino acids of neo; exon 2—the next 111 ⅔ amino acids, and exon 3 the final 91 ⅓ amino acids plus the translational stop codon of the neo gene.

Neo exon 3 was incorporated along with the above mentioned DNA elements into the marking plasmid "Desmond". Neo exons 1 and 2 were incorporated into the targeting plasmid "Molly". The Not1 cloning site created within the intron between exons 1 and 2 was used in subsequent cloning steps to insert genes of interest into the targeting plasmid.

Figure 1B:
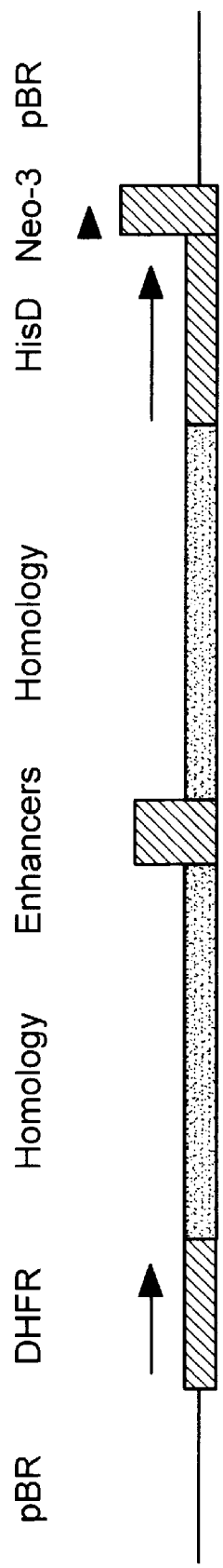
Figure 2B:
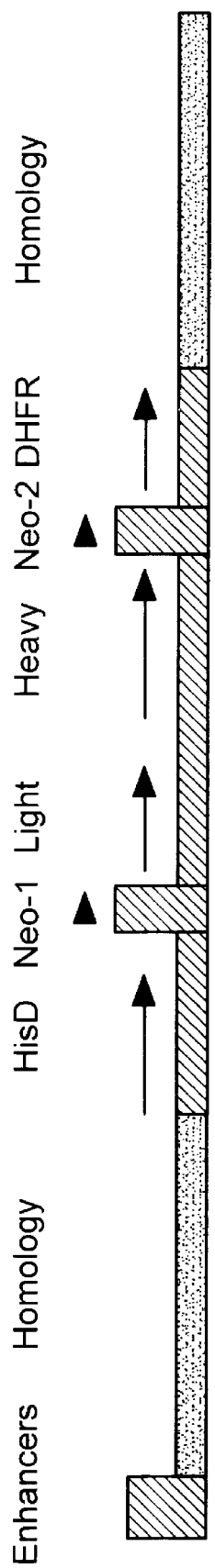
FIG. 2(b) shows a linearized version of Molly, after digestion with the restriction enzymes Kpn1 and Pac1. This linearized form was used for transfection.
Figure 3:
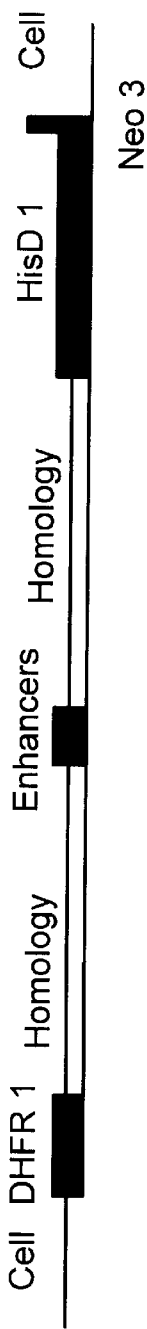
FIG. 3 depicts the potential alignment between Desmond sequences integrated into the CHO genome, and incoming targeting Molly sequences. One potential arrangement of Molly integrated into Desmond after homologous recombination is also presented.
Figure 3:
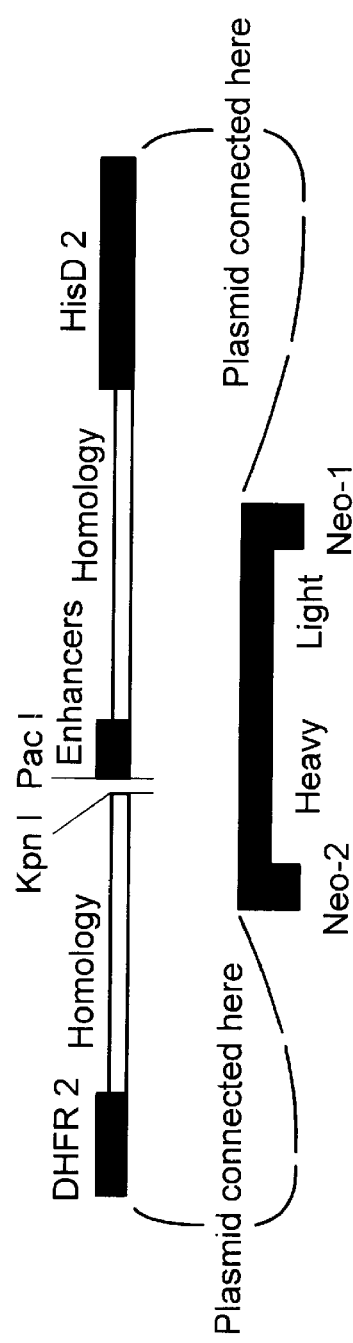
Figure 3:

FIG. 1 depicts the arrangement of these DNA elements in the marker plasmid "Desmond". FIG. 2 depicts the arrangement of these elements in the first targeting plasmid, "Molly". FIG. 3 illustrates the possible arrangement in the CHO genome, of the various DNA elements after targeting and integration of Molly DNA into Desmond marked CHO cells.

Construction of the marking and targeting plasmids from the above listed DNA elements was carried out following conventional cloning techniques (see, e.g., Molecular Cloning, A Laboratory Manual, J. Sambrook et al, 1987, Cold Spring Harbor Laboratory Press, and Current Protocols in Molecular Biology, F. M. Ausubel et al, eds., 1987, John Wiley and Sons). All plasmids were propagated and maintained in *E. coli* XLI blue (Stratagene, cat. # 200236). Large scale plasmid preparations were prepared using Promega WIZARD MAXIPREP DNA PURIFICATION SYSTEM, according to the manufacturer's directions.

EXAMPLE 2

Construction of a Marked CHO Cell Line
1. Cell Culture and Transfection Procedures to Produced Marked CHO Cell Line Marker plasmid DNA was linearized by digestion overnight at 37° C. with Bst1107I. Linearized vector was ethanol precipitated and resuspended in sterile TE to a concentration of 1 mg/ml. Linearized vector was introduced into DHFR- Chinese hamster ovary cells (CHO cells) DG44 cells (Urlaub et al, *Som. Cell* and *Mol. Gen.*, 12:555–566 (1986)) by electroporation as follows.

Exponentially growing cells were harvested by centrifugation, washed once in ice cold SBS (sucrose buffered solution, 272 mM sucrose, 7 mM sodium phosphate, pH 7.4, 1 mM magnesium chloride) then resuspended in SBS to a concentration of $10^7$ cells/ml. After a 15 minute incubation on ice, 0.4 ml of the cell suspension was mixed with 40 μg linearized DNA in a disposable electroporation cuvette. Cells were shocked using a BTX electrocell manipulator (San Diego, Calif.) set at 230 volts, 400 microfaraday capacitance, 13 ohm resistance. Shocked cells were then mixed with 20 ml of prewarmed CHO growth media (CHO-S-SFMII, Gibco/BRL, catalog # 31033-012) and plated in 96 well tissue culture plates. Forty eight hours after electroporation, plates were fed with selection media (in the case of transfection with Desmond, selection media is CHO- S-SFMII without hypoxanthine or thymidine, supplemented with 2 mM Histidinol (Sigma catalog # H6647)). Plates were maintained in selection media for up to 30 days, until colonies appeared. These colonies were then removed from the 96 well plates. Positive clones were expanded to tissue culture flasks and finally to 120 ml spinner flasks, and were maintained in selection media at all times.

EXAMPLE 3

Characterization of Marked CHO Cell Lines
(a) Southern Analysis

Figure 4:
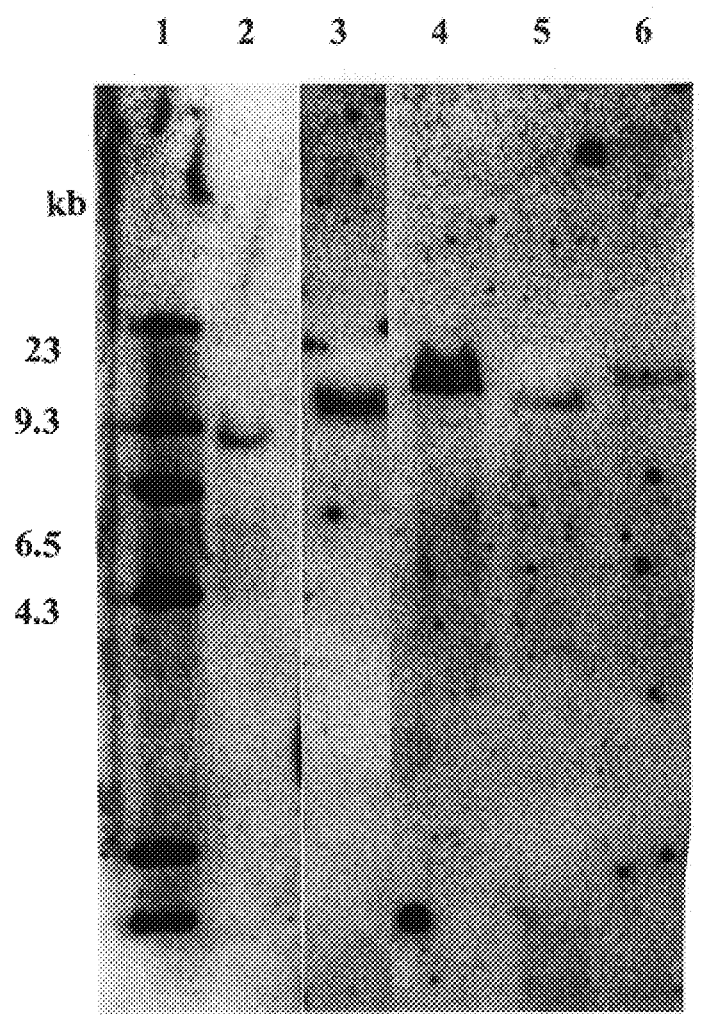
FIG. 4 shows a Southern analysis of single copy Desmond clones. Samples are as follows:
Lane 1: λHindIII DNA size marker
Lane 2: Desmond clone 10F3
Lane 3: Desmond clone 10C12
Lane 4: Desmond clone 15C9
Lane 5: Desmond clone 14B5
Lane 6: Desmond clone 9B2
Figure 5:
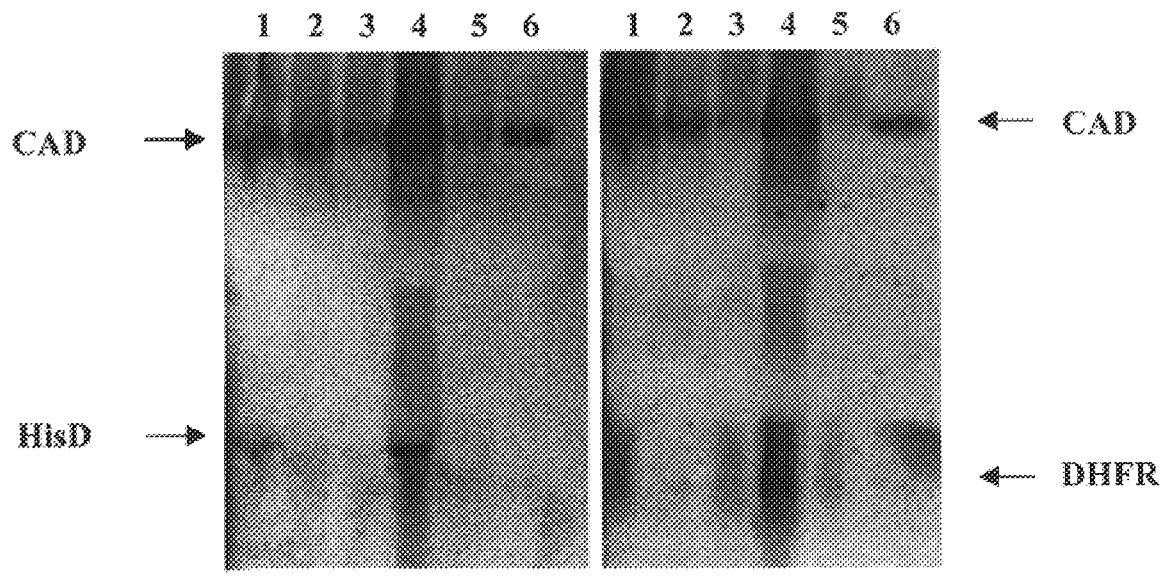
FIG. 5 shows a Northern analysis of single copy Desmond clones. Samples are as follows: Panel A: northern probed with CAD and DHFR probes, as indicated on the figure. Panel B: duplicate northern, probed with CAD and HisD probes, as indicated. The RNA samples loaded in panels A and B are as follows: Lane 1: clone 9B2, lane 2; clone 10C12, lane 3; clone 14B5, lane 4; clone 15C9, lane 5; control RNA from CHO transfected with a HisD and DHFR containing plasmid, lane 6; untransfected CHO.

Genomic DNA was isolated from all stably growing Desmond marked CHO cells. DNA was isolated using the Invitrogen Easy® DNA kit, according to the manufacturer's directions. Genomic DNA was then digested with HindIII overnight at 37° C., and subjected to Southern analysis using a PCR generated digoxygenin labelled probe specific to the DHFR gene. Hybridizations and washes were carried out using Boehringer Mannheim's DIG easy hyb (catalog # 1603 558) and DIG Wash and Block Buffer Set (catalog # 1585 762) according to the manufacturer's directions. DNA samples containing a single band hybridizing to the DHFR probe were assumed to be Desmond clones which had integrated a single copy of the plasmid. These clones were retained for further analysis. Out of a total of 45 HisD resistant clones identified in the experiment, only 5 were single copy integrants. FIG. 4 shows a Southern blot containing all 5 of these single copy Desmond clones. Clone names are provided in the figure legend.
(b) Northern Analysis Total RNA was isolated from all single copy Desmond clones using TRIzol reagent (Gibco/BRL cat # 15596-026) according to the manufacturer's directions. 10–20 μg RNA from each clone was analyzed on duplicate formaldehyde gels. The resulting blots were probed with PCR generated digoxygenin labelled DNA probes to (i) DHFR message, (ii) HisD message and (iii) CAD message. CAD is a trifunctional protein involved in uridine biosynthesis (Wahl et al, *J. Biol. Chem.*, 254, 17:8679–8689 (1979)), and is expressed equally in all cell types. It is used here as an internal control to help quantitate RNA loading. Hybridizations and washes were carried out using the above mentioned Boehringer Mannheim reagents. The results of the Northern analysis are shown in FIG. 5. The single copy Desmond clone exhibiting the highest levels of both the His D and DHFR message is clone 15C9, shown in lane 4 in both panels of the figure. This clone was designated as the "marked cell line" and used in future targeting experiments in CHO, examples of which are presented in the following sections.

EXAMPLE 4

Construction of a Marked SP2/0 Cell Line

In order to demonstrate the utility of this expression system in any cultured mammalian cell, we have created a Desmond marked SP2/0 cell line. SP2/0 cells were grown in suspension culture in PFHM II media (protein-free hybridoma media, Gibco/BRL, cat # 12040–093). Exponentially growing cells were harvested by centrifugation, and all subsequent steps involved in preparation for electroporation, including preparation of Desmond plasmid DNA, were as described in the preceding section on marking CHO cells. Electroporation conditions were varied somewhat: ten electroporations were carried out at 400 volts, 25 µFaradays capacitance and 13 ohms resistance, while an additional 10 were at 350 volts, 50 µFaradays and 13 ohms resistance. Each electroporation was then plated into individual 96 well plates. Selection media for these cells comprised PFHM II supplemented with 10 mM histidinol. Plates were maintained in selection media for 25 days. Resistant colonies were transferred from the 96 well dishes and ultimately expanded to spinner flasks. Experiments are currently ongoing to identify single copy SP2/0 clones containing Desmond integrated in a transcriptionally active site. Future experiments will involve targeting such a site with Molly.

EXAMPLE 5

Expression of Anti-CD20 Antibody in Desmond Marked CHO Cells

C2B8, a chimeric antibody which recognizes B-cell surface antigen CD20, has been cloned and expressed previously in our laboratory. (Reff et al, *Blood*, 83:434–45 (1994)). A 4.1 kb DNA fragment comprising the C2B8 light and heavy chain genes, along with the necessary regulatory elements (eukaryotic promoter and polyadenylation signals) was inserted into the artificial intron created between exons 1 and 2 of the neo gene contained in a pBR derived cloning vector. This newly generated 5 kb DNA fragment (comprising neo exon 1, C2B8 and neo exon 2) was excised and used to assemble the targeting plasmid Molly. The other DNA elements used in the construction of Molly are identical to those used to construct the marking plasmid Desmond, identified previously. A complete map of Molly is shown in FIG. 2.

The targeting vector Molly was linearized prior to transfection by digestion with Kpn1 and Pac1, ethanol precipitated and resuspended in sterile TE to a concentration of 1.5 mg/mL. Linearized plasmid was introduced into exponentially growing Desmond marked cells essentially as described, except that 80 µg DNA was used in each electroporation. Forty eight hours postelectroporation, 96 well plates were supplemented with selection medium—CHO-SSFMII supplemented with 400 µg/mL Geneticin (G418, Gibco/BRL catalog # 10131-019). Plates were maintained in selection medium for up to 30 days, or until viable colonies were obtained. The supernatants from all G418 resistant colonies were assayed for C2B8 production by standard ELISA techniques, and all productive clones were eventually expanded to 120 mL spinner flasks and further analyzed.

Characterization of Antibody secreting Targeted Cells

Figure 6:
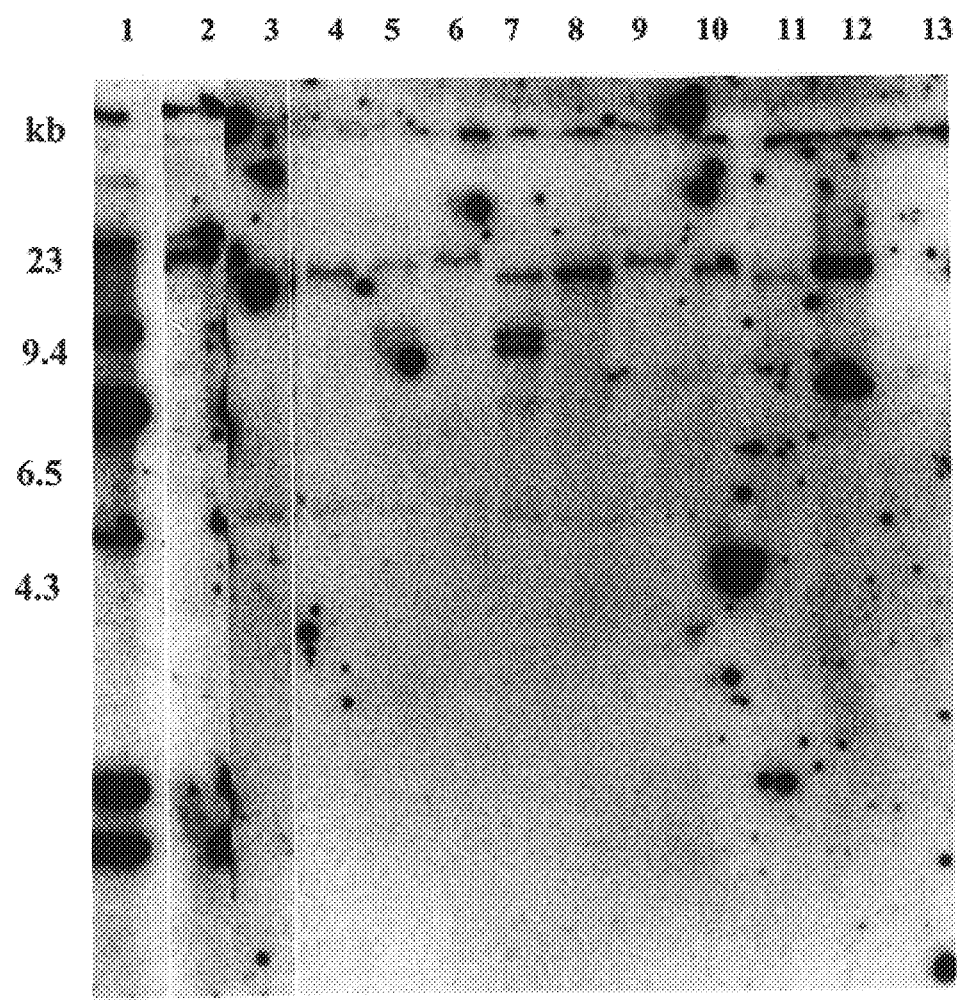
FIG. 6 shows a Southern analysis of clones resulting from the homologous integration of Molly into Desmond. Samples are as follows:
Lane 1: λHindIII DNA size markers, Lane 2: 20F4, lane 3; 5F9, lane 4; 21C7, lane 5; 24G2, lane 6; 25E1, lane 7; 28C9, lane 8; 29F9, lane 9; 39G11, lane 10; 42F9, lane 11; 50G10, lane 12; Molly plasmid DNA, linearized with BglII(top band) and cut with BglII and KpnI (lower band), lane 13; untransfected Desmond.

A total of 50 electroporations with Molly targeting plasmid were carried out in this experiment, each of which was plated into separate 96 well plates. A total of 10 viable, anti-CD20 antibody secreting clones were obtained and expanded to 120 ml spinner flasks. Genomic DNA was isolated from all clones, and Southern analyses were subsequently performed to determine whether the clones represented single homologous recombination events or whether additional random integrations had occurred in the same cells. The methods for DNA isolation and Southern hybridization were as described in the previous section. Genomic DNA was digested with EcoRI and probed with a PCR generated digoxygenin labelled probe to a segment of the CD20 heavy chain constant region. The results of this Southern analysis are presented in FIG. 6. As can be seen in the FIG. 8 of the 10 clones show a single band hybridizing to the CD20 probe, indicating a single homologous recombination event has occurred in these cells. Two of the ten, clones 24G2 and 28V9, show the presence of additional band(s), indicative of an additional random integration elsewhere in the genome.

We examined the expression levels of anti-CD20 antibody in all ten of these clones, the data for which is shown in Table 1, below.

TABLE 1

Expression Level of Anti-CD20 Secreting Homologous Integrants

| Clone | Anti-CD20, pg/c/d |
|---|---|
| 20F4 | 3.5 |
| 21C7 | 1.3 |
| 24G2 | 2.1 |
| 25E1 | 2.4 |
| 28C9 | 4.5 |
| 29F9 | 0.8 |
| 39G11 | 1.5 |
| 42F9 | 1.8 |
| 50G10 | 0.9 |
| 5F9 | 0.3 |

Expresion levels are reported as picogram per cell per day (pg/c/d) secreted by the individual clones, and represented the mean levels obtained from three separate ELISAs on samples taken from 120 mL spinner flasks.

As can be seen from the data, there is a variation in antibody secretion of approximately ten fold between the highest and lowest clones. This was somewhat unexpected as we anticipated similar expression levels from all clones due to the fact the anti-CD20 genes are all integrated into the same Desmond marked site. Nevertheless, this observed range in expression extremely small in comparison to that seen using any traditional random integration method or with our translationally impaired vector system. We are currently investigating mRNA levels of all the clones in order to determine whether this expression range is due to differences in transcription levels. We anticipate that message levels will be similar in all clones and the observed differences in secretion levels among the homologous integrants is not an additional cellular factors which play a role in mediating secretion levels. This will of course be true in any expression system and is not inherent to this homologous system.

Clone 20F4, the highest producing single copy integrant was selected for further study. Table 2 (below) presents ELISA and cell culture data from seven day production runs of this clone.

TABLE 2

7 Day Production Run Data for 20F4

| Day | % Viable | Viable/ml (× 10[5]) | T × 2 (hr) | mg/L | pg/c/d |
|---|---|---|---|---|---|
| 1 | 96 | 3.4 | 31 | 1.3 | 4.9 |
| 2 | 94 | 6 | 29 | 2.5 | 3.4 |
| 3 | 94 | 9.9 | 33 | 4.7 | 3.2 |
| 4 | 90 | 17.4 | 30 | 6.8 | 3 |
| 5 | 73 | 14 | | 8.3 | |
| 6 | 17 | 3.5 | | 9.5 | |

Clone 20F4 was seeded at 2 × 10[5] ml in a 120 ml spinner flask on day 0. On the following six days, cell counts were taken, doubling times calculated and 1 ml samples of supernatant removed from the flask and analyzed for secreted anti-CD20 by ELISA.

This clone is secreting on average, 3–5 pg antibody/-cell/day, based on this ELISA data. This is the same level as obtained from other high expressing single copy clones obtained previously in our laboratory using the previously developed translationally impaired random integration vectors. This result indicates the following:

(1) that the site in the CHO genome marked by the Desmond marking vector is highly transcriptionally active, and therefore represents an excellent site from which to express recombinant proteins, and (2) that targeting by means of homologous recombination can be accomplished using the subject vectors and occurs at a frequency high enough to make this system a viable and desirable alternative to random integration methods.

To further demonstrate the efficacy of this system, we have also demonstrated that this site is amplifiable, resulting in even higher levels of gene expression and protein secretion. Amplification was achieved by plating serial dilutions of 20F4 cells, starting at a density of $2.5 \times 10^4$ cells/ml, in 96 well tissue culture dishes, and culturing these cells in media (CHO-SSFMII) supplemented with 5, 10, 15 or 20 nM methotrexate. Antibody secreting clones were screened using standard ELISA techniques, and the highest producing clones were expanded and further analyzed. A summary of this amplification experiment is presented in Table 3 below.

TABLE 3

Summary of 20F4 Amplification

| nM MTX | # Clones Assayed | Expression Level mg/l 96 well | # Clones Expanded | Expression Level pg/c/d from spinner |
|---|---|---|---|---|
| 10 | 56 | 3–13 | 4 | 10–15 |
| 15 | 27 | 2–14 | 3 | 15-18 |
| 20 | 17 | 4–11 | 1 | ND |

Methotrexate amplification of 20F4 was set up as described in the text, using the concentrations of methotrexate indicated in the above table. Supernatants from all surviving 96 well colonies were assayed by ELISA, and the range of anti-CD20 expressed by these clones is indicated in column 3. Based on these results, the highest producing clones were expanded to 120 ml spinners and several ELISAs conducted on the spinner supernatants to determine the pg/cell/day expression levels, reported in column 5.

The data here clearly demonstrates that this site can be amplified in the presence of methotrexate. Clones from the 10 and 15 nM amplifications were found to produce on the order of 15–20 pg/cell/day. It is anticipated that subsequent rounds of amplification on this clone will achieve higher levels, on the order of 60–100 pg/cell/-day, which is approaching the maximum secretion capacity of immunoglobulin in mammalian cells (Reff, M. E., Curr. Opin. Biotech., 4:573–576 (1993)). Further amplification of this clone is currently ongoing.

Example 6

Expression of Anti-Human CD23 Antibody in Desmond Marked CHO Cells

CD23 is low affinity IgE receptor which mediates binding of IgE to B and T lymphocytes (Sutton, B. J., and Gould, H. J., Nature, 366:421–428 (1993)). Anti-human CD23 monoclonal antibody 5E8 is a human gamma-1 monoclonal antibody recently cloned and expressed in our laboratory. This antibody is disclosed in commonly assigned Ser. No. 08/803,085, filed on Feb. 20, 1997.

The heavy and light chain genes of 5E8 were cloned into the mammalian expression vector N5KG1, a derivative of the vector NEOSPLA (Barnett et al, in Antibody Expression and Engineering, H.Y Yang and T. Imanaka, eds., pp27–40 (1995)) and two modifications were then made to the genes. We have recently observed somewhat higher secretion of immunoglobulin light chains compared to heavy chains in other expression constructs in the laboratory (Reff et al, 1997, unpublished observations). In an attempt to compensate for this deficit, we altered the 5E8 heavy chain gene by the addition of a stronger promoter/enhancer element immediately upstream of the start site. Subsequently, a 2.9 kb DNA fragment comprising the 5E8 modified light and heavy chain genes was isolated from the N5KG1 vector and inserted between the BglII and SacII sites in the targeting vector Molly. Preparation of 5E8-containing Molly and electroporation into Desmond 15C9 CHO cells was exactly as described in the preceding section. In this experiment, 20 electroporations were performed and plated into 96 well tissue culture dishes. Three anti-CD23 antibody secreting homologous clones were isolated and expanded to 120 ml spinner flasks. The levels of antibody secretion obtained from these clones ranged from 2–4 pg/cell/day, in close agreement with the expression levels observed for anti-CD20. Methotrexate amplification of the highest anti-CD23 expressing clone is currently underway.

EXAMPLE 7

Expression of Immunoadhesin in Desmond Marked CHO Cells

CTLA-4, a member of the Ig superfamily, is found on the surface of T lymphocytes and is thought to play a role in antigen-specific T-cell activation (Dariavach et al, Eur. J. Immunol., 18:1901–1905 (1988); and Linsley et al, J. Exp. Med., 174:561–569 (1991)). In order to further study the precise role of the CTLA-4 molecule in the activation pathway, a soluble fusion protein comprising the extracellular domain of CTLA-4 linked to a truncated form of the human IgG1 constant region was created (Linsley et al (Id.). We have recently expressed this CTLA-4 Ig fusion protein in the mammalian expression vector BLECH1, a derivative of the plasmid NEOSPLA (Barnett et al, in Antibody Expression and Engineering, H.Y Yang and T. Imanaka, eds., pp27–40 (1995)). An 800 bp fragment encoding the CTLA-4 Ig was isolated from this vector and inserted between the SacII and BglII sites in Molly.

Preparation of CTLA-4Ig-Molly and electroporation into Desmond clone 15C9 CHO cells was performed as described in the preceding section. Twenty electroporations were carried out, and plated into 96 well culture dishes as described previously. Eighteen CTLA-4 expressing clones were isolated from the 96 well plates and carried forward to the 120 ml spinner stage. Southern analyses on genomic DNA isolated from each of these clones was then carried out to determine how many of the homologous clones contained additional random integrants. Genomic DNA was digested with BglII and probed with a PCR generated digoxygenin labelled probe to the human IgG1 constant region. The results of this analysis indicated that 85% of the CTLA-4 clones are homologous integrants only; the remaining 15% contained one additional random integrant. This result corroborates the findings from the expression of anti-CD20 discussed above, where 80% of the clones were single homologous integrants. Therefore, we can conclude that this expression system reproducibly yields single targeted homologous integrants in at least 80% of all clones produced.

Expression levels for the homologous CTlA4-Ig clones ranged from 8–12 pg/cell/day. This is somewhat higher than the range reported for anti-CD20 antibody and anti-CD23 antibody clones discussed above. However, we have previously observed that expression of this molecule using the intronic insertion vector system also resulted in significantly higher expression levels than are obtained for immunoglobulins. We are currently unable to provide an explanation for this observation.

Example 8

Targeting Anti-CD20 to an alternate Desmond Marked CHO Cell Line

As we described in a preceding section, we obtained 5 single copy Desmond marked CHO cell lines (see FIGS. 4 and 5). In order to demonstrate that the success of our targeting strategy is not due to some unique property of Desmond clone 15C9 and limited only to this clone, we introduced anti-CD20 Molly into Desmond clone 9B2 (lane 6 in FIG. 4, lane 1 in FIG. 5). Preparation of Molly DNA and electroporation into Desmond 9B2 was exactly as described in the previous sections. We obtained one homologous integrant from this experiment. This clone was expanded to a 120 ml spinner flask, where it produced on average 1.2 pg anti-CD20/cell/day. This is considerably lower expression than we observed with Molly targeted into Desmond 15C9. However, this was the anticipated result, based on our northern analysis of the Desmond clones. As can be seen in FIG. 5, mRNA levels from clone 9B2 are considerably lower than those from 15C9, indicating the site in this clone is not as transcriptionally active as that in 15C9. Therefore, this experiment not only demonstrates the reproducibility of the system—presumably any marked Desmond site can be targeted with Molly—it also confirms the northern data that the site in Desmond 15C9 is the most transcriptionally active.

From the foregoing, it will be appreciated that, although specific embodiments of the invention have been described herein for purposes of illustration, various modifications may be made without diverting from the scope of the invention. Accordingly, the invention is not limited by the appended claims.

What is claimed is:

1. A method for inserting a desired DNA at a target site in the genome of a mammalian cell which comprises the following steps:
   (i) transfecting or transforming a mammalian cell with a first plasmid ("marker plasmid") containing the following sequences:
      (a) a region of DNA that is heterologous to the mammalian cell genome which when integrated in the mammalian cell genome provides a unique site for homologous recombination;
      (b) a DNA fragment encoding at least one exon of a first dominant selectable marker protein; and
      (c) at least one other selectable marker DNA that encodes an additional marker protein that provides for selection of mammalian cells which have been successfully integrated with the marker plasmid;
   (ii) selecting a cell which contain the marker plasmid integrated in its genome;
   (iii) transfecting or transforming said selected cell with a second plasmid ("target plasmid") which contains the following sequences:
      (a) a region of DNA that is identical or is sufficiently homologous to the unique site for homologous recombination contained in the marker plasmid such that this region of DNA can recombine with said unique site DNA via homologous recombination;
      (b) a DNA fragment encoding a portion of said first dominant selectable marker contained in the marker plasmid, wherein active selectable marker protein is only produced if said fragment of said first dominant selectable marker DNA contained in the target plasmid is expressed in association with said at least one exon of said first dominant selectable marker DNA contained in the marker plasmid; and
   (iv) selecting cells which contain the target plasmid integrated at the target site by screening for the expression of said first dominant selectable marker protein.

2. The method of claim 1, wherein the target plasmid contains the remaining exons of said first dominant selectable marker.

3. The method of claim 2, wherein at least one DNA encoding a desired protein is inserted between said remaining exons of said first dominant selectable marker contained in the target plasmid.

4. The method claim 3, wherein a DNA encoding a different dominant selectable marker is further inserted between the exons of said first dominant selectable marker contained in the target plasmid to provide for co-amplification of the DNA encoding the desired protein.

5. The method of claim 2, wherein said first dominant selectable marker is selected from the group consisting of neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase.

6. The method of claim 3, wherein the desired protein is a mammalian protein.

7. The method of claim 6, wherein the protein is an immunoglobulin.

8. The method of claim 1, which further comprises determining the expression level of the first dominant selectable marker contained in the marker plasmid prior to integration of the target vector.

9. The method of claim 8, wherein the other selectable marker that encodes an additional marker protein contained in the plasmid is a dominant selectable marker selected from the group consisting of histidinol dehydrogenase, herpes simplex thymidine kinase, hydromycin phosphotransferase, adenosine deaminase, and glutamine synthetase.

10. The method of claim 1, wherein the mammalian cell is selected from the group consisting of Chinese hamster ovary (CHO) cells, myeloma cells, baby hamster kidney cells, COS cells, NSO cells, HeLa cells, and NIH 3T3 cells.

11. The method of claim 10, wherein the cell is a CHO cell.

12. The method of claim 1, wherein said at least one exon of said first dominant selectable marker contained in the marker plasmid is the third exon of a neomycin phosphotransferase gene and the remaining exons of said first dominant selectable marker contained in the target plasmid are the first two exons of the neomycin phosphotransferase gene.

13. The method of claim 1, wherein the marker plasmid further contains a rare restriction endonuclease sequence which is inserted within the region of homology.

14. The method of claim 1, wherein the unique site for homologous recombination is a bacterial DNA, a viral DNA or a synthetic DNA.

15. The method of claim 1, wherein the unique site for homologous recombination is at least 300 nucleotides.

16. The method of claim 15, wherein the unique site for homologous recombination ranges in size from about 300 nucleotides to 20 kilobases.

17. The method of claim 16, wherein the unique site for homologous recombination ranges in size from 2 to 10 kilobases.

18. The method of claim 1, wherein the first selectable marker DNA is split into at least three exons.

19. The method of claim 1, wherein the unique region of DNA that provides for homologous recombination is a bacterial DNA, an insect DNA, a viral DNA or a synthetic DNA.

20. The method of claim 19, wherein the unique region of DNA does not contain any functional genes.

21. A kit for inserting a desired DNA at a target site in the genome of a mammalian cell which comprises at least the following:
   (i) a first plasmid ("marker plasmid") containing at least the following sequences:
      (a) a region of DNA that is heterologous to the mammalian cell genome which when integrated in the mammalian cell genome provides a unique site for homologous recombination;
      (b) a DNA fragment encoding at least one exon of a first dominant selectable marker protein; and
      (c) at least one other selectable marker DNA that provides for selection of mammalian cells which have been successfully integrated with the marker plasmid; and
   (ii) a second plasmid ("target plasmid") which contains at least the following sequences:
      (a) a region of DNA that is identical or is sufficiently homologous to the unique site for homologous recombination in the marker plasmid such that this region of DNA can recombine with said unique site via homologous recombination;
      (b) a DNA fragment encoding a portion of said first dominant selectable marker contained in the marker plasmid, wherein said first selectable marker protein is only produced in active form if said DNA fragment of said first dominant selectable marker in the target plasmid which is expressed in association with said at least one exon of said first dominant selectable marker DNA contained in the marker plasmid.

22. The kit of claim 21, wherein the target plasmid contains the remaining exons of said first selectable marker.

23. The kit of claim 22, wherein at least one DNA encoding a desired protein is inserted between said exons of said first selectable marker contained in the target plasmid.

24. The kit of claim 22, wherein a DNA encoding a different dominant selectable marker is further inserted between the exons of said first selectable marker contained in the target plasmid to provide for co-amplification of the DNA encoding the desired protein.

25. The kit of claim 22, wherein the first dominant selectable marker is selected from the group consisting of neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase.

26. The kit of claim 23, wherein the desired protein is a mammalian protein.

27. The kit of claim 26, wherein the protein is an immunoglobulin.

28. The kit of claim 21, wherein the other selectable marker contained in the marker plasmid is a dominant selectable marker selected from the group consisting of histidinol dehydrogenase, herpes simplex thymidine kinase, hydromycin phosphotransferase, adenosine deaminase, and glutamine synthetase.

29. The kit of claim 21, which provides for insertion of a desired DNA at a targeted site in the genome of a mammalian cell selected from the group consisting of Chinese hamster ovary (CHO) cells, myeloma cells, baby hamster kidney cells, COS cells, NSO cells, HeLa cells, and NIH 3T3 cells.

30. The kit of claim 29, wherein the mammalian cell is a CHO cell.

31. The kit of claim 22, wherein said at least one exon of said first dominant selectable marker contained in the marker plasmid is the third exon of a neomycin phosphotransferase gene and the remaining exons of said first dominant selectable marker contained in the target plasmid are the first two exons of the neomycin phosphotransferase gene.

32. The kit of claim 21, wherein the marker plasmid further contains a rare restriction endonuclease sequence which is inserted within the unique site for homologous recombination.

33. The kit of claim 21, wherein the unique site contained in the marker plasmid that provides for homologous recombination is at least 300 nucleotides.

34. The kit of claim 33, wherein said unique site ranges in size from about 300 nucleotides to 20 kilobases.

35. The kit of claim 34, wherein said unique site ranges in size from 2 to 10 kilobases.

36. The kit of claim 21, wherein the first selectable marker DNA is split into at least three exons.

37. The kit of claim 21, wherein said unique site that provides for homologous recombination is a bacterial DNA, an insect DNA, a viral DNA, or a synthetic DNA.

38. The kit of claim 37, wherein said unique site does not contain any functional genes.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 14683 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
TTTCTAGACC  TAGGGCGGCC  AGCTAGTAGC  TTTGCTTCTC  AATTTCTTAT  TTGCATAATG     60

AGAAAAAAAG  GAAAATTAAT  TTTAACACCA  ATTCAGTAGT  TGATTGAGCA  AATGCGTTGC    120

CAAAAGGAT   GCTTTAGAGA  CAGTGTTCTC  TGCACAGATA  AGGACAAACA  TTATTCAGAG    180

GGAGTACCCA  GAGCTGAGAC  TCCTAAGCCA  GTGAGTGGCA  CAGCATTCTA  GGGAGAAATA    240

TGCTTGTCAT  CACCGAAGCC  TGATTCCGTA  GAGCCACACC  TTGGTAAGGG  CCAATCTGCT    300

CACACAGGAT  AGAGAGGGCA  GGAGCCAGGG  CAGAGCATAT  AAGGTGAGGT  AGGATCAGTT    360

GCTCCTCACA  TTTGCTTCTG  ACATAGTTGT  GTTGGGAGCT  TGGATAGCTT  GGACAGCTCA    420

GGGCTGCGAT  TTCGCGCCAA  ACTTGACGGC  AATCCTAGCG  TGAAGGCTGG  TAGGATTTTA    480

TCCCCGCTGC  CATCATGGTT  CGACCATTGA  ACTGCATCGT  CGCCGTGTCC  CAAAATATGG    540

GGATTGGCAA  GAACGGAGAC  CTACCCTGGC  CTCCGCTCAG  GAACGAGTTC  AAGTACTTCC    600

AAAGAATGAC  CACAACCTCT  TCAGTGGAAG  GTAAACAGAA  TCTGGTGATT  ATGGGTAGGA    660
```

-continued

| | | | | | | |
|---|---|---|---|---|---|---|
| AAACCTGGTT | CTCCATTCCT | GAGAAGAATC | GACCTTTAAA | GGACAGAATT | AATATAGTTC | 720 |
| TCAGTAGAGA | ACTCAAAGAA | CCACCACGAG | GAGCTCATTT | TCTTGCCAAA | AGTTTGGATG | 780 |
| ATGCCTTAAG | ACTTATTGAA | CAACCGGAAT | TGGCAAGTAA | AGTAGACATG | GTTTGGATAG | 840 |
| TCGGAGGCAG | TTCTGTTTAC | CAGGAAGCCA | TGAATCAACC | AGGCCACCTT | AGACTCTTTG | 900 |
| TGACAAGGAT | CATGCAGGAA | TTTGAAAGTG | ACACGTTTTT | CCCAGAAATT | GATTTGGGGA | 960 |
| AATATAAACT | TCTCCCAGAA | TACCCAGGCG | TCCTCTCTGA | GGTCCAGGAG | GAAAAAGGCA | 1020 |
| TCAAGTATAA | GTTTGAAGTC | TACGAGAAGA | AAGACTAACA | GGAAGATGCT | TTCAAGTTCT | 1080 |
| CTGCTCCCCT | CCTAAAGCTA | TGCATTTTTA | TAAGACCATG | GGACTTTTGC | TGGCTTTAGA | 1140 |
| TCAGCCTCGA | CTGTGCCTTC | TAGTTGCCAG | CCATCTGTTG | TTTGCCCCTC | CCCCGTGCCT | 1200 |
| TCCTTGACCC | TGGAAGGTGC | CACTCCCACT | GTCCTTTCCT | AATAAAATGA | GGAAATTGCA | 1260 |
| TCGCATTGTC | TGAGTAGGTG | TCATTCTATT | CTGGGGGGTG | GGGTGGGGCA | GGACAGCAAG | 1320 |
| GGGGAGGATT | GGGAAGACAA | TAGCAGGCAT | GCTGGGGATG | CGGTGGGCTC | TATGGAACCA | 1380 |
| GCTGGGGCTC | GAAGCGGCCG | CCCATTTCGC | TGGTGGTCAG | ATGCGGGATG | GCGTGGGACG | 1440 |
| CGGCGGGGAC | CGTCACACTG | AGGTTTTCCG | CCAGACGCCA | CTGCTGCCAG | GCGCTGATGT | 1500 |
| GCCCGGCTTC | TGACCATGCG | GTCGCGTTCG | GTTGCACTAC | GCGTACTGTG | AGCCAGAGTT | 1560 |
| GCCCGGCGCT | CTCCGGCTGC | GGTAGTTCAG | GCAGTTCAAT | CAACTGTTTA | CCTTGTGGAG | 1620 |
| CGACATCCAG | AGGCACTTCA | CCGCTTGCTA | GCGGCTTACC | ATCCAGCGCC | ACCATCCAGT | 1680 |
| GCAGGAGCTC | GTTATCGCTA | TGACGGAACA | GGTATTCGCT | GGTCACTTCG | ATGGTTTGCC | 1740 |
| CGGATAAACG | GAACTGGAAA | AACTGCTGCT | GGTGTTTTGC | TTCCGTCAGC | GCTGGATGCG | 1800 |
| GCGTGCGGTC | GGCAAAGACC | AGACCGTTCA | TACAGAACTG | GCGATCGTTC | GGCGTATCAC | 1860 |
| CAAAATCACC | GCCGTAAGCC | GACCACGGGT | TGCCGTTTTC | ATCATATTTA | ATCAGCGACT | 1920 |
| GATCCACCCA | GTCCCAGACG | AAGCCGCCCT | GTAAACGGGG | ATACTGACGA | AACGCCTGCC | 1980 |
| AGTATTTAGC | GAAACCGCCA | AGACTGTTAC | CCATCGCGTG | GGCGTATTCG | CAAAGGATCA | 2040 |
| GCGGGCGCGT | CTCTCCGGGT | AGCGAAAGCC | ATTTTTTGAT | GGACCATTTC | GGACCAGCCG | 2100 |
| GGAAGGGCTG | GTCTTCATCC | ACGCGCGCGT | ACATCGGGCA | AATAATATCG | GTGGCCGTGG | 2160 |
| TGTCGGCTCC | GCCGCCTTCA | TACTGCACCG | GGCGGGAAGG | ATCGACAGAT | TTGATCCAGC | 2220 |
| GATACAGCGC | GTCGTGATTA | GCGCCGTGGC | CTGATTCATT | CCCCAGCGAC | CAGATGATCA | 2280 |
| CACTCGGGTG | ATTACGATCG | CGCTGCACCA | TTCGCGTTAC | GCGTTCGCTC | ATCGCCGGTA | 2340 |
| GCCAGCGCGG | ATCATCGGTC | AGACGATTCA | TTGGCACCAT | GCCGTGGGTT | TCAATATTGG | 2400 |
| CTTCATCCAC | CACATACAGG | CCGTAGCGGT | CGCACAGCGT | GTACCACAGC | GGATGGTTCG | 2460 |
| GATAATGCGA | ACAGCGCACG | GCGTTAAAGT | TGTTCTGCTT | CATCAGCAGG | ATATCCTGCA | 2520 |
| CCATCGTCTG | CTCATCCATG | ACCTGACCAT | GCAGAGGATG | ATGCTCGTGA | CGGTTAACGC | 2580 |
| CTCGAATCAG | CAACGGCTTG | CCGTTCAGCA | GCAGCAGACC | ATTTCCAATC | CGCACCTCGC | 2640 |
| GGAAACCGAC | ATCGCAGGCT | TCTGCTTCAA | TCAGCGTGCC | GTCGGCGGTG | TGCAGTTCAA | 2700 |
| CCACCGCACG | ATAGAGATTC | GGGATTTCGG | CGCTCCACAG | TTTCGGGTTT | TCGACGTTCA | 2760 |
| GACGCAGTGT | GACGCGATCG | GCATAACCAC | CAGGCTCATC | GATAATTTCA | CCGCCGAAAG | 2820 |
| GCGCGGTGCC | GCTGGCGACC | TGCGTTTCAC | CCTGCCATAA | AGAAACTGTT | ACCCGTAGGT | 2880 |
| AGTCACGCAA | CTCGCCGCAC | ATCTGAACTT | CAGCCTCCAG | TACAGCGCGG | CTGAAATCAT | 2940 |
| CATTAAAGCG | AGTGGCAACA | TGGAAATCGC | TGATTTGTGT | AGTCGGTTTA | TGCAGCAACG | 3000 |
| AGACGTCACG | GAAAATGCCG | CTCATCCGCC | ACATATCCTG | ATCTTCCAGA | TAACTGCCGT | 3060 |

| | | | | | | |
|---|---|---|---|---|---|---|
| CACTCCAACG | CAGCACCATC | ACCGCGAGGC | GGTTTTCTCC | GGCGCGTAAA | AATGCGCTCA | 3120 |
| GGTCAAATTC | AGACGGCAAA | CGACTGTCCT | GGCTGTAACC | GACCCACGCC | CCGTTGCACC | 3180 |
| ACAGATGAAA | CGCCGAGTTA | ACGCCATCAA | AAATAATTCG | CGTCTGGCCT | TCCTGTAGCC | 3240 |
| AGCTTTCATC | AACATTAAAT | GTGAGCGAGT | AACAACCCGT | CGGATTCTCC | GTGGGAACAA | 3300 |
| ACGGCGGATT | GACCGTAATG | GGATAGGTTA | CGTTGGTGTA | GATGGGCGCA | TCGTAACCGT | 3360 |
| GCATCTGCCA | GTTTGAGGGG | ACGACGACAG | TATCGGCCTC | AGGAAGATCG | CACTCCAGCC | 3420 |
| AGCTTTCCGG | CACTGCTTCT | GGTGCCGGAA | ACCAGGCAAA | GCGCCATTCG | CCATTCAGGC | 3480 |
| TGCGCAACTG | TTGGGAAGGG | CGATCGGTGC | GGGCCTCTTC | GCTATTACGC | CAGCTGGCGA | 3540 |
| AAGCGGGATG | TGCTGCAAGG | CGATTAAGTT | GGGTAACGCC | AGGGTTTTCC | CAGTCACGAC | 3600 |
| GTTGTAAAAC | GACTTAATCC | GTCGAGGGGC | TGCCTCGAAG | CAGACGACCT | TCCGTTGTGC | 3660 |
| AGCCAGCGGC | GCCTGCGCCG | GTGCCCACAA | TCGTGCGCGA | ACAAACTAAA | CCAGAACAAA | 3720 |
| TCATACCGGC | GGCACCGCCG | CCACCACCTT | CTCCTGTGCC | TAACATTCCA | GCGCCTCCAC | 3780 |
| CACTACCACC | ACCATCGATG | TCTGAATTGC | CGCCCGCTCC | ACCAATGCCG | ACGGAACCTC | 3840 |
| AACCCGCTGC | ACCTTTAGAC | GACAGACAAC | AATTGTTGGA | AGCTATTAGA | AACGAAAAAA | 3900 |
| ATCGCACTCG | TCTCAGACCG | GCTCTCTTAA | GGTAGCTCAA | ACCAAAAACG | GCGCCCGAAA | 3960 |
| CCAGTACAAT | AGTTGAGGTG | CCGACTGTGT | TGCCTAAAGA | GACATTTGAG | CTTAAACCGC | 4020 |
| CGTCTGCACC | ACCGCCACCA | CCTCCGCCTC | CGCCTCCGCC | GCCAGCCCCG | CCTGCGCCTC | 4080 |
| CACCGATGGT | AGATTCATCA | TCAGCTCCAC | CACCGCCGCC | ATTAGTAGAT | TTGCCGTCTG | 4140 |
| AAATGTTACC | ACCGCCTGCA | CCATCGCTTT | CTAACGTGTT | GTCTGAATTA | AAATCGGGCA | 4200 |
| CAGTTAGATT | GAAACCCGCC | CAAAAACGCC | CGCAATCAGA | AATAATTCCA | AAAAGCTCAA | 4260 |
| CTACAAATTT | GATCGCGGAC | GTGTTAGCCG | ACACAATTAA | TAGGCGTCGT | GTGGCTATGG | 4320 |
| CAAAATCGTC | TTCGGAAGCA | ACTTCTAACG | ACGAGGGTTG | GGACGACGAC | GATAATCGGC | 4380 |
| CTAATAAAGC | TAACACGCCC | GATGTTAAAT | ATGTCCAAGC | TACTAGTGGT | ACCTTAATTA | 4440 |
| AGGGGCGGAG | AATGGGCGGA | ACTGGGCGGA | GTTAGGGGCG | GGATGGGCGG | AGTTAGGGGC | 4500 |
| GGGACTATGG | TTGCTGACTA | ATTGAGATGC | ATGCTTTGCA | TACTTCTGCC | TGCTGGGGAG | 4560 |
| CCTGGGGACT | TTCCACACCT | GGTTGCTGAC | TAATTGAGAT | GCATGCTTTG | CATACTTCTG | 4620 |
| CCTGCTGGGG | AGCCTGGGGA | CTTTCCACAC | CCTAACTGAC | ACACATTCCA | CAGAATTAAT | 4680 |
| TCCCCTAGTT | ATTAATAGTA | ATCAATTACG | GGGTCATTAG | TTCATAGCCC | ATATATGGAG | 4740 |
| TTCCGCGTTA | CATAACTTAC | GGTAAATGGC | CCGCCTGGCT | GACCGCTCAA | CGACCCCCGC | 4800 |
| CCATTGACGT | CAATAATGAC | GTATGTTCCC | ATAGTAACGC | CAATAGGGAC | TTTCCATTGA | 4860 |
| CGTCAATGGG | TGGACTATTT | ACGGTAAACT | GCCCACTTGG | CAGTACATCA | AGTGTATCAT | 4920 |
| ATGCCAAGTA | CGCCCCCTAT | TGACGTCAAT | GACGGTAAAT | GGCCCGCCTG | GCATTATGCC | 4980 |
| CAGTACATGA | CCTTATGGGA | CTTTCCTACT | TGGCAGTACA | TCTACGTATT | AGTCATCGCT | 5040 |
| ATTACCATGG | TGATGCGGTT | TTGGCAGTAC | ATCAATGGGC | GTGGATAGCG | GTTTGACTCA | 5100 |
| CGGGGATTTC | CAAGTCTCCA | CCCCATTGAC | GTCAATGGGA | GTTTGTTTTG | AAGCTTGGCC | 5160 |
| GGCCATATAA | ACGGCGGCCA | GCTTTATTTA | ACGTGTTTAC | GTCGAGTCAA | TTGTACACTA | 5220 |
| ACGACAGTGA | TGAAAGAAAT | ACAAAAGCGC | ATAATATTTT | GAACGACGTC | GAACCTTTAT | 5280 |
| TACAAAACAA | AACACAAACG | AATATCGACA | AAGCTAGATT | GCTGCTACAA | GATTTGGCAA | 5340 |
| GTTTTGTGGC | GTTGAGCGAA | AATCCATTAG | ATAGTCCAGC | CATCGGTTCG | GAAAAACAAC | 5400 |
| CCTTGTTTGA | AACTAATCGA | AACCTATTTT | ACAAATCTAT | TGAGGATTTA | ATATTTAAAT | 5460 |

| | | | | | | |
|---|---|---|---|---|---|---|
| TCAGATATAA | AGACGCTGAA | AATCATTTGA | TTTTCGCTCT | AACATACCAC | CCTAAAGATT | 5520 |
| ATAAATTTAA | TGAATTATTA | AAATACATCA | GCAACTATAT | ATTGATAGAC | ATTTCCAGTT | 5580 |
| TGTGATATTA | GTTTGTGCGT | CTCATTACAA | TGGCTGTTAT | TTTTAACAAC | AAACAACTGC | 5640 |
| TCGCAGACAA | TAGTATAGAA | AAGGGAGGTG | AACTGTTTTT | GTTTAACGGT | TCGTACAACA | 5700 |
| TTTTGGAAAG | TTATGTTAAT | CCGGTGCTGC | TAAAAAATGG | TGTAATTGAA | CTAGAAGAAG | 5760 |
| CTGCGTACTA | TGCCGGCAAC | ATATTGTACA | AAACCGACGA | TCCCAAATTC | ATTGATTATA | 5820 |
| TAAATTTAAT | AATTAAAGCA | ACACACTCCG | AAGAACTACC | AGAAATAGC | ACTGTTGTAA | 5880 |
| ATTACAGAAA | AACTATGCGC | AGCGGTACTA | TACACCCCAT | TAAAAAAGAC | ATATATATTT | 5940 |
| ATGACAACAA | AAAATTTACT | CTATACGATA | GATACATATA | TGGATACGAT | AATAACTATG | 6000 |
| TTAATTTTTA | TGAGGAGAAA | AATGAAAAAG | AGAAGGAATA | CGAAGAAGAA | GACGACAAGG | 6060 |
| CGTCTAGTTT | ATGTGAAAAT | AAAATTATAT | TGTCGCAAAT | TAACTGTGAA | TCATTTGAAA | 6120 |
| ATGATTTTAA | ATATTACCTC | AGCGATTATA | ACTACGCGTT | TTCAATTATA | GATAACACTA | 6180 |
| CAAATGTTCT | TGTTGCGTTT | GGTTTGTATC | GTTAATAAAA | AACAAATTTA | GCATTTATAA | 6240 |
| TTGTTTTATT | ATTCAATAAT | TACAAATAGG | ATTGAGACCC | TTGCAGTTGC | CAGCAAACGG | 6300 |
| ACAGAGCTTG | TCGAGGAGAG | TTGTTGATTC | ATTGTTTGCC | TCCTGCTGC | GGTTTTTGAC | 6360 |
| CGAAGTTCAT | GCCAGTCCAG | CGTTTTTGCA | GCAGAAAAGC | CGCCGACTTC | GGTTTGCGGT | 6420 |
| CGCGAGTGAA | GATCCCTTTC | TTGTTACCGC | CAACGCGCAA | TATGCCTTGC | GAGGTCGCAA | 6480 |
| AATCGGCGAA | ATTCCATACC | TGTTCACCGA | CGACGGCGCT | GACGCGATCA | AAGACGCGGT | 6540 |
| GATACATATC | CAGCCATGCA | CACTGATACT | CTTCACTCCA | CATGTCGGTG | TACATTGAGT | 6600 |
| GCAGCCCGGC | TAACGTATCC | ACGCCGTATT | CGGTGATGAT | AATCGGCTGA | TGCAGTTTCT | 6660 |
| CCTGCCAGGC | CAGAAGTTCT | TTTTCCAGTA | CCTTCTCTGC | CGTTTCCAAA | TCGCCGCTTT | 6720 |
| GGACATACCA | TCCGTAATAA | CGGTTCAGGC | ACAGCACATC | AAAGAGATCG | CTGATGGTAT | 6780 |
| CGGTGTGAGC | GTCGCAGAAC | ATTACATTGA | CGCAGGTGAT | CGGACGCGTC | GGGTCGAGTT | 6840 |
| TACGCGTTGC | TTCCGCCAGT | GGCGCGAAAT | ATTCCCGTGC | ACCTTGCGGA | CGGGTATCCG | 6900 |
| GTTCGTTGGC | AATACTCCAC | ATCACCACGC | TTGGGTGGTT | TTTGTCACGC | GCTATCAGCT | 6960 |
| CTTTAATCGC | CTGTAAGTGC | GCTTGGTGAG | TTTCCCCGTT | GACTGCCTCT | TCGTTGTACA | 7020 |
| GTTCTTTCGG | CTTGTTGCCC | GCTTCGAAAC | CAATGCCTAA | AGAGAGGTTA | AAGCCGACAG | 7080 |
| CAGCAGTTTC | ATCAATCACC | ACGATGCCAT | GTTCATCTGC | CCAGTCGAGC | ATCTCTTCAG | 7140 |
| CGTAAGGGTA | ATGCGAGGTA | CGGTAGGAGT | TGGCCCTAAT | CCAGTCCATT | AATGCGTGGT | 7200 |
| CGTGCACCAT | CAGCACGTTA | TCGAATCCTT | TGCCACGCAA | GTCCGCATCT | TCATGACGAC | 7260 |
| CAAAGCCAGT | AAAGTAGAAC | GGTTTGTGGT | TAATCAGGAA | CTGTTCGCCC | TTCACTGCCA | 7320 |
| CTGACCGGAT | GCCGACGCGA | AGCGGGTAGA | TATCACACTC | TGTCTGGCTT | TTGGCTGTGA | 7380 |
| CGCACAGTTC | ATAGAGATAA | CCTTCACCCG | GTTGCCAGAG | GTGCGGATTC | ACCACTTGCA | 7440 |
| AAGTCCCGCT | AGTGCCTTGT | CCAGTTGCAA | CCACCTGTTG | ATCCGCATCA | CGCAGTTCAA | 7500 |
| CGCTGACATC | ACCATTGGCC | ACCACCTGCC | AGTCAACAGA | CGCGTGGTTA | CAGTCTTGCG | 7560 |
| CGACATGCGT | CACTACGGTG | ATATCGTCCA | CCCAGGTGTT | CGGCGTGGTG | TAGAGCATTA | 7620 |
| CGCTGCGATG | GATTCCGGCA | TAGTTAAAGA | AATCATGGAA | GTAAGATTGC | TTTTCTTGC | 7680 |
| CGTTTTCGTT | GGTAATCACC | ATTCCCGGCG | GGATAGTCTG | CCAGTTCAGT | TCGTTGTTCA | 7740 |
| CACAAACGGT | GATACCCCTC | GACGGATTAA | AGACTTCAAG | CGGTCAACTA | TGAAGAAGTG | 7800 |
| TTCGTCTTCG | TCCCAGTAAG | CTATGTCTCT | AGAATGTAGC | CATCCATCCT | TGTCAATCAA | 7860 |

```
GGCGTTGGTC GCTTCCGGAT TGTTTACATA ACCGGACATA ATCATAGGTC CTCTGACACA   7920
TAATACGCCT CTCTGATTAA CGCCCAGCGT TTTCCCGGTA TCCAGATCCA CAACCTTCGC   7980
TTCAAAAAAT GGAACAACTT TACCGACCGC GCCCGGTTTA TCATCCCCCT CGGGTGTAAT   8040
CAGAATAGCT GATGTAGTCT CAGTGAGCCC ATATCCTTGT CGTATCCCTG GAAGATGGAA   8100
GCGTTTTGCA ACCGCTTCCC CGACTTCTTT CGAAAGAGGT GCGCCCCAG AAGCAATTTC    8160
GTGTAAATTA GATAAATCGT ATTTGTCAAT CAGAGTGCTT TTGGCGAAGA ATGAAAATAG   8220
GGTTGGTACT AGCAACGCAC TTTGAATTTT GTAATCCTGA AGGGATCGTA AAAACAGCTC   8280
TTCTTCAAAT CTATACATTA AGACGACTCG AAATCTACAT ATCAAATATC CGAGTGTAGT   8340
AAACATTCCA AAACCGTGAT GGAATGGAAC AACACTTAAA ATCGCAGTAT CCGGAATGAT   8400
TTGATTGCCA AAAATAGGAT CTCTGGCATG CGAGAATCTA GCGCAGGCAG TTCTATGCGG   8460
AAGGGCCACA CCCTTAGGTA ACCCAGTAGA TCCAGAGGAA TTGTTTTGTC ACGATCAAAG   8520
GACTCTGGTA CAAAATCGTA TTCATTAAAA CCGGGAGGTA GATGAGATGT GACGAAGGTG   8580
TACATCGACT GAAATCCCTG GTAATCCGTT TTAGAATCCA TGATAATAAT TTCTGGATT    8640
ATTGGTAATT TTTTTTGCAC GTTCAAAATT TTTTGCAACC CCTTTTTGGA AACAAACACT   8700
ACGGTAGGCT GCGAAATGTT CATACTGTTG AGCAATTCAC GTTCATTATA AATGTCGTTC   8760
GCGGGCGCAA CTGCAACTCC GATAAATAAC GCGCCCAACA CCGGCATAAA GAATTGAAGA   8820
GAGTTTTCAC TGCATACGAC GATTCTGTGA TTTGTATTCA GCCCATATCG TTTCATAGCT   8880
TCTGCCAACC GAACGGACAT TTCGAAGTAT TCCGCGTACG TGATGTTCAC CTCGATATGT   8940
GCATCTGTAA AAGGAATTGT TCCAGGAACC AGGGCGTATC TCTTCATAGC CTTATGCAGT   9000
TGCTCTCCAG CGGTTCCATT CTCTAGCTTT GCTTCTCAAT TTCTTATTTG CATAATGAGA   9060
AAAAAGGAA AATTAATTTT AACACCAATT CAGTAGTTGA TTGAGCAAAT GCGTTGCCAA    9120
AAAGGATGCT TTAGAGACAG TGTTCTCTGC ACAGATAAGG ACAAACATCA TTCAGAGGGA   9180
GTACCCAGAG CTGAGACTCC TAAGCCAGTG AGTGGCACAG CATTCTAGGG AGAAATATGC   9240
TTGTCATCAC CGAAGCCTGA TTCCGTAGAG CCACACCTTG GTAAGGGCCA ATCTGCTCAC   9300
ACAGGATAGA GAGGGCAGGA GCCAGGGCAG AGCATATAAG GTGAGGTAGG ATCAGTTGCT   9360
CCTCACATTT GCTTCTGACA TAGTTGTGTT GGGAGCTTGG ATCGATCCAC CATGGGCTTC   9420
AATACCCTGA TTGACTGGAA CAGCTGTAGC CCTGAACAGC AGCGTGCGCT GCTGACGCGT   9480
CCGGCGATTT CCGCCTCTGA CAGTATTACC CGGACGGTCA GCGATATTCT GGATAATGCA   9540
AAAACGCGCG GTGACGATGC CCTGCGTGAA TACAGCGCTA AATTTGATAA AACAGAAGTG   9600
ACAGCGCTAC GCGTCACCCC TGAAGAGATC GCCGCCGCCG GCGCGCGTCT GAGCGACGAA   9660
TTAAAACAGG CGATGACCGC TGCCGTCAAA AATATTGAAA CGTTCCATTC CGCGCAGACG   9720
CTACCGCTTG TAGATGTGGA AACCCAGCCA GGCGTGCGTT GCCAGCAGGT TACGCGTCCC   9780
GTCTCGTCTG TCGGTCTGTA TATTCCCGGC GGCTCGGCTC CGCTCTTCTC AACGGTGCTG   9840
ATGCTGGCGA CGCCGGCGCG CATTGCGGGA TGCTAGAAGG TGGTTCTGTG CTCGCCGCCG   9900
CCCATCGCTG ATGAAATCCT CTATGCGGCG CAACTGTGTG GCGTGCAGGA ATTCTTTAAC   9960
CTCGGCGGCG CGCAGGCGAT TGCCGCTCTG GCCTTCGGCA GCGAGTCCGT ACCGAAAGTG  10020
GATAAAATTT TTGGCCCCGG CAACGCCTTT GTAACCGAAG CCAAACGTCA GGTCAGCCAG  10080
CGTCTCGACG GCGCGGCTAT CGATATGCCA GCCGAGCCGT CTGAAGTACT GGTGATCGCA  10140
GACAGCGGCG CAACACCGGA TTTCGTCGCT TCTGACCTGC TCTCCCAGAC TGAGCACGGC  10200
CCGGATTCCC AGGTGATCCT GCTGACGCCT GATGCTGACA TTGCCCGCAA GGTGGCGGAG  10260
```

| | | | | | | |
|---|---|---|---|---|---|---|
| GCGGTAGAAC | GTCAACTGGC | GGAACTGCCG | CGCGCGGACA | CCGCCTGGCA | GGCCCTGAGC | 10320 |
| GCCAGTCGTC | TGATTGTGAC | CAAAGATTTA | GCGCAGTGCG | TCGCCATCTC | TAATCAGTAT | 10380 |
| GGGCCGGAAC | ACTTAATCAT | CCAGACGCGC | AATGCGCGCG | ATTTGGTGGA | TGCGATTACC | 10440 |
| AGCGCAGGCT | CGGTATTTCT | CGGCGACTGG | TCGCCGGAAT | CCGCCGGTGA | TTACGCTTCC | 10500 |
| GGAACCAACC | ATGTTTTACC | GACCTATGGC | CATACTGCTA | CCTGTTCCAG | CCTTGGGTTA | 10560 |
| GCGGATTTCC | AGAAACGGAT | GACCGTTCAG | GAACTGTCGA | AAGCGGGCTT | TTCCGCTCTG | 10620 |
| GCATCAACCA | TTGAAACATT | GGCGGGGGCA | GAACGTCTGA | CCGCCCATAA | AAATGCCGTG | 10680 |
| ACCCTGCGCG | TAAACGCCCT | CAAGGAGCAA | GCATGAGCAC | TGAAAACACT | CTCAGCGTCG | 10740 |
| CTGACTTAGC | CCGTGAAAAT | GTCCGCAACC | TGGAGATCCA | GACATGATAA | GATACATTGA | 10800 |
| TGAGTTTGGA | CAAACCACAA | CTAGAATGCA | GTGAAAAAAA | TGCTTTATTT | GTGAAATTTG | 10860 |
| TGATGCTATT | GCTTTATTTG | TAACCATTAT | AAGCTGCAAT | AAACAAGTTA | ACAACAACAA | 10920 |
| TTGCATTCAT | TTTATGTTTC | AGGTTCAGGG | GGAGGTGTGG | GAGGTTTTTT | AAAGCAAGTA | 10980 |
| AAACCTCTAC | AAATGTGGTA | TGGCTGATTA | TGATCTCTAG | CTCGACGGGG | CGCCTGGCCG | 11040 |
| CTACTAACTC | TCTCCTCCCT | CCTTTTTCCT | GCAGGCTCAA | GGCGCGCATG | CCCGACGGCG | 11100 |
| AGGATCTCGT | CGTGACCCAT | GGCGATGCCT | GCTTGCCGAA | TATCATGGTG | GAAAATGGCC | 11160 |
| GCTTTTCTGG | ATTCATCGAC | TGTGGCCGGC | TGGGTGTGGC | GGACCGCTAT | CAGGACATAG | 11220 |
| CGTTGGCTAC | CCGTGATATT | GCTGAAGAGC | TTGGCGGCGA | ATGGGCTGAC | CGCTTCCTCG | 11280 |
| TGCTTTACGG | TATCGCCGCT | CCCGATTCGC | AGCGCATCGC | CTTCTATCGC | CTTCTTGACG | 11340 |
| AGTTCTTCTG | AGCGGGACTC | TGGGGTTCGA | AATGACCGAC | CAAGCGACGC | CCAACCTGCC | 11400 |
| ATCACGAGAT | TTCGATTCCA | CCGCCGCCTT | CTATGAAAGG | TTGGGCTTCG | GAATCGTTTT | 11460 |
| CCGGGACGCC | GGCTGGATGA | TCCTCCAGCG | CGGGGATCTC | ATGCTGGAGT | TCTTCGCCCA | 11520 |
| CCCCAACTTG | TTTATTGCAG | CTTATAATGG | TTACAAATAA | AGCAATAGCA | TCACAAATTT | 11580 |
| CACAAATAAA | GCATTTTTTT | CACTGCATTC | TAGTTGTGGT | TTGTCCAAAC | TCATCAATCT | 11640 |
| ATCTTATCAT | GTCTGGATCG | CGGCCGGTCT | CTCTCTAGCC | CTAGGTCTAG | ACTTGGCAGA | 11700 |
| ACATATCCAT | CGCGTCCGCC | ATCTCCAGCA | GCCGCACGCG | GCGCATCTCG | GGCAGCGTTG | 11760 |
| GGTCCTGGCC | ACGGGTGCGC | ATGATCGTGC | TCCTGTCGTT | GAGGACCCGG | CTAGGCTGGC | 11820 |
| GGGGTTGCCT | TACTGGTTAG | CAGAATGAAT | CACCGATACG | CGAGCGAACG | TGAAGCGACT | 11880 |
| GCTGCTGCAA | AACGTCTGCG | ACCTGAGCAA | CAACATGAAT | GGTCTTCGGT | TTCCGTGTTT | 11940 |
| CGTAAAGTCT | GGAAACGCGG | AAGTCAGCGC | CCTGCACCAT | TATGTTCCGG | ATCTGCATCG | 12000 |
| CAGGATGCTG | CTGGCTACCC | TGTGGAACAC | CTACATCTGT | ATTAACGAAG | CGCTGGCATT | 12060 |
| GACCCTGAGT | GATTTTTCTC | TGGTCCCGCC | GCATCCATAC | CGCCAGTTGT | TTACCCTCAC | 12120 |
| AACGTTCCAG | TAACCGGGCA | TGTTCATCAT | CAGTAACCCG | TATCGTGAGC | ATCCTCTCTC | 12180 |
| GTTTCATCGG | TATCATTACC | CCCATGAACA | GAAATCCCCC | TTACACGGAG | GCATCAGTGA | 12240 |
| CCAAACAGGA | AAAAACCGCC | CTTAACATGG | CCCGCTTTAT | CAGAAGCCAG | ACATTAACGC | 12300 |
| TTCTGGAGAA | ACTCAACGAG | CTGGACGCGG | ATGAACAGGC | AGACATCTGT | GAATCGCTTC | 12360 |
| ACGACCACGC | TGATGAGCTT | TACCGCAGCT | GCCTCGCGCG | TTTCGGTGAT | GACGGTGAAA | 12420 |
| ACCTCTGACA | CATGCAGCTC | CCGGAGACGG | TCACAGCTTG | TCTGTAAGCG | GATGCCGGGA | 12480 |
| GCAGACAAGC | CCGTCAGGGC | GCGTCAGCGG | GTGTTGGCGG | GTGTCGGGGC | GCAGCCATGA | 12540 |
| CCCAGTCACG | TAGCGATAGC | GGAGTGTATA | CTGGCTTAAC | TATGCGGCAT | CAGAGCAGAT | 12600 |
| TGTACTGAGA | GTGCACCATA | TGCGGTGTGA | AATACCGCAC | AGATGCGTAA | GGAGAAAATA | 12660 |

| | | | | | | |
|---|---|---|---|---|---|---|
| CCGCATCAGG | CGCTCTTCCG | CTTCCTCGCT | CACTGACTCG | CTGCGCTCGG | TCGTTCGGCT | 12720 |
| GCGGCGAGCG | GTATCAGCTC | ACTCAAAGGC | GGTAATACGG | TTATCCACAG | AATCAGGGGA | 12780 |
| TAACGCAGGA | AAGAACATGT | GAGCAAAAGG | CCAGCAAAAG | GCCAGGAACC | GTAAAAGGC | 12840 |
| CGCGTTGCTG | GCGTTTTTCC | ATAGGCTCCG | CCCCCCTGAC | GAGCATCACA | AAAATCGACG | 12900 |
| CTCAAGTCAG | AGGTGGCGAA | ACCCGACAGG | ACTATAAAGA | TACCAGGCGT | TTCCCCCTGG | 12960 |
| AAGCTCCCTC | GTGCGCTCTC | CTGTTCCGAC | CCTGCCGCTT | ACCGGATACC | TGTCCGCCTT | 13020 |
| TCTCCCTTCG | GGAAGCGTGG | CGCTTTCTCA | TAGCTCACGC | TGTAGGTATC | TCAGTTCGGT | 13080 |
| GTAGGTCGTT | CGCTCCAAGC | TGGGCTGTGT | GCACGAACCC | CCCGTTCAGC | CCGACCGCTG | 13140 |
| CGCCTTATCC | GGTAACTATC | GTCTTGAGTC | CAACCCGGTA | AGACACGACT | TATCGCCACT | 13200 |
| GGCAGCAGCC | ACTGGTAACA | GGATTAGCAG | AGCGAGGTAT | GTAGGCGGTG | CTACAGAGTT | 13260 |
| CTTGAAGTGG | TGGCCTAACT | ACGGCTACAC | TAGAAGGACA | GTATTTGGTA | TCTGCGCTCT | 13320 |
| GCTGAAGCCA | GTTACCTTCG | GAAAAAGAGT | TGGTAGCTCT | TGATCCGGCA | AACAAACCAC | 13380 |
| CGCTGGTAGC | GGTGGTTTTT | TTGTTTGCAA | GCAGCAGATT | ACGCGCAGAA | AAAAGGATC | 13440 |
| TCAAGAAGAT | CCTTTGATCT | TTTCTACGGG | GTCTGACGCT | CAGTGGAACG | AAAACTCACG | 13500 |
| TTAAGGGATT | TTGGTCATGA | GATTATCAAA | AAGGATCTTC | ACCTAGATCC | TTTTAAATTA | 13560 |
| AAAATGAAGT | TTTAAATCAA | TCTAAAGTAT | ATATGAGTAA | ACTTGGTCTG | ACAGTTACCA | 13620 |
| ATGCTTAATC | AGTGAGGCAC | CTATCTCAGC | GATCTGTCTA | TTTCGTTCAT | CCATAGTTGC | 13680 |
| CTGACTCCCC | GTCGTGTAGA | TAACTACGAT | ACGGGAGGGC | TTACCATCTG | GCCCCAGTGC | 13740 |
| TGCAATGATA | CCGCGAGACC | CACGCTCACC | GGCTCCAGAT | TTATCAGCAA | TAAACCAGCC | 13800 |
| AGCCGGAAGG | GCCGAGCGCA | GAAGTGGTCC | TGCAACTTTA | TCCGCCTCCA | TCCAGTCTAT | 13860 |
| TAATTGTTGC | CGGGAAGCTA | GAGTAAGTAG | TTCGCCAGTT | AATAGTTTGC | GCAACGTTGT | 13920 |
| TGCCATTGCT | GCAGGCATCG | TGGTGTCACG | CTCGTCGTTT | GGTATGGCTT | CATTCAGCTC | 13980 |
| CGGTTCCCAA | CGATCAAGGC | GAGTTACATG | ATCCCCCATG | TTGTGCAAAA | AAGCGGTTAG | 14040 |
| CTCCTTCGGT | CCTCCGATCG | TTGTCAGAAG | TAAGTTGGCC | GCAGTGTTAT | CACTCATGGT | 14100 |
| TATGGCAGCA | CTGCATAATT | CTCTTACTGT | CATGCCATCC | GTAAGATGCT | TTTCTGTGAC | 14160 |
| TGGTGAGTAC | TCAACCAAGT | CATTCTGAGA | ATAGTGTATG | CGGCGACCGA | GTTGCTCTTG | 14220 |
| CCCGGCGTCA | ACACGGGATA | ATACCGCGCC | ACATAGCAGA | ACTTTAAAAG | TGCTCATCAT | 14280 |
| TGGAAAACGT | TCTTCGGGGC | GAAAACTCTC | AAGGATCTTA | CCGCTGTTGA | GATCCAGTTC | 14340 |
| GATGTAACCC | ACTCGTGCAC | CCAACTGATC | TTCAGCATCT | TTTACTTTCA | CCAGCGTTTC | 14400 |
| TGGGTGAGCA | AAAACAGGAA | GGCAAAATGC | CGCAAAAAAG | GGAATAAGGG | CGACACGGAA | 14460 |
| ATGTTGAATA | CTCATACTCT | TCCTTTTTCA | ATATTATTGA | AGCATTTATC | AGGGTTATTG | 14520 |
| TCTCATGAGC | GGATACATAT | TTGAATGTAT | TTAGAAAAAT | AAACAAATAG | GGGTTCCGCG | 14580 |
| CACATTTCCC | CGAAAAGTGC | CACCTGACGT | CTAAGAAACC | ATTATTATCA | TGACATTAAC | 14640 |
| CTATAAAAAT | AGGCGTATCA | CGAGGCCCTT | TCGTCTTCAA | GAA | | 14683 |

( 2 ) INFORMATION FOR SEQ ID NO:2:

( i ) SEQUENCE CHARACTERISTICS:
        ( A ) LENGTH: 18986 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
TTAATTAAGG  GGCGGAGAAT  GGGCGGAACT  GGGCGGAGTT  AGGGGCGGGA  TGGGCGGAGT      60
TAGGGGCGGG  ACTATGGTTG  CTGACTAATT  GAGATGCATG  CTTTGCATAC  TTCTGCCTGC     120
TGGGGAGCCT  GGGGACTTTC  CACACCTGGT  TGCTGACTAA  TTGAGATGCA  TGCTTTGCAT     180
ACTTCTGCCT  GCTGGGGAGC  CTGGGGACTT  TCCACACCCT  AACTGACACA  CATTCCACAG     240
AATTAATTCC  CCTAGTTATT  AATAGTAATC  AATTACGGGG  TCATTAGGTC  ATAGCCCATA     300
TATGGAGTTC  CGCGTTACAT  AACTTACGGT  AAATGGCCCG  CCTGGCTGAC  CGCCCAACGA     360
CCCCCGCCCA  TTGACGTCAA  TAATGACGTA  TGTTCCCATA  GTAACGCCAA  TAGGGACTTT     420
CCATTGACGT  CAATGGGTGG  ACTATTTACG  GTAAACTGCC  CACTTGGCAG  TACATCAAGT     480
GTATCATATG  CCAAGTACGC  CCCCTATTGA  CGTCAATGAC  GGTAAATGGC  CCGCCTGGCA     540
TTATGCCCAG  TACATGACCT  TATGGGACTT  TCCTACTTGG  CAGTACATCT  ACGTATTAGT     600
CATCGCTATT  ACCATGGTGA  TGCGGTTTTG  GCAGTACATC  AATGGGCGTG  GATAGCGGTT     660
TGACTCACGG  GGATTTCCAA  GTCTCCACCC  CATTGACGTC  AATGGGAGTT  TGTTTTGAAG     720
CTTGGCCGGC  CATATAAACG  GCGGCCAGCT  TTATTTAACG  TGTTACGTC   GAGTCAATTG     780
TACACTAACG  ACAGTGATGA  AAGAAATACA  AAAGCGCATA  ATATTTTGAA  CGACGTCGAA     840
CCTTTATTAC  AAAACAAAAC  ACAAACGAAT  ATCGACAAAG  CTAGATTGCT  GCTACAAGAT     900
TTGGCAAGTT  TTGTGGCGTT  GAGCGAAAAT  CCATTAGATA  GTCCAGCCAT  CGGTTCGGAA     960
AAACAACCCT  TGTTTGAAAC  TAATCGAAAC  CTATTTTACA  AATCTATTGA  GGATTTAATA    1020
TTTAAATTCA  GATATAAAGA  CGCTGAAAAT  CATTTGATTT  TCGCTCTAAC  ATACCACCCT    1080
AAAGATTATA  AATTTAATGA  ATTATTAAAA  TACATCAGCA  ACTATATATT  GATAGACATT    1140
TCCAGTTTGT  GATATTAGTT  TGTGCGTCTC  ATTACAATGG  CTGTTATTTT  TAACAACAAA    1200
CAACTGCTCG  CAGACAATAG  TATAGAAAAG  GGAGGTGAAC  TGTTTTTGTT  TAACGGTTCG    1260
TACAACATTT  TGGAAAGTTA  TGTTAATCCG  GTGCTGCTAA  AAAATGGTGT  AATTGAACTA    1320
GAAGAAGCTG  CGTACTATGC  CGGCAACATA  TTGTACAAAA  CCGACGATCC  CAAATTCATT    1380
GATTATATAA  ATTTAATAAT  TAAAGCAACA  CACTCCGAAG  AACTACCAGA  AAATAGCACT    1440
GTTGTAAATT  ACAGAAAAAC  TATGCGCAGC  GGTACTATAC  ACCCCATTAA  AAAAGACATA    1500
TATATTTATG  ACAACAAAAA  ATTTACTCTA  TACGATAGAT  ACATATATGG  ATACGATAAT    1560
AACTATGTTA  ATTTTTATGA  GGAGAAAAAT  GAAAAGAGA   AGGAATACGA  AGAAGAAGAC    1620
GACAAGGCGT  CTAGTTTATG  TGAAAATAAA  ATTATATTGT  CGCAAATTAA  CTGTGAATCA    1680
TTTGAAAATG  ATTTTAAATA  TTACCTCAGC  GATTATAACT  ACGCGTTTTC  AATTATAGAT    1740
AATACTACAA  ATGTTCTTGT  TGCGTTTGGT  TTGTATCGTT  AATAAAAAC   AAATTTAGCA    1800
TTTATAATTG  TTTTATTATT  CAATAATTAC  AAATAGGATT  GAGACCCTTG  CAGTTGCCAG    1860
CAAACGGACA  GAGCTTGTCG  AGGAGAGTTG  TTGATTCATT  GTTTGCCTCC  CTGCTGCGGT    1920
TTTTCACCGA  AGTTCATGCC  AGTCCAGCGT  TTTTGCAGCA  GAAAAGCCGC  CGACTTCGGT    1980
TTGCGGTCGC  GAGTGAAGAT  CCCTTTCTTG  TTACCGCCAA  CGCGCAATAT  GCCTTGCGAG    2040
GTCGCAAAAT  CGGCGAAATT  CCATACCTGT  TCACCGACGA  CGGCGCTGAC  GCGATCAAAG    2100
ACGCGGTGAT  ACATATCCAG  CCATGCACAC  TGATACTCTT  CACTCCACAT  GTCGGTGTAC    2160
ATTGAGTGCA  GCCCGGCTAA  CGTATCCACG  CCGTATTCGG  TGATGATAAT  CGGCTGATGC    2220
AGTTTCTCCT  GCCAGGCCAG  AAGTTCTTTT  TCCAGTACCT  TCTCTGCCGT  TTCCAAATCG    2280
CCGCTTTGGA  CATACCATCC  GTAATAACGG  TTCAGGCACA  GCACATCAAA  GAGATCGCTG    2340
ATGGTATCGG  TGTGAGCGTC  GCAGAACATT  ACATTGACGC  AGGTGATCGG  ACGCGTCGGG    2400
```

```
TCGAGTTTAC  GCGTTGCTTC  CGCCAGTGGC  GCGAAATATT  CCCGTGCACC  TTGCGGACGG  2460
GTATCCGGTT  CGTTGGCAAT  ACTCCACATC  ACCACGCTTG  GGTGGTTTTT  GTCACGCGCT  2520
ATCAGCTCTT  TAATCGCCTG  TAAGTGCGCT  TGCTGAGTTT  CCCCGTTGAC  TGCCTCTTCG  2580
CTGTACAGTT  CTTTCGGCTT  GTTGCCCGCT  TCGAAACCAA  TGCCTAAAGA  GAGGTTAAAG  2640
CCGACAGCAG  CAGTTTCATC  AATCACCACG  ATGCCATGTT  CATCTGCCCA  GTCGAGCATC  2700
TCTTCAGCGT  AAGGGTAATG  CGAGGTACGG  TAGGAGTTGG  CCCCAATCCA  GTCCATTAAT  2760
GCGTGGTCGT  GCACCATCAG  CACGTTATCG  AATCCTTTGC  CACGCAAGTC  CGCATCTTCA  2820
TGACGACCAA  AGCCAGTAAA  GTAGAACGGT  TTGTGGTTAA  TCAGGAACTG  TTCGCCCTTC  2880
ACTGCCACTG  ACCGGATGCC  GACGCGAAGC  GGGTAGATAT  CACACTCTGT  CTGGCTTTTG  2940
GCTGTGACGC  ACAGTTCATA  GAGATAACCT  TCACCCGGTT  GCCAGAGGTG  CGGATTCACC  3000
ACTTGCAAAG  TCCCGCTAGT  GCCTTGTCCA  GTTGCAACCA  CCTGTTGATC  CGCATCACGC  3060
AGTTCAACGC  TGACATCACC  ATTGGCCACC  ACCTGCCAGT  CAACAGACGC  GTGGTTACAG  3120
TCTTGCGCGA  CATGCGTCAC  CACGGTGATA  TCGTCCACCC  AGGTGTTCGG  CGTGGTGTAG  3180
AGCATTACGC  TGCGATGGAT  TCCGGCATAG  TTAAAGAAAT  CATGGAAGTA  AGACTGCTTT  3240
TTCTTGCCGT  TTTCGTCGGT  AATCACCATT  CCCGGCGGGA  TAGTCTGCCA  GTTCAGTTCG  3300
TTGTTCACAC  AAACGGTGAT  ACCCCTCGAC  GGATTAAAGA  CTTCAAGCGG  TCAACTATGA  3360
AGAAGTGTTC  GTCTTCGTCC  CAGTAAGCTA  TGTCTCCAGA  ATGTAGCCAT  CCATCCTTGT  3420
CAATCAAGGC  GTTGGTCGCT  TCCGGATTGT  TTACATAACC  GGACATAATC  ATAGGTCCTC  3480
TGACACATAA  TTCGCCTCTC  TGATTAACGC  CAGCGTTTT   CCCGGTATCC  AGATCCACAA  3540
CCTTCGCTTC  AAAAAATGGA  ACAACTTTAC  CGACCGCGCC  CGGTTTATCA  TCCCCCTCGG  3600
GTGTAATCAG  AATAGCTGAT  GTAGTCTCAG  TGAGCCCATA  TCCTTGTCGT  ATCCCTGGAA  3660
GATGGAAGCG  TTTTGCAACC  GCTTCCCCGA  CTTCTTTCGA  AAGAGGTGCG  CCCCCAGAAG  3720
CAATTTCGTG  TAAATTAGAT  AAATCGTATT  TGTCAATCAG  AGTGCTTTTG  GCGAAGAATG  3780
AAAATAGGGT  TGGTACTAGC  AACGCACTTT  GAATTTTGTA  ATCCTGAAGG  GATCGTAAAA  3840
ACAGCTCTTC  TTCAAATCTA  TACATTAAGA  CGACTCGAAA  TCCACATATC  AAATATCCGA  3900
GTGTAGTAAA  CATTCCAAAA  CCGTGATGGA  ATGAACAAC   ACTTAAAATC  GCAGTATCCG  3960
GAATGATTTG  ATTGCCAAAA  ATAGGATCTC  TGGCATGCGA  GAATCTAGCG  CAGGCAGTTC  4020
TATGCGGAAG  GGCCACACCC  TTAGGTAACC  CAGTAGATCC  AGAGGAATTG  TTTTGTCACG  4080
ATCAAAGGAC  TCTGGTACAA  AATCGTATTC  ATTAAAACCG  GGAGGTAGAT  GAGATGTGAC  4140
GAACGTGTAC  ATCGACTGAA  ATCCCTGGTA  ATCCGTTTTA  GAATCCATGA  TAATAATTTT  4200
CTGGATTATT  GGTAATTTTT  TTTGCACGTT  CAAAATTTTT  TGCAACCCCT  TTTTGGAAAC  4260
AAACACTACG  GTAGGCTGCG  AAATGTTCAT  ACTGTTGAGC  AATTCACGTT  CATTATAAAT  4320
GTCGTTCGCG  GGCGCAACTG  CAACTCCGAT  AAATAACGCG  CCCAACACCG  GCATAAAGAA  4380
TTGAAGAGAG  TTTTCACTGC  ATACGACGAT  TCTGTGATTT  GTATTCAGCC  CATATCGTTT  4440
CATAGCTTCT  GCCAACCGAA  CGGACATTTC  GAAGTATTCC  GCGTACGTGA  TGTTCACCTC  4500
GATATGTGCA  TCTGTAAAAG  GAATTGTTCC  AGGAACCAGG  GCGTATCTCT  TCATAGCCTT  4560
ATGCAGTTGC  TCTCCAGCGG  TTCCATCCTC  TAGCTTTGCT  TCTCAATTTC  TTATTTGCAT  4620
AATGAGAAAA  AAAGGAAAAT  TAATTTTAAC  ACCAATTCAG  TAGTTGATTG  AGCAAATGCG  4680
TTGCCAAAAA  GGATGCTTTA  GAGACAGTGT  TCTCTGCACA  GATAAGGACA  AACATTATTC  4740
AGAGGGAGTA  CCCAGAGCTG  AGACTCCTAA  GCCAGTGAGT  GGCACAGCAT  TCTAGGGAGA  4800
```

```
AATATGCTTG  TCATCACCGA  AGCCTGATTC  CGTAGAGCCA  CACCTTGGTA  AGGGCCAATC   4860

TGCTCACACA  GGATAGAGAG  GGCAGGAGCC  AGGGCAGAGC  ATATAAGGTG  AGGTAGGATC   4920

AGTTGCTCCT  CACATTTGCT  TCTGACATAG  TTGTGTTGGG  AGCTTGGATC  GATCCACCAT   4980

GGGCTTCAAT  ACCCTGATTG  ACTGGAACAG  CTGTAGCCCT  GAACAGCAGC  GTGCGCTGCT   5040

GACGCGTCCG  GCGATTTCCG  CCTCTGACAG  TATTACCCGG  ACGGTCAGCG  ATATTCTGGA   5100

TAATGTAAAA  ACGCGCGGTG  ACGATGCCCT  GCGTGAATAC  AGCGCTAAAT  TTGATAAAAC   5160

AGAAGTGACA  GCGCTACGCG  TCACCCCTGA  AGAGATCGCC  GCCGCCGGCG  CGCGTCTGAG   5220

CGACGAATTA  AAACAGGCGA  TGACCGCTGC  CGTCAAAAAT  ATTGAAACGT  TCCATTCCGC   5280

GCAGACGCTA  CCGCCTGTAG  ATGTGGAAAC  CCAGCCAGGC  GTGCGTTGCC  AGCAGGTTAC   5340

GCGTCCCGTC  TCGTCTGTCG  GTCTGTATAT  TCCCGGCGGC  TCGGCTCCGC  TCTTCTCAAC   5400

GGTGCTGATG  CTGGCGACGC  CGGCGCGCAT  TGCGGGATGC  CAGAAGGTGG  TTCTGTGCTC   5460

GCCGCCGCCC  ATCGCTGATG  AAATCCTCTA  TGCGGCGCAA  CTGTGTGGCG  TGCAGGAAAT   5520

CTTTAACGTC  GGCGGCGCGC  AGGCGATTGC  CGCTCTGGCC  TTCGGCAGCG  AGTCCGTACC   5580

GAAAGTGGAT  AAAATTTTTG  GCCCCGGCAA  CGCCTTTGTA  ACCGAAGCCA  AACGTCAGGT   5640

CAGCCAGCGT  CTCGACGGCG  CGGCTATCGA  TATGCCAGCC  GGGCCGTCTG  AAGTACTGGT   5700

GATCGCAGAC  AGCGGCGCAA  CACCGGATTT  CGTCGCTTCT  GACCTGCTCT  CCCAGGCTGA   5760

GCACGGCCCG  GATTCCCAGG  TGATCCTGCT  GACGCCTGAT  GCTGACATTG  CCCGCAAGGT   5820

GGCGGAGGCG  GTAGAACGTC  AACTGGCGGA  ACTGCCGCGC  GCGGACACCG  CCCGGCAGGC   5880

CCTGAGCGCC  AGTCGTCTGA  TTGTGACCAA  AGATTTAGCG  CAGTGCGTCG  CCATCTCTAA   5940

TCAGTATGGG  CCGGAACACT  TAATCATCCA  GACGCGCAAT  GCGCGCGATT  TGGTGGATGC   6000

GATTACCAGC  GCAGGCTCGG  TATTTCTCGG  CGACTGGTCG  CCGGAATCCG  CCGGTGATTA   6060

CGCTTCCGGA  ACCAACCATG  TTTTACCGAC  CTATGGCTAT  ACTGCTACCT  GTTCCAGCCT   6120

TGGGTTAGCG  GATTTCCAGA  AACGGATGAC  CGTTCAGGAA  CTGTCGAAAG  CGGGCTTTTC   6180

CGCTCTGGCA  TCAACCATTG  AAACATTGGC  GGCGGCAGAA  CGTCTGACCG  CCCATAAAAA   6240

TGCCGTGACC  CTGCGCGTAA  ACGCCCTCAA  GGAGCAAGCA  TGAGCACTGA  AAACACTCTC   6300

AGCGTCGCTG  ACTTAGCCCG  TGAAAATGTC  CGCAACCTGG  AGATCCAGAC  ATGATAAGAT   6360

ACATTGATGA  GTTTGGACAA  ACCACAACTA  GAATGCAGTG  AAAAAAATGC  TTTATTTGTG   6420

AAATTTGTGA  TGCTATTGCT  TTATTTGTAA  CCATTATAAG  CTGCAATAAA  CAAGTTAACA   6480

ACAACAATTG  CATTCATTTT  ATGTTTCAGG  TTCAGGGGGA  GGTGTGGGAG  GTTTTTTAAA   6540

GCAAGTAAAA  CCTCTACAAA  TGTGGTATGG  CTGATTATGA  TCTCTAGCTC  GACGGCGCGC   6600

CTCTAGAGCA  GTGTGGTTTT  GCAAGAGGAA  GCAAAAAGCC  TCTCCACCCA  GGCCTGGAAT   6660

GTTTCCACCC  AATGTCGAGC  AGTGTGGTTT  TGCAAGAGGA  AGCAAAAGC  CTCTCCACCC   6720

AGGCCTGGAA  TGTTTCCACC  CAATGTCGAG  CAAACCCCGC  CCAGCGTCTT  GTCATTGGCG   6780

AATTCGAACA  CGCAGATGCA  GTCGGGGCGG  CGCGGTCCCA  GTCCACTTC  GCATATTAAG   6840

GTGACGCGTG  TGGCCTCGAA  CACCGAGCGA  CCCTGCAGCC  AATATGGGAT  CGGCCATTGA   6900

ACAAGATGGA  TTGCACGCAG  GTTCTCCGGC  CGCTTGGGTG  GAGAGGCTAT  TCGGCTATGA   6960

CTGGGCACAA  CAGACAATCG  GCTGCTCTGA  TGCCGCCGTG  TTCCGGCTGT  CAGCGCAGGG   7020

GCGCCCGGTT  CTTTTTGTCA  AGACCGACCT  GTCCGGTGCC  CTGAATGAAC  TGCAGGTAAG   7080

TGCGGCCGTC  GATGGCCGAG  GCGGCCTCGG  CCTCTGCATA  AATAAAAAAA  ATTAGTCAGC   7140

CATGCATGGG  GCGGAGAATG  GGCGGAACTG  GGCGGAGTTA  GGGGCGGGAT  GGGCGGAGTT   7200
```

-continued

| | | | | | | |
|---|---|---|---|---|---|---|
| AGGGGCGGGA | CTATGGTTGC | TGACTAATTG | AGATGCATGC | TTTGCATACT | TCTGCCTGCT | 7260 |
| GGGGAGCCTG | GGGACTTTCC | ACACCTGGTT | GCTGACTAAT | TGAGATGCAT | GCTTTGCATA | 7320 |
| CTTCTGCCTG | CTGGGGAGCC | TGGGGACTTT | CCACACCCTA | ACTGACACAC | ATTCCACAGA | 7380 |
| ATTAATTCCC | CTAGTTATTA | ATAGTAATCA | ATTACGGGGT | CATTAGTTCA | TAGCCCATAT | 7440 |
| ATGGAGTTCC | GCGTTACATA | ACTTACGGTA | AATGGCCCGC | CTGGCTGACC | GCCCAACGAC | 7500 |
| CCCCGCCCAT | TGACGTCAAT | AATGACGTAT | GTTCCCATAG | TAACGCCAAT | AGGGACTTTC | 7560 |
| CATTGACGTC | AATGGGTGGA | CTATTTACGG | TAAACTGCCC | ACTTGGCAGT | ACATCAAGTG | 7620 |
| TATCATATGC | CAAGTACGCC | CCCTATTGAC | GTCAATGACG | GTAAATGGCC | CGCCTGGCAT | 7680 |
| TATGCCCAGT | ACATGACCTT | ATGGGACTTT | CCTACTTGGC | AGTACATCTA | GCTATTAGTC | 7740 |
| ATCGCTATTA | CCATGGTGAT | GCGGTTTTGG | CAGTACATCA | ATGGGCGTGG | ATAGCGGTTT | 7800 |
| GACTCACGGG | GATTTCCAAG | TCTCCACCCC | ATTGACGTCA | ATGGGAGTTT | GTTTTGGCAC | 7860 |
| CAAAATCAAC | GGGACTTTCC | AAAATGTCGT | AACAACTCCG | CCCCATTGAC | GCAAATGGGC | 7920 |
| GGTAGGCGTG | TACGGTGGGA | GGTCTATATA | AGCAGAGCTG | GGTACGTGAA | CCGTCAGATC | 7980 |
| GCCTGGAGAC | GCCATCACAG | ATCTCTCACT | ATGGATTTTC | AGGTGCAGAT | TATCAGCTTC | 8040 |
| CTGCTAATCA | GTGCTTCAGT | CATAATGTCC | AGAGGACAAA | TTGTTCTCTC | CCAGTCTCCA | 8100 |
| GCAATCCTGT | CTGCATCTCC | AGGGGAGAAG | GTCACAATGA | CTTGCAGGGC | CAGCTCAAGT | 8160 |
| GTAAGTTACA | TCCACTGGTT | CCAGCAGAAG | CCAGGATCCT | CCCCCAAACC | CTGGATTTAT | 8220 |
| GCCACATCCA | ACCTGGCTTC | TGGAGTCCCT | GTTCGCTTCA | GTGGCAGTGG | GTCTGGGACT | 8280 |
| TCTTACTCTC | TCACAATCAG | CAGAGTGGAG | GCTGAAGATG | CTGCCACTTA | TTACTGCCAG | 8340 |
| CAGTGGACTA | GTAACCCACC | CACGTTCGGA | GGGGGGACCA | AGCTGGAAAT | CAAACGTACG | 8400 |
| GTGGCTGCAC | CATCTGTCTT | CATCTTCCCG | CCATCTGATG | AGCAGTTGAA | ATCTGGAACT | 8460 |
| GCCTCTGTTG | TGTGCCTGCT | GAATAACTTC | TATCCCAGAG | AGGCCAAAGT | ACAGTGGAAG | 8520 |
| GTGGATAACG | CCCTCCAATC | GGGTAACTCC | CAGGAGAGTG | TCACAGAGCA | GGACAGCAAG | 8580 |
| GACAGCACCT | ACAGCCTCAG | CAGCACCCTG | ACGCTGAGCA | AAGCAGACTA | CGAGAAACAC | 8640 |
| AAAGTCTACG | CCTGCGAAGT | CACCCATCAG | GGCCTGAGCT | CGCCCGTCAC | AAAGAGCTTC | 8700 |
| AACAGGGGAG | AGTGTTGAAT | TCAGATCCGT | TAACGGTTAC | CAACTACCTA | GACTGGATTC | 8760 |
| GTGACAACAT | GCGGCCGTGA | TATCTACGTA | TGATCAGCCT | CGACTGTGCC | TTCTAGTTGC | 8820 |
| CAGCCATCTG | TTGTTTGCCC | CTCCCCCGTG | CCTTCCTTGA | CCCTGGAAGG | TGCCACTCCC | 8880 |
| ACTGTCCTTT | CCTAATAAAA | TGAGGAAATT | GCATCGCATT | GTCTGAGTAG | GTGTCATTCT | 8940 |
| ATTCTGGGGG | GTGGGGTGGG | GCAGGACAGC | AAGGGGGAGG | ATTGGGAAGA | CAATAGCAGG | 9000 |
| CATGCTGGGG | ATGCGGTGGG | CTCTATGGAA | CCAGCTGGGG | CTCGACAGCT | ATGCCAAGTA | 9060 |
| CGCCCCCTAT | TGACGTCAAT | GACGGTAAAT | GGCCCGCCTG | GCATTATGCC | CAGTACATGA | 9120 |
| CCTTATGGGA | CTTTCCTACT | TGGCAGTACA | TCTACGTATT | AGTCATCGCT | ATTACCATGG | 9180 |
| TGATGCGGTT | TTGGCAGTAC | ATCAATGGGC | GTGGATAGCG | GTTTGACTCA | CGGGGATTTC | 9240 |
| CAAGTCTCCA | CCCCATTGAC | GTCAATGGGA | GTTTGTTTTG | GCACCAAAAT | CAACGGGACT | 9300 |
| TTCCAAAATG | TCGTAACAAC | TCCGCCCCAT | TGACGCAAAT | GGGCGGTAGG | CGTGTACGGT | 9360 |
| GGGAGGTCTA | TATAAGCAGA | GCTGGGTACG | TCCTCACATT | CAGTGATCAG | CACTGAACAC | 9420 |
| AGACCCGTCG | ACATGGGTTG | GAGCCTCATC | TTGCTCTTCC | TTGTCGCTGT | TGCTACGCGT | 9480 |
| GTCCTGTCCC | AGGTACAACT | GCAGCAGCCT | GGGGCTGAGC | TGGTGAAGCC | TGGGGCCTCA | 9540 |
| GTGAAGATGT | CCTGCAAGGC | TTCTGGCTAC | ACATTTACCA | GTTACAATAT | GCACTGGGTA | 9600 |

| | | | | | | |
|---|---|---|---|---|---|---|
| AAACAGACAC | CTGGTCGGGG | CCTGGAATGG | ATTGGAGCTA | TTTATCCCGG | AAATGGTGAT | 9660 |
| ACTTCCTACA | ATCAGAAGTT | CAAAGGCAAG | GCCACATTGA | CTGCAGACAA | ATCCTCCAGC | 9720 |
| ACAGCCTACA | TGCAGCTCAG | CAGCCTGACA | TCTGAGGACT | CTGCGGTCTA | TTACTGTGCA | 9780 |
| AGATCGACTT | ACTACGGCGG | TGACTGGTAC | TTCAATGTCT | GGGGCGCAGG | GACCACGGTC | 9840 |
| ACCGTCTCTG | CAGCTAGCAC | CAAGGGCCCA | TCGGTCTTCC | CCCTGGCACC | CTCCTCCAAG | 9900 |
| AGCACCTCTG | GGGGCACAGC | GGCCCTGGGC | TGCCTGGTCA | AGGACTACTT | CCCCGAACCG | 9960 |
| GTGACGGTGT | CGTGGAACTC | AGGCGCCCTG | ACCAGCGGCG | TGCACACCTT | CCCGGCTGTC | 10020 |
| CTACAGTCCT | CAGGACTCTA | CTCCCTCAGC | AGCGTGGTGA | CCGTGCCCTC | CAGCAGCTTG | 10080 |
| GGCACCCAGA | CCTACATCTG | CAACGTGAAT | CACAAGCCCA | GCAACACCAA | GGTGGACAAG | 10140 |
| AAAGCAGAGC | CCAAATCTTG | TGACAAAACT | CACACATGCC | CACCGTGCCC | AGCACCTGAA | 10200 |
| CTCCTGGGGG | GACCGTCAGT | CTTCCTCTTC | CCCCCAAAAC | CCAAGGACAC | CCTCATGATC | 10260 |
| TCCCGGACCC | CTGAGGTCAC | ATGCGTGGTG | GTGGACGTGA | GCCACGAAGA | CCCTGAGGTC | 10320 |
| AAGTTCAACT | GGTACGTGGA | CGGCGTGGAG | GTGCATAATG | CCAAGACAAA | GCCGCGGGAG | 10380 |
| GAGCAGTACA | ACAGCACGTA | CCGTGTGGTC | AGCGTCCTCA | CCGTCCTGCA | CCAGGACTGG | 10440 |
| CTGAATGGCA | AGGAGTACAA | GTGCAAGGTC | TCCAACAAAG | CCCTCCCAGC | CCCCATCGAG | 10500 |
| AAAACCATCT | CCAAAGCCAA | AGGGCAGCCC | CGAGAACCAC | AGGTGTACAC | CCTGCCCCCA | 10560 |
| TCCCGGGATG | AGCTGACCAA | GAACCAGGTC | AGCCTGACCT | GCCTGGTCAA | AGGCTTCTAT | 10620 |
| CCCAGCGACA | TCGCCGTGGA | GTGGGAGAGC | AATGGGCAGC | CGGAGAACAA | CTACAAGACC | 10680 |
| ACGCCTCCCG | TGCTGGACTC | CGACGGCTCC | TTCTTCCTCT | ACAGCAAGCT | CACCGTGGAC | 10740 |
| AAGAGCAGGT | GGCAGCAGGG | GAACGTCTTC | TCATGCTCCG | TGATGCATGA | GGCTCTGCAC | 10800 |
| AACCACTACA | CGCAGAAGAG | CCTCTCCCTG | TCTCCGGGTA | AATGAGGATC | CGTTAACGGT | 10860 |
| TACCAACTAC | CTAGACTGGA | TTCGTGACAA | CATGCGGCCG | TGATATCTAC | GTATGATCAG | 10920 |
| CCTCGACTGT | GCCTTCTAGT | TGCCAGCCAT | CTGTTGTTTG | CCCCTCCCCC | GTGCCTTCCT | 10980 |
| TGACCCTGGA | AGGTGCCACT | CCCACTGTCC | TTTCCTAATA | AAATGAGGAA | ATTGCATCGC | 11040 |
| ATTGTCTGAG | TAGGTGTCAT | TCTATTCTGG | GGGTGGGGT | GGGGCAGGAC | AGCAAGGGGG | 11100 |
| AGGATTGGGA | AGACAATAGC | AGGCATGCTG | GGGATGCGGT | GGGCTCTATG | GAACCAGCTG | 11160 |
| GGGCTCGACA | GCAACGCTAG | GTCGAGGCCG | CTACTAACTC | TCTCCTCCCT | CCTTTTTCCT | 11220 |
| GCAGGACGAG | GCAGCGCGGC | TATCGTGGCT | GGCCACGACG | GCGTTCCTT | GCGCAGCTGT | 11280 |
| GCTCGACGTT | GTCACTGAAG | CGGGAAGGGA | CTGGCTGCTA | TTGGGCGAAG | TGCCGGGGCA | 11340 |
| GGATCTCCTG | TCATCTCACC | TTGCTCCTGC | CGAGAAAGTA | TCCATCATGG | CTGATGCAAT | 11400 |
| GCGGCGGCTG | CATACGCTTG | ATCCGGCTAC | CTGCCCATTC | GACCACCAAG | CGAAACATCG | 11460 |
| CATCGAGCGA | GCACGTACTC | GGATGGAAGC | CGGTCTTGTC | GATCAGGATG | ATCTGGACGA | 11520 |
| AGAGCATCAG | GGGCTCGCGC | CAGCCGAACT | GTTCGCCAGG | TAAGTGAGCT | CCAATTCAAG | 11580 |
| CTTCCTAGGG | CGGCCAGCTA | GTAGCTTTGC | TTCTCAATTT | CTTATTTGCA | TAATGAGAAA | 11640 |
| AAAAGGAAAA | TTAATTTTAA | CACCAATTCA | GTAGTTGATT | GAGCAAATGC | GTTGCCAAAA | 11700 |
| AGGATGCTTT | AGAGACAGTG | TTCTCTGCAC | AGATAAGGAC | AAACATTATT | CAGAGGGAGT | 11760 |
| ACCCAGAGCT | GAGACTCCTA | AGCCAGTGAG | TGGCACAGCA | TTCTAGGGAG | AAATATGCTT | 11820 |
| GTCATCACCG | AAGCCTGATT | CCGTAGAGCC | ACACCTTGGT | AAGGGCCAAT | CTGCTCACAC | 11880 |
| AGGATAGAGA | GGGCAGGAGC | CAGGGCAGAG | CATATAAGGT | GAGGTAGGAT | CAGTTGCTCC | 11940 |
| TCACATTTGC | TTCTGACATA | GTTGTGTTGG | GAGCTTGGAT | AGCTTGGACA | GCTCAGGGCT | 12000 |

```
GCGATTTCGC GCCAAACTTG ACGGCAATCC TAGCGTGAAG GCTGGTAGGA TTTTATCCCC    12060
GCTGCCATCA TGGTTCGACC ATTGAACTGC ATCGTCGCCG TGTCCCAAAA TATGGGGATT    12120
GGCAAGAACG GAGACCTACC CTGGCCTCCG CTCAGGAACG AGTTCAAGTA CTTCCAAAGA    12180
ATGACCACAA CCTCTTCAGT GGAAGGTAAA CAGAATCTGG TGATTATGGG TAGGAAAACC    12240
TGGTTCTCCA TTCCTGAGAA GAATCGACCT TTAAAGGACA GAATTAATAT AGTTCTCAGT    12300
AGAGAACTCA AAGAACCACC ACGAGGAGCT CATTTCTTG CCAAAAGTTT GGATGATGCC     12360
TTAAGACTTA TTGAACAACC GGAATTGGCA AGTAAAGTAG ACATGGTTTG GATAGTCGGA    12420
GGCAGTTCTG TTTACCAGGA AGCCATGAAT CAACCAGGCC ACCTTAGACT CTTTGTGACA    12480
AGGATCATGC AGGAATTTGA AAGTGACACG TTTTTCCCAG AAATTGATTT GGGGAAATAT    12540
AAACTTCTCC CAGAATACCC AGGCGTCCTC TCTGAGGTCC AGGAGGAAAA AGGCATCAAG    12600
TATAAGTTTG AAGTCTACGA GAAGAAAGAC TAACAGGAAG ATGCTTTCAA GTTCTCTGCT    12660
CCCCTCCTAA AGCTATGCAT TTTTATAAGA CCATGGGACT TTTGCTGGCT TTAGATCAGC    12720
CTCGACTGTG CCTTCTAGTT GCCAGCCATC TGTTGTTTGC CCCTCCCCG TGCCTTCCTT     12780
GACCCTGGAA GGTGCCACTC CCACTGTCCT TTCCTAATAA AATGAGGAAA TTGCATCGCA    12840
TTGTCTGAGT AGGTGTCATT CTATTCTGGG GGGTGGGGTG GGGCAGGACA GCAAGGGGGA    12900
GGATTGGGAA GACAATAGCA GGCATGCTGG GGATGCGGTG GGCTCTATGG AACCAGCTGG    12960
GGCTCGAAGC GGCCGCCCAT TTCGCTGGTG GTCAGATGCG GGATGGCGTG GGACGCGGCG    13020
GGGAGCGTCA CACTGAGGTT TTCCGCCAGA CGCCACTGCT GCCAGGCGCT GATGTGCCCG    13080
GCTTCTGACC ATGCGGTCGC GTTCGGTTGC ACTACGCGTA CTGTGAGCCA GAGTTGCCCG    13140
GCGCTCTCCG GCTGCGGTAG TTCAGGCAGT TCAATCAACT GTTACCTTG TGGACCGACA     13200
TCCAGAGGCA CTTCACCGCT TGCCAGCGGC TTACCATCCA GCGCCACCAT CCAGTGCAGG    13260
AGCTCGTTAT CGCTATGACG GAACAGGTAT TCGCTGGTCA CTTCGATGGT TTGCCCGGAT    13320
AAACGGAACT GGAAAAACTG CTGCTGGTGT TTTGCTTCCG TCAGCGCTGG ATGCGGCGTG    13380
CGGTCGGCAA AGACCAGACC GTTCATACAG AACTGGCGAT CGTTCGGCGT ATCGCCAAAA    13440
TCACCGCCGT AAGCCGACCA CGGGTTGCCG TTTTCATCAT ATTTAATCAG CGACTGATCC    13500
ACCCAGTCCC AGACGAAGCC GCCCTGTAAA CGGGGATACT GACGAAACGC CTGCCAGTAT    13560
TTAGCGAAAC CGCCAAGACT GTTACCCATC GCTGGGGCGT ATTCGCAAAG GATCAGCGGG    13620
CGCGTCTCTC CGGGTAGCGA AAGCCATTTT TTGATGGACC ATTTCGGACC AGCCGGGAAG    13680
GGCTGGTCTT CATCCACGCG CGCGTACATC GGGCAAATAA TATCGGTGGC CGTGGTGTCG    13740
GCTCCGCCGC CTTCATACTG CACCGGGCGG GAAGGATCGA CAGATTTGAT CCAGCGATAC    13800
AGCGCGTCGT GATTAGCGCC GTGGCCTGAT TCATTCCCCA GCGACCAGAT GATCACACTC    13860
GGGTGATTAC GATCGCGCTG CACCATTCGC GTTACGCGTT CGCTCATCGC CGGTAGCCAG    13920
CGCGGATCAT CGGTCAGACG ATTCATTGGC ACCATGCCGT GGGTTTCAAT ATTGGCTTCA    13980
TCCACCACAT ACAGGCCGTA GCGGTCGCAC AGCGTGTACC ACAGCGGATG GTTCGGATAA    14040
TGCCAACAGC GCACGGCGTT AAAGTTGTTC TGCTTCATCA GCAGGATATC CTGCACCATC    14100
GTCTGCTCAT CCATGACCTG ACCATGCAGA GGATGATGCT CGTGACGGTT AACGCCTCGA    14160
ATCAGCAACG GCTTGCCGTT CAGCAGCAGC AGACCATTTT CAATCCGCAC CTCGCGGAAA    14220
CCGACATCGC AGGCTTCTGC TTCAATCAGC GTGCCGTCGG CGGTGTGCAG TTCAACCACC    14280
GCACGATAGA GATTCGGGAT TTCGGCGCTC CACAGTTTCG GGTTTTCGAC GTTCAGACGC    14340
AGTGTGACGC GATCGGCATA ACCACCACGC TCATCGATAA TTTCACCGCC GAAAGGCGCG    14400
```

-continued

```
GTGCCGCTGG CGACCTGCGT TTCACCCTGC CATAAAGAAA CTGTTACCCG TAGGTAGTCA    14460
CGCAACTCGC CGCACATCTG AACTTCAGCC TCCAGTACAG CGCGGCTGAA ATCATCATTA    14520
AAGCGAGTGG CAACATGGAA ATCGCTGATT TGTGTAGTCG GTTTATGCAG CAACGAGACG    14580
TCACGGAAAA TGCCGCTCAT CCGCCACATA TCCTGATCTT CCAGATAACT GCCGTCACTC    14640
CAACGCAGCA CCATCACCGC GAGGCGGTTT TCTCCGGCGC GTAAAAATGC GCTCAGGTCA    14700
AATTCAGACG GCAAACGACT GTCCTGGCCG TAACCGACCC ACGCCCGTT GCACCACAGA     14760
TGAAACGCCG AGTTAACGCC ATCAAAAATA ATTCGCGTCT GGCCTTCCTG TAGCCAGCTT    14820
TCATCAACAT TAAATGTGAG CGAGTAACAA CCCGTCGGAT TCTCCGTGGG AACAAACGGC    14880
GGATTGACCG TAATGGGATA GGTTACGTTG GTGTAGATGG GCGCATCGTA ACCGTGCATC    14940
TGCCAGTTTG AGGGGACGAC GACAGTATCG GCCTCAGGAA GATCGCACTC CAGCCAGCTT    15000
TCCGGCACCG CTTCTGGTGC CGGAAACCAG GCAAAGCGCC ATTCGCCATT CAGGCTGCGC    15060
AACTGTTGGG AAGGGCGATC GGTGCGGGCC TCTTCGCTAT TACGCCAGCT GGCGAAAGGG    15120
GGATGTGCTG CAAGGCGATT AAGTTGGGTA ACGCCAGGGT TTTCCCAGTC ACGACGTTGT    15180
AAAACGACTT AATCCGTCGA GGGGCTGCCT CGAAGCAGAC GACCTTCCGT TGTGCAGCCA    15240
GCGGCGCCTG CGCCGGTGCC CACAATCGTG CGCGAACAAA CTAAACCAGA ACAAATTATA    15300
CCGGCGGCAC CGCCGCCACC ACCTTCTCCC GTGCCTAACA TTCCAGCGCC TCCACCACCA    15360
CCACCACCAT CGATGTCTGA ATTGCCGCCC GCTCCACCAA TGCCGACGGA ACCTCAACCC    15420
GCTGCACCTT TAGACGACAG ACAACAATTG TTGGAAGCTA TTAGAAACGA AAAAAATCGC    15480
ACTCGTCTCA GACCGGTCAA ACCAAAAACG GCGCCCGAAA CCAGTACAAT AGTTGAGGTG    15540
CCGACTGTGT TGCCTAAAGA GACATTTGAG CCTAAACCGC CGTCTGCATC ACCGCCACCA    15600
CCTCCGCCTC CGCCTCCGCC GCCAGCCCCG CCTGCGCCTC CACCGATGGT AGATTTATCA    15660
TCAGCTCCAC CACCGCCGCC ATTAGTAGAT TTGCCGTCTG AAATGTTACC ACCGCCTGCA    15720
CCATCGCTTT CTAACGTGTT GTCTGAATTA AAATCGGGCA CAGTTAGATT GAAACCCGCC    15780
CAAAAACGCC CGCAATCAGA AATAATTCCA AAAAGCTCAA CTACAAATTT GATCGCGGAC    15840
GTGTTAGCCG ACACAATTAA TAGGCGTCGT GTGGCTATGG CAAAATCGTC TTCGGAAGCA    15900
ACTTCTAACG ACGAGGGTTG GGACGACGAC GATAATCGGC CTAATAAAGC TAACACGCCC    15960
GATGTTAAAT ATGTCCAAGC TACTAGTGGT ACCGCTTGGC AGAACATATC CATCGCGTCC    16020
GCCATCTCCA GCAGCCGCAC GCGGCGCATC TCGGGCAGCG TTGGGTCCTG GCCACGGGTG    16080
CGCATGATCG TGCTCCTGTC GTTGAGGACC CGGCTAGGCT GGCGGGGTTG CCTTACTGGT    16140
TAGCAGAATG AATCACCGAT ACGCGAGCGA ACGTGAAGCG ACTGCTGCTG CAAAACGTCT    16200
GCGACCTGAG CAACAACATG AATGGTCTTC GGTTTCCGTG TTTCGTAAAG TCTGGAAACG    16260
CGGAAGTCAG CGCCCTGCAC CATTATGTTC CGGATCTGCA TCGCAGGATG CTGCTGGCTA    16320
CCCTGTGGAA CACCTACATC TGTATTAACG AAGCGCTGGC ATTGACCCTG AGTGATTTTT    16380
CTCTGGTCCC GCCGCATCCA TACCGCCAGT TGTTTACCCT CACAACGTTC CAGTAACCGG    16440
GCATGTTCAT CATCAGTAAC CCGTATCGTG AGCATCCTCT CTCGTTTCAT CGGTATCATT    16500
ACCCCCATGA ACAGAAATCC CCCTTACACG GAGGCATCAG TGACCAAACA GGAAAAAACC    16560
GCCCTTAACA TGGCCCGCTT TATCAGAAGC CAGACATTAA CGCTTCTGGA GAAACTCAAC    16620
GAGCTGGACG CGGATGAACA GGCAGACATC TGTGAATCGC TTCACGACCA CGCTGATGAG    16680
CTTTACCGCA GCTGCCTCGC GCGTTTCGGT GATGACGGTG AAAACCTCTG ACACATGCAG    16740
CTCCCGGAGA CGGTCACAGC TTGTCTGTAA GCGGATGCCG GGAGCAGACA AGCCCGTCAG    16800
```

```
GGCGCGTCAG CGGGTGTTGG CGGGTGTCGG GGCGCAGCCA TGACCCAGTC ACGTAGCGAT    16860
AGCGGAGTGT ATACTGGCTT AACTATGCGG CATCAGAGCA GATTGTACTG AGAGTGCACC    16920
ATATGCGGTG TGAAATACCG CACAGATGCG TAAGGAGAAA ATACCGCATC AGGCGCTCTT    16980
CCGCTTCCTC GCTCACTGAC TCGCTGCGCT CGGTCGTTCG GCTGCGGCGA GCGGTATCAG    17040
CTCACTCAAA GGCGGTAATA CGGTTATCCA CAGAATCAGG GGATAACGCA GGAAAGAACA    17100
TGTGAGCAAA AGGCCAGCAA AAGGCCAGGA ACCGTAAAAA GGCCGCGTTG CTGGCGTTTT    17160
TCCATAGGCT CCGCCCCCCT GACGAGCATC ACAAAAATCG ACGCTCAAGT CAGAGGTGGC    17220
GAAACCCGAC AGGACTATAA AGATACCAGG CGTTTCCCCC TGGAAGCTCC CTCGTGCGCT    17280
CTCCTGTTCC GACCCTGCCG CTTACCGGAT ACCTGTCCGC CTTTCTCCCT TCGGGAAGCG    17340
TGGCGCTTTC TCATAGCTCA CGCTGTAGGT ATCTCAGTTC GGTGTAGGTC GTTCGCTCCA    17400
AGCTGGGCTG TGTGCACGAA CCCCCCGTTC AGCCCGACCG CTGCGCCTTA TCCGGTAACT    17460
ATCGTCTTGA GTCCAACCCG GTAAGACACG ACTTATCGCC ACTGGCAGCA GCCACTGGTA    17520
ACAGGATTAG CAGAGCGAGG TATGTAGGCG GTGCTACAGA GTTCTTGAAG TGGTGGCCTA    17580
ACTACGGCTA CACTAGAAGG ACAGTATTTG GTATCTGCGC TCTGCTGAAG CCAGTTACCT    17640
TCGGAAAAAG AGTTGGTAGC TCTTGATCCG GCAAACAAAC CACCGCTGGT AGCGGTGGTT    17700
TTTTGTTTG CAAGCAGCAG ATTACGCGCA GAAAAAAGG ATCTCAAGAA GATCCTTTGA    17760
TCTTTTCTAC GGGGTCTGAC GCTCAGTGGA ACGAAAACTC ACGTTAAGGG ATTTTGGTCA    17820
TGAGATTATC AAAAAGGATC TTCACCTAGA TCCTTTTAAA TTAAAAATGA AGTTTTAAAT    17880
CAATCTAAAG TATATATGAG TAAACTTGGT CTGACAGTTA CCAATGCTTA ATCAGTGAGG    17940
CACCTATCTC AGCGATCTGT CTATTTCGTT CATCCATAGT TGCCTGACTC CCCGTCGTGT    18000
AGATAACTAC GATACGGGAG GGCTTACCAT CTGGCCCCAG TGCTGCAATG ATACCGCGAG    18060
ACCCACGCTC ACCGGCTCCA GATTTATCAG CAATAAACCA GCCAGCCGGA AGGGCCGAGC    18120
GCAGAAGTGG TCCTGCAACT TTATCCGCCT CCATCCAGTC TATTAATTGT TGCCGGGAAG    18180
CTAGAGTAAG TAGTTCGCCA GTTAATAGTT TGCGCAACGT TGTTGCCATT GCTGCAGGCA    18240
TCGTGGTGTC ACGCTCGTCG TTTGGTATGG CTTCATTCAG CTCCGGTTCC CAACGATCAA    18300
GGCGAGTTAC ATGATCCCCC ATGTTGTGCA AAAAAGCGGT TAGCTCCTTC GGTCCTCCGA    18360
TCGTTGTCAG AAGTAAGTTG GCCGCAGTGT TATCACTCAT GGTTATGGCA GCACTGCATA    18420
ATTCTCTTAC TGTCATGCCA TCCGTAAGAT GCTTTTCTGT GACTGGTGAG TACTCAACCA    18480
AGTCATTCTG AGAATAGTGT ATGCGGCGAC CGAGTTGCTC TTGCCCGGCG TCAACACGGG    18540
ATAATACCGC GCCACATAGC AGAACTTTAA AAGTGCTCAT CATTGGAAAA CGTTCTTCGG    18600
GGCGAAAACT CTCAAGGATC TTACCGCTGT TGAGATCCAG TTCGATGTAA CCCACTCGTG    18660
CACCCAACTG ATCTTCAGCA TCTTTTACTT TCACCAGCGT TTCTGGGTGA GCAAAAACAG    18720
GAAGGCAAAA TGCCGCAAAA AAGGGAATAA GGGCGACACG GAAATGTTGA ATACTCATAC    18780
TCTTCCTTTT TCAATATTAT TGAAGCATTT ATCAGGGTTA TTGTCTCATG AGCGGATACA    18840
TATTTGAATG TATTTAGAAA AATAAACAAA TAGGGGTTCC GCGCACATTT CCCCGAAAAG    18900
TGCCACCTGA CGTCTAAGAA ACCATTATTA TCATGACATT AACCTATAAA AATAGGCGTA    18960
TCACGAGGCC CTTTCGTCTT CAAGAA                                        18986
```